US012377197B2

(12) United States Patent
McGill et al.

(10) Patent No.: US 12,377,197 B2
(45) Date of Patent: Aug. 5, 2025

(54) DISPOSABLE COMPONENTS FOR FLUID LINE AUTOCONNECT SYSTEMS AND METHODS

(71) Applicant: DEKA Products Limited Partnership, Manchester, NH (US)

(72) Inventors: David W. McGill, Woodstock, GA (US); Jacob W. Scarpaci, Manchester, NH (US); James D. Dale, Milton, FL (US); Simon C. Helmore, San Francisco, CA (US); Jason A. Demers, Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 391 days.

(21) Appl. No.: 17/668,554

(22) Filed: Feb. 10, 2022

(65) Prior Publication Data

US 2022/0233754 A1 Jul. 28, 2022

Related U.S. Application Data

(63) Continuation of application No. 16/207,349, filed on Dec. 3, 2018, now Pat. No. 11,253,636, which is a
(Continued)

(51) Int. Cl.
*A61M 1/14* (2006.01)
*A61M 1/16* (2006.01)
(Continued)

(52) U.S. Cl.
CPC ............ *A61M 1/1565* (2022.05); *A61M 1/14* (2013.01); *A61M 1/15* (2022.05); *A61M 1/155* (2022.05);
(Continued)

(58) Field of Classification Search
CPC .......... A61M 1/14; A61M 1/15; A61M 1/152; A61M 1/155; A61M 1/156; A61M 1/1561;
(Continued)

(56) References Cited

U.S. PATENT DOCUMENTS 3,410,202 A 11/1968 Chrubasik
3,656,873 A 4/1972 Schiff
(Continued)

FOREIGN PATENT DOCUMENTS

EP 0 288 145 A1 10/1988
EP 0 406 562 A2 1/1991
(Continued)

OTHER PUBLICATIONS

[No Author Listed] Homechoice Patient At-Home Guide, Jun. 1998. 84 pages.
(Continued)

*Primary Examiner* — Shefali D Patel
(74) *Attorney, Agent, or Firm* — Wolf, Greenfield & Sacks, P.C.

(57) ABSTRACT

Components for a medical infusion fluid handling system, such as an APD system, in which one or more lines (such as solution lines), spikes or other connection ports may be automatically capped and/or de-capped. This feature may provide advantages, such as a reduced likelihood of contamination since no human interaction is required to de-cap and connect the one or more lines, the spikes, or the other connection ports. For example, a fluid handling cassette may include one or more caps that cover a corresponding spike and include a raised and/or recessed feature to assist in removal of the one or more caps from the cassette. A solution
(Continued)

line cap may include a hole and a recess, a groove or other feature to engage with a spike cap and enable removal of the spike cap.

9 Claims, 54 Drawing Sheets

Related U.S. Application Data continuation of application No. 15/837,182, filed on Dec. 11, 2017, now Pat. No. 10,172,988, which is a continuation of application No. 14/466,437, filed on Aug. 22, 2014, now Pat. No. 9,839,775, which is a continuation of application No. 12/864,322, filed as application No. PCT/US2009/000441 on Jan. 23, 2009, now Pat. No. 8,840,581.

(60) Provisional application No. 61/058,469, filed on Jun. 3, 2008, provisional application No. 61/011,967, filed on Jan. 23, 2008.

(51) Int. Cl.
*A61M 1/28* (2006.01)
*A61M 5/168* (2006.01)
*A61M 39/10* (2006.01)
*A61M 39/20* (2006.01)
*A61M 39/28* (2006.01)
*F04B 43/02* (2006.01)
*F04B 43/073* (2006.01)
*F04B 43/08* (2006.01)

(52) U.S. Cl.
CPC .......... *A61M 1/1561* (2022.05); *A61M 1/159* (2022.05); *A61M 1/16* (2013.01); *A61M 1/28* (2013.01); *A61M 5/16809* (2013.01); *A61M 1/1522* (2022.05); *A61M 1/1524* (2022.05); *A61M 1/153* (2022.05); *A61M 1/1601* (2014.02); *A61M 1/1623* (2014.02); *A61M 1/1629* (2014.02); *A61M 1/1631* (2014.02); *A61M 1/166* (2014.02); *A61M 1/1694* (2013.01); *A61M 1/281* (2014.02); *A61M 1/282* (2014.02); *A61M 1/288* (2014.02); *A61M 5/16813* (2013.01); *A61M 5/16827* (2013.01); *A61M 39/1011* (2013.01); *A61M 39/105* (2013.01); *A61M 2039/1066* (2013.01); *A61M 39/20* (2013.01); *A61M 39/28* (2013.01); *A61M 39/281* (2013.01); *A61M 2205/12* (2013.01); *A61M 2205/121* (2013.01); *A61M 2205/122* (2013.01); *A61M 2205/123* (2013.01); *A61M 2205/127* (2013.01); *A61M 2205/128* (2013.01); *A61M 2205/13* (2013.01); *A61M 2205/14* (2013.01); *A61M 2205/3306* (2013.01); *A61M 2205/3331* (2013.01); *A61M 2205/3334* (2013.01); *A61M 2205/3379* (2013.01); *A61M 2205/36* (2013.01); *A61M 2205/502* (2013.01); *A61M 2209/08* (2013.01); *F04B 43/02* (2013.01); *F04B 43/073* (2013.01); *F04B 43/08* (2013.01); *F04B 43/086* (2013.01); *Y02A 90/10* (2018.01)

(58) Field of Classification Search
CPC .............. A61M 1/1562; A61M 1/1565; A61M 1/159; A61M 1/16; A61M 1/1621; A61M 1/1623; A61M 1/1629; A61M 1/1631; A61M 1/1694; A61M 1/28; A61M 1/281; A61M 1/282; A61M 1/288; A61M 2039/1066; A61M 2205/12; A61M 2205/121; A61M 2205/122; A61M 2205/123; A61M 2205/127; A61M 2205/128; A61M 2205/13; A61M 2205/14; A61M 2205/3306; A61M 2205/3331; A61M 2205/3334; A61M 2205/3379; A61M 2205/3396; A61M 2205/36; A61M 2205/502; A61M 2209/08; A61M 39/1011; A61M 39/105; A61M 39/20; A61M 39/22; A61M 39/28; A61M 39/281; A61M 5/145; A61M 5/14586; A61M 5/16809; A61M 5/16813; A61M 5/16827; F04B 43/02; F04B 43/025; F04B 43/073; F04B 43/0733; F04B 43/0736; F04B 43/08; F04B 43/086; F04B 43/113; F04B 43/1133; F04B 43/1136

See application file for complete search history.

(56) References Cited

U.S. PATENT DOCUMENTS

| | | |
|---|---|---|
| 3,741,687 A | 6/1973 | Nystroem |
| 3,946,731 A | 3/1976 | Lichtenstein |
| 4,468,223 A | 8/1984 | Minagawa et al. |
| 4,479,762 A | 10/1984 | Bilstad et al. |
| 4,707,335 A | 11/1987 | Fentress et al. |
| 4,906,816 A | 3/1990 | van Leerdam |
| 4,927,411 A | 5/1990 | Pastrone et al. |
| 5,062,774 A | 11/1991 | Kramer et al. |
| 5,088,515 A | 2/1992 | Kamen |
| 5,098,262 A | 3/1992 | Wecker et al. |
| 5,178,182 A | 1/1993 | Kamen |
| 5,214,241 A | 5/1993 | Benwell |
| 5,267,956 A | 12/1993 | Beuchat |
| 5,275,724 A | 1/1994 | Bucchianeri et al. |
| 5,302,093 A | 4/1994 | Owens et al. |
| 5,306,242 A | 4/1994 | Joyce et al. |
| 5,324,422 A | 6/1994 | Colleran et al. |
| D350,823 S | 9/1994 | Lanigan |
| 5,350,357 A | 9/1994 | Kamen et al. |
| 5,357,827 A | 10/1994 | Natwick et al. |
| 5,378,126 A | 1/1995 | Abrahamson et al. |
| 5,401,342 A | 3/1995 | Vincent et al. |
| 5,415,528 A | 5/1995 | Ogden et al. |
| 5,421,823 A | 6/1995 | Kamen et al. |
| 5,427,509 A | 6/1995 | Chapman et al. |
| 5,431,627 A | 7/1995 | Pastrone et al. |
| 5,437,635 A | 8/1995 | Fields et al. |
| 5,438,510 A | 8/1995 | Bryant et al. |
| 5,462,416 A | 10/1995 | Dennehey et al. |
| 5,476,368 A | 12/1995 | Rabenau et al. |
| 5,480,294 A | 1/1996 | Di Perna et al. |
| 5,488,967 A | 2/1996 | Minami et al. |
| 5,496,273 A | 3/1996 | Pastrone et al. |
| 5,499,909 A | 3/1996 | Yamada et al. |
| 5,591,344 A | 1/1997 | Kenley et al. |
| 5,593,290 A | 1/1997 | Greisch et al. |
| 5,628,908 A | 5/1997 | Kamen et al. |
| 5,638,737 A | 6/1997 | Mattson et al. |
| 5,640,995 A | 6/1997 | Packard et al. |
| 5,704,520 A | 1/1998 | Gross |
| 5,714,060 A | 2/1998 | Kenley et al. |
| 5,722,947 A | 3/1998 | Jeppsson et al. |
| 5,863,421 A | 1/1999 | Peter, Jr. et al. |
| 5,938,634 A | 8/1999 | Packard |
| 6,070,761 A | 6/2000 | Bloom et al. |
| 6,165,154 A | 12/2000 | Gray et al. |
| 6,210,361 B1 | 4/2001 | Kamen et al. |
| 6,223,130 B1 | 4/2001 | Gray et al. |
| 6,234,989 B1 | 5/2001 | Brierton et al. |
| 6,261,065 B1 | 7/2001 | Nayak et al. |
| 6,261,262 B1 | 7/2001 | Briggs et al. |
| 6,270,673 B1 | 8/2001 | Belt et al. |
| 6,302,653 B1 | 10/2001 | Bryant et al. |

(56) References Cited

U.S. PATENT DOCUMENTS

| | | |
|---|---|---|
| 6,340,294 B1 | 1/2002 | Kubota et al. |
| 6,382,923 B1 | 5/2002 | Gray |
| 6,416,293 B1 | 7/2002 | Bouchard et al. |
| 6,481,980 B1 | 11/2002 | Vandlik et al. |
| 6,491,656 B1 | 12/2002 | Morris |
| 6,497,676 B1 | 12/2002 | Childers et al. |
| 6,503,062 B1 | 1/2003 | Gray et al. |
| 6,520,747 B2 | 2/2003 | Gray et al. |
| 6,537,445 B2 | 3/2003 | Muller |
| 6,579,253 B1 | 6/2003 | Burbank et al. |
| RE38,203 E | 7/2003 | Kelly |
| 6,638,478 B1 | 10/2003 | Treu et al. |
| 6,673,314 B1 | 1/2004 | Burbank et al. |
| 6,709,417 B1 | 3/2004 | Houle et al. |
| 6,723,062 B1 | 4/2004 | Westberg et al. |
| 6,726,656 B2 | 4/2004 | Kamen et al. |
| 6,743,201 B1 | 6/2004 | Donig et al. |
| 6,752,172 B2 | 6/2004 | Lauer |
| 6,814,547 B2 | 11/2004 | Childers et al. |
| 6,852,090 B2 | 2/2005 | Burbank et al. |
| 6,860,846 B2 | 3/2005 | Odak et al. |
| 6,905,314 B2 | 6/2005 | Danby |
| 6,905,479 B1 | 6/2005 | Bouchard et al. |
| 6,929,751 B2 | 8/2005 | Bowman, Jr. et al. |
| 6,949,079 B1 | 9/2005 | Westberg et al. |
| 6,953,323 B2 | 10/2005 | Childers et al. |
| 7,033,539 B2 | 4/2006 | Krensky et al. |
| 7,041,076 B1 | 5/2006 | Westberg et al. |
| 7,044,432 B2 | 5/2006 | Beden et al. |
| 7,083,719 B2 | 8/2006 | Bowman, Jr. et al. |
| 7,153,286 B2 | 12/2006 | Busby et al. |
| 7,175,606 B2 | 2/2007 | Bowman, Jr. et al. |
| 7,214,210 B2 | 5/2007 | Kamen et al. |
| 7,238,164 B2 | 7/2007 | Childers et al. |
| 7,300,413 B2 | 11/2007 | Burbank et al. |
| 7,461,968 B2 | 12/2008 | Demers et al. |
| 7,465,285 B2 | 12/2008 | Hutchinson et al. |
| 7,473,238 B2 | 1/2009 | Brugger et al. |
| 7,500,962 B2 | 3/2009 | Childers et al. |
| 7,559,524 B2 | 7/2009 | Gray et al. |
| 7,563,248 B2 | 7/2009 | Smisson, III et al. |
| 7,575,564 B2 | 8/2009 | Childers |
| 7,632,078 B2 | 12/2009 | Demers et al. |
| 7,632,080 B2 | 12/2009 | Tracey et al. |
| 7,648,627 B2 | 1/2010 | Beden et al. |
| 7,662,139 B2 | 2/2010 | Demers et al. |
| 7,717,682 B2 | 5/2010 | Orr |
| 7,736,328 B2 | 6/2010 | Childers et al. |
| 7,776,006 B2 | 8/2010 | Childers et al. |
| 7,780,619 B2 | 8/2010 | Brugger et al. |
| 7,798,997 B2 | 9/2010 | Kamen et al. |
| 7,892,331 B2 | 2/2011 | Childers et al. |
| 7,909,795 B2 | 3/2011 | Childers et al. |
| 7,935,074 B2 | 5/2011 | Plahey et al. |
| 7,955,295 B2 | 6/2011 | Lee et al. |
| 8,038,639 B2 | 10/2011 | Lo et al. |
| 8,105,265 B2 | 1/2012 | Demers et al. |
| 8,137,553 B2 | 3/2012 | Fulkerson et al. |
| 8,197,439 B2 | 6/2012 | Wang et al. |
| 8,251,953 B2 | 8/2012 | Kamen et al. |
| 8,330,579 B2 | 12/2012 | Kneip et al. |
| 8,366,316 B2 | 2/2013 | Kamen et al. |
| 8,366,655 B2 | 2/2013 | Kamen et al. |
| 8,496,609 B2 | 7/2013 | Childers et al. |
| 8,512,553 B2 | 8/2013 | Cicchello et al. |
| 8,535,525 B2 | 9/2013 | Heyes et al. |
| 8,673,139 B2 | 3/2014 | Hedmann et al. |
| 8,708,950 B2 | 4/2014 | Scarpaci et al. |
| 8,764,702 B2 | 7/2014 | Childers et al. |
| 8,803,044 B2 | 8/2014 | Kienman et al. |
| 8,840,581 B2 | 9/2014 | McGill et al. |
| 8,858,787 B2 | 10/2014 | Muller et al. |
| 8,870,811 B2 | 10/2014 | Gavin et al. |
| 9,022,969 B2 | 5/2015 | Helmore et al. |
| 9,028,440 B2 | 5/2015 | Helmore et al. |
| 9,078,971 B2 | 7/2015 | Scarpaci et al. |
| 9,121,403 B2 | 9/2015 | Lanigan et al. |
| 9,248,225 B2 | 2/2016 | Demers et al. |
| 9,302,039 B2 | 4/2016 | Kelly et al. |
| 9,358,332 B2 | 6/2016 | McGill et al. |
| 9,366,781 B2 | 6/2016 | Scarpaci et al. |
| 9,514,283 B2 | 12/2016 | Childers et al. |
| 9,593,679 B2 | 3/2017 | Gray et al. |
| 9,839,775 B2 | 12/2017 | McGill et al. |
| 9,839,776 B2 | 12/2017 | Helmore et al. |
| 9,861,732 B2 | 1/2018 | Scarpaci et al. |
| 9,981,079 B2 | 5/2018 | Scarpaci et al. |
| 9,987,410 B2 | 6/2018 | Helmore et al. |
| 10,058,694 B2 | 8/2018 | Norris et al. |
| 10,098,996 B2 | 10/2018 | Scarpaci et al. |
| 10,172,988 B2 | 1/2019 | McGill et al. |
| 10,195,330 B2 | 2/2019 | Coll et al. |
| 10,201,647 B2 | 2/2019 | Norris et al. |
| 10,265,451 B2 | 4/2019 | McGill et al. |
| 10,485,914 B2 | 11/2019 | Scarpaci et al. |
| 10,881,778 B2 | 1/2021 | Scarpaci et al. |
| 11,007,311 B2 | 5/2021 | Scarpaci et al. |
| 11,033,670 B2 | 6/2021 | Scarpaci et al. |
| 11,247,036 B2 | 2/2022 | Helmore et al. |
| 11,253,636 B2 | 2/2022 | McGill et al. |
| 11,364,329 B2 | 6/2022 | Demers et al. |
| 11,400,272 B2 | 8/2022 | Norris et al. |
| 11,478,577 B2 | 10/2022 | McGill et al. |
| 11,511,024 B2 | 11/2022 | McGill et al. |
| 11,598,329 B2 | 3/2023 | Grant et al. |
| 11,696,978 B2 | 7/2023 | Girouard et al. |
| 11,738,130 B2 | 8/2023 | Helmore et al. |
| 11,752,248 B2 | 9/2023 | Beavers et al. |
| 11,833,281 B2 | 12/2023 | McGill et al. |
| 11,964,086 B2 | 4/2024 | Scarpaci et al. |
| 11,975,128 B2 | 5/2024 | Demers et al. |
| 2003/0138334 A1 | 7/2003 | Vandlik et al. |
| 2003/0194332 A1 | 10/2003 | Jahn et al. |
| 2004/0243049 A1 | 12/2004 | Brugger et al. |
| 2005/0095141 A1 | 5/2005 | Lanigan et al. |
| 2005/0209563 A1 | 9/2005 | Hopping et al. |
| 2005/0234385 A1 | 10/2005 | Vandlik et al. |
| 2006/0084906 A1 | 4/2006 | Burbank et al. |
| 2006/0251533 A1 | 11/2006 | Nighy et al. |
| 2007/0077156 A1 | 4/2007 | Orr |
| 2007/0112297 A1 | 5/2007 | Plahey et al. |
| 2007/0135758 A1 | 6/2007 | Childers et al. |
| 2007/0140873 A1 | 6/2007 | Grapes |
| 2007/0278155 A1 | 12/2007 | Lo et al. |
| 2008/0033346 A1 | 2/2008 | Childers et al. |
| 2008/0077068 A1 | 3/2008 | Orr |
| 2008/0125693 A1 | 5/2008 | Gavin et al. |
| 2008/0132828 A1 | 6/2008 | Howard |
| 2008/0138223 A1 | 6/2008 | Lanigan et al. |
| 2008/0161751 A1 | 7/2008 | Plahey et al. |
| 2008/0203023 A1 | 8/2008 | Burbank et al. |
| 2008/0240929 A1 | 10/2008 | Kamen et al. |
| 2009/0012450 A1 | 1/2009 | Shah et al. |
| 2009/0012460 A1 | 1/2009 | Steck et al. |
| 2009/0107902 A1 | 4/2009 | Childers et al. |
| 2009/0113335 A1 | 4/2009 | Sandoe et al. |
| 2009/0124963 A1 | 5/2009 | Hogard et al. |
| 2009/0137940 A1 | 5/2009 | Orr |
| 2009/0294359 A1 | 12/2009 | Hopping et al. |
| 2010/0116740 A1 | 5/2010 | Fulkerson et al. |
| 2010/0191180 A1 | 7/2010 | Childers et al. |
| 2010/0191181 A1 | 7/2010 | Childers et al. |
| 2011/0092894 A1 | 4/2011 | McGill et al. |
| 2013/0165847 A1 | 6/2013 | Scarpaci et al. |
| 2013/0184638 A1 | 7/2013 | Scarpaci et al. |
| 2014/0194820 A1 | 7/2014 | Gray et al. |
| 2014/0364800 A1 | 12/2014 | McGill et al. |
| 2015/0359956 A1 | 12/2015 | Gray et al. |
| 2016/0030657 A1 | 2/2016 | Kelly et al. |
| 2016/0144093 A1 | 5/2016 | Demers et al. |
| 2019/0060629 A1 | 2/2019 | Norris et al. |
| 2019/0167883 A1 | 6/2019 | Girouard et al. |
| 2019/0314565 A1 | 10/2019 | McGill et al. |
| 2019/0321535 A1 | 10/2019 | Beavers et al. |

(56) References Cited

U.S. PATENT DOCUMENTS

| | | |
|---|---|---|
| 2019/0344002 A1 | 11/2019 | McGill et al. |
| 2021/0228793 A1 | 7/2021 | Scarpaci et al. |
| 2021/0275735 A1 | 9/2021 | Scarpaci et al. |
| 2022/0233754 A1 | 7/2022 | McGill et al. |
| 2022/0249755 A1 | 8/2022 | Helmore et al. |
| 2022/0280706 A1 | 9/2022 | Demers et al. |
| 2022/0282721 A1 | 9/2022 | Grant et al. |
| 2022/0412907 A1 | 12/2022 | Khosravi et al. |
| 2023/0390472 A1 | 12/2023 | Beavers et al. |
| 2024/0024547 A1 | 1/2024 | Helmore et al. |
| 2024/0157036 A1 | 5/2024 | McGill et al. |

FOREIGN PATENT DOCUMENTS

| | | |
|---|---|---|
| EP | 0 815 882 A2 | 1/1998 |
| EP | 1 195 171 A2 | 4/2002 |
| JP | 2000-167040 A | 6/2000 |
| JP | 2002-113096 A | 4/2002 |
| JP | 2003-000706 A | 1/2003 |
| JP | 2003-180825 A | 7/2003 |
| JP | 2007-097746 A | 4/2007 |
| WO | WO 84/02473 A1 | 7/1984 |
| WO | WO 96/25214 A1 | 8/1996 |
| WO | WO 98/39058 A1 | 9/1998 |
| WO | WO 99/10028 A1 | 3/1999 |
| WO | WO 01/17607 A1 | 3/2001 |
| WO | WO 01/18396 A1 | 3/2001 |
| WO | WO 01/19430 A1 | 3/2001 |
| WO | WO 2001/037895 A2 | 5/2001 |
| WO | WO 02/03879 A1 | 1/2002 |
| WO | WO 03/099353 A2 | 12/2003 |
| WO | WO 03/101510 A1 | 12/2003 |
| WO | WO 2005/044435 A2 | 5/2005 |
| WO | WO 2006/120415 A1 | 11/2006 |
| WO | WO 2009/006498 A2 | 1/2009 |

OTHER PUBLICATIONS

[No Author Listed], Patient At-Home Guide, HomeChoice Automated PD System. Version 2.0 (published May 1997); Baxter Healthcare Corporation. Copyright 1994. 61 pages.

Office Action for CA Application No. 2712953 filed Jan. 23, 2009, which Office Action is dated Dec. 8, 2015, and claims as pending for CA Application No. 2712953 as of Dec. 8, 2015.

Office Action for CA Application No. 2712953 filed Jan. 23, 2009, which Office Action is dated Oct. 12, 2016, and claims as pending for CA Application No. 2712953 as of Oct. 12, 2016.

Office Action for EP 09703430.0 mailed May 3, 2012 and claims pending as of May 3, 2012.

Response to Communication dated May 3, 2012 for EP Application No. 09703430.0 filed Jan. 23, 2009, which Response is dated Nov. 13, 2012, and claims as pending for EP Application No. 09703430.0 as of Nov. 13, 2012.

Examination Report for EP Application No. 09703430.0 filed Jan. 23, 2009, published as EP 2252346 on Nov. 24, 2010, which Examination Report is dated Apr. 24, 2014, and claims as pending for EP Application No. 09703430.0 as of Apr. 24, 2014.

Examination Report for EP Application No. 16163503.2 filed Apr. 1, 2016, published as EP 3061475 on Aug. 31, 2016, which Examination Report is dated Apr. 5, 2018, and claims as pending for EP Application No. 16163503.2 as of Apr. 5, 2018.

Office Action for JP Application No. 2010-544343 filed Jan. 23, 2009, published as JP 2011-509804 on Mar. 31, 2011, which Office Action is dated Apr. 2, 2013, and claims as pending for JP Application No. 2010-544343 as of Apr. 2, 2013.

Office Action for JP Application No. 2010-544343 filed Jan. 23, 2009, published as JP 2011-509804 on Mar. 31, 2011, which Office Action is dated Oct. 15, 2013, and claims as pending for JP Application No. 2010-544343 as of Oct. 15, 2013.

Office Action for JP Application No. 2014-160303 filed Aug. 6, 2014, Unpublished as of Jul. 1, 2015, which Office Action is dated Jul. 1, 2015, and claims as pending for JP Application No. 2014-16030 as of Jul. 1, 2015.

Office Action for JP Application No. 2016-046792 filed Mar. 10, 2016, unpublished as of Jan. 11, 2017, which Office Action is dated Jan. 11, 2017, and claims as pending for JP Application No. 2016-046792 as of Jan. 11, 2017.

Office Action for MX Application No. MX/A/2010/008016 filed Jan. 23, 2009, Unpublished as of Apr. 20, 2015, which Office Action is dated Apr. 20, 2015, and claims as pending for MX Application No. MX/A/2010/008016 as of Apr. 20, 2015.

Invitation to Pay Additional Fees for Application No. PCT/US2009/000441 mailed Jun. 24, 2009.

International Search Report and Written Opinion for Application No. PCT/US2009/000441 mailed Oct. 2, 2009.

International Preliminary Report on Patentability for Application No. PCT/US2009/000441 mailed Aug. 5, 2010.

Extended European Search Report for EP Application No. 16163503.2 filed Apr. 1, 2016, which Extended European Search Report is dated May 20, 2016, and claims as pending for EP Application No. 16163503.2 as of May 20, 2016.

Extended European Search Report for EP Application No. 19207114.0 filed Jan. 23, 2009, which Search Report is dated Mar. 18, 2020, and claims as pending for EP Application No. 19207114.0 as of Mar. 18, 2020.

Extended European Search Report for EP Application No. 23201814.3 dated Feb. 6, 2024 and claims pending as of Feb. 6, 2024.

Scarpaci et al., Medical Treatment System and Methods Using a Plurality of Fluid Lines. U.S. Appl. No. 18/621,949, filed Mar. 29, 2024.

Demers et al., Medical Treatment System and Methods Using a Plurality of Fluid Lines. U.S. Appl. No. 18/618,433, filed Mar. 27, 2024.

Office Action for CA Application No. 3,171,180 dated Aug. 28, 2024 and claims pending as of Aug. 28, 2024.

DISPOSABLE COMPONENTS FOR FLUID LINE AUTOCONNECT SYSTEMS AND METHODS

RELATED APPLICATIONS

This application is a continuation of U.S. patent application Ser. No. 16/207,349, filed Dec. 3, 2018, and issued on Feb. 22, 2022 as U.S. Pat. No. 11,253,636, which is a continuation of U.S. patent application Ser. No. 15/837,182, filed Dec. 11, 2017, and issued on Jan. 8, 2019 as U.S. Pat. No. 10,172,988, which is a continuation of U.S. patent application Ser. No. 14/466,437, filed Aug. 22, 2014, and issued on Dec. 12, 2017 as U.S. Pat. No. 9,839,775, which is a continuation of U.S. patent application Ser. No. 12/864,322, filed Dec. 20, 2010, and issued on Sep. 23, 2014 as U.S. Pat. No. 8,840,581, which is a National Stage of International Application Serial No. PCT/US2009/000441, filed Jan. 23, 2009, which claims the benefit under 35 U.S.C. § 119(e) of U.S. Provisional Application Ser. No. 61/011,967, filed Jan. 23, 2008 and U.S. Provisional Application Ser. No. 61/058,469, filed Jun. 3, 2008, each of which is incorporated herein in its entirety.

The following applications may have related subject matter: U.S. application Ser. No. 12/864,357 filed on Dec. 13, 2010; U.S. application Ser. No. 12/864,378 filed on Dec. 9, 2010; U.S. application Ser. No. 12/864,391 filed on Dec. 3, 2010; U.S. application Ser. No. 12/864,287 filed on Dec. 17, 2010; and U.S. application Ser. No. 12/864,293 filed Dec. 9, 2010.

BACKGROUND

Peritoneal Dialysis (PD) involves the periodic infusion of sterile aqueous solution (called peritoneal dialysis solution, or dialysate) into the peritoneal cavity of a patient. Diffusion and osmosis exchanges take place between the solution and the bloodstream across the natural body membranes. These exchanges transfer waste products to the dialysate that the kidneys normally excrete. The waste products typically consist of solutes like sodium and chloride ions, and other compounds normally excreted through the kidneys like urea, creatinine, and water. The diffusion of water across the peritoneal membrane during dialysis is called ultrafiltration.

Conventional peritoneal dialysis solutions include dextrose in concentrations sufficient to generate the necessary osmotic pressure to remove water from the patient through ultrafiltration.

Continuous Ambulatory Peritoneal Dialysis (CAPD) is a popular form of PD. A patient performs CAPD manually about four times a day. During a drain/fill procedure for CAPD, the patient initially drains spent peritoneal dialysis solution from his/her peritoneal cavity, and then infuses fresh peritoneal dialysis solution into his/her peritoneal cavity. This drain and fill procedure usually takes about 1 hour.

Automated Peritoneal Dialysis (APD) is another popular form of PD. APD uses a machine, called a cycler, to automatically infuse, dwell, and drain peritoneal dialysis solution to and from the patient's peritoneal cavity. APD is particularly attractive to a PD patient, because it can be performed at night while the patient is asleep. This frees the patient from the day-to-day demands of CAPD during his/her waking and working hours.

The APD sequence typically lasts for several hours. It often begins with an initial drain phase to empty the peritoneal cavity of spent dialysate. The APD sequence then proceeds through a succession of fill, dwell, and drain phases that follow one after the other. Each fill/dwell/drain sequence is called a cycle.

During the fill phase, the cycler transfers a predetermined volume of fresh, warmed dialysate into the peritoneal cavity of the patient. The dialysate remains (or "dwells") within the peritoneal cavity for a period of time. This is called the dwell phase. During the drain phase, the cycler removes the spent dialysate from the peritoneal cavity.

The number of fill/dwell/drain cycles that are required during a given APD session depends upon the total volume of dialysate prescribed for the patient's APD regimen, and is either entered as part of the treatment prescription or calculated by the cycler.

APD can be and is practiced in different ways.

Continuous Cycling Peritoneal Dialysis (CCPD) is one commonly used APD modality. During each fill/dwell/drain phase of CCPD, the cycler infuses a prescribed volume of dialysate. After a prescribed dwell period, the cycler completely drains this liquid volume from the patient, leaving the peritoneal cavity empty, or "dry." Typically, CCPD employs 4-8 fill/dwell/drain cycles to achieve a prescribed therapy volume.

After the last prescribed fill/dwell/drain cycle in CCPD, the cycler infuses a final fill volume. The final fill volume dwells in the patient for an extended period of time. It is drained either at the onset of the next CCPD session in the evening, or during a mid-day exchange. The final fill volume can contain a different concentration of dextrose than the fill volume of the successive CCPD fill/dwell/drain fill cycles the cycler provides.

Intermittent Peritoneal Dialysis (IPD) is another APD modality. IPD is typically used in acute situations, when a patient suddenly enters dialysis therapy. IPD can also be used when a patient requires PD, but cannot undertake the responsibilities of CAPD or otherwise do it at home.

Like CCPD, IPD involves a series of fill/dwell/drain cycles. Unlike CCPD, IPD does not include a final fill phase. In IPD, the patient's peritoneal cavity is left free of dialysate (or "dry") in between APD therapy sessions.

Tidal Peritoneal Dialysis (TPD) is another APD modality. Like CCPD, TPD includes a series of fill/dwell/drain cycles. Unlike CCPD, TPD does not completely drain dialysate from the peritoneal cavity during each drain phase. Instead, TPD establishes a base volume during the first fill phase and drains only a portion of this volume during the first drain phase. Subsequent fill/dwell/drain cycles infuse and then drain a replacement volume on top of the base volume. The last drain phase removes all dialysate from the peritoneal cavity.

There is a variation of TPD that includes cycles during which the patient is completely drained and infused with a new full base volume of dialysis.

TPD can include a final fill cycle, like CCPD. Alternatively, TPD can avoid the final fill cycle, like IPD.

APD offers flexibility and quality of life enhancements to a person requiring dialysis. APD can free the patient from the fatigue and inconvenience that the day to day practice of CAPD represents to some individuals. APD can give back to the patient his or her waking and working hours free of the need to conduct dialysis exchanges.

Still, the complexity and size of past machines and associated disposables for various APD modalities have dampened widespread patient acceptance of APD as an alternative to manual peritoneal dialysis methods.

SUMMARY OF INVENTION

Aspects of the invention relate to various components, systems and methods for use in medical applications, including medical infusion operations such as peritoneal dialysis. In some cases, aspects of the invention are limited to applications in peritoneal dialysis, while others to more general dialysis applications (e.g., hemodialysis) or infusion applications, while others to more general methods or processes. Thus, aspects of the invention are not necessarily limited to APD systems and methods, although many of the illustrative embodiments described relate to APD.

In one aspect of the invention, a disposable fluid handling cassette, such as that useable with an APD cycler device or other infusion apparatus, includes a generally planar body having at least one pump chamber formed as a depression in a first side of the body and a plurality of flowpaths for fluid that includes a channel. A patient line port may be arranged for connection to a patient line and be in fluid communication with the at least one pump chamber via at least one flowpath, and a membrane may be attached to the first side of the body over the at least one pump chamber. In one embodiment, the membrane may have a pump chamber portion with an unstressed shape that generally conforms to the pump chamber depression in the body and is arranged to be movable for movement of fluid in the useable space of the pump chamber. If the cassette body include two or more pump chamber depressions, the membrane may likewise include two or more pre-shaped pump portions. In other embodiments, the membrane need not be included with the cassette, e.g., where a control surface of the cycler interacts with the cassette to control pumping and/or valve functions.

In another embodiment, the pump chamber may include one or more spacer elements that extend from an inner wall of the depression, e.g., to help prevent the membrane from contacting the inner wall, thereby preventing blocking of an inlet/outlet of the pump chamber, helping remove or trap air in the pump chamber, and/or preventing sticking of the membrane to the inner wall. The spacer elements may be arranged to minimize deformation of the membrane at edges of the spacer elements when the membrane is forced against the spacer elements.

In another embodiment, a patient line port and a drain line port may be located at a first end of the body and be in fluid communication with the at least one pump chamber via at least one flowpath. A plurality of solution line spikes may, on the other hand, be located at a second end of the body opposite the first end, with each of the solution line spikes being in fluid communication with the at least one pump chamber via at least one flowpath. This arrangement may enable automated connection of solution lines to the cassette, and/or separate occlusion of the patient and/or drain lines relative to the solution lines. In one embodiment, a heater bag line port may also be located at the first end of the body and be in fluid communication with the at least one pump chamber via at least one flowpath. Flexible patient, drain and heater bag lines may be respectively connected to the patient line port, drain line port and heater bag line port.

In another embodiment, the body may include a vacuum vent clearance depression formed adjacent the at least one pump chamber. This depression may aid in the removal of fluid (gas and/or liquid) between the membrane and a corresponding control surface of the cycler, e.g., by way of a vacuum port in the control surface. That is, the depression may help ensure that the membrane is not forced against the vacuum port, leaving the port open to draw fluid into a collection chamber as necessary.

In one embodiment, one or more ports, such as a drain line port and heater bag line port, and/or one or more solution line spikes may communicate with a common flowpath channel of the cassette base. As needed, a plurality of valves may each be arranged to control flow in a respective flowpath between the at least one pump chamber and the patient line port, the drain line port, and the plurality of solution line spikes. In one embodiment, portions of the membrane may be positioned over respective valves and be movable to open and close the respective valve. Similarly, flow through openings into the pump chamber(s) may be controlled by corresponding valves that are opened and closed by movement of one or more portions of the membrane.

In some embodiments, the membrane may close at least some of the flowpaths of the body. That is, the body may be formed with open flow channels that are closed on at least one side by the membrane. In one embodiment, the body may include flowpaths formed on opposite planar sides, and at least some of the flowpaths on a first side may communicate with flowpaths on the second side.

In one embodiment, one or more spikes on the cassette (e.g., for receiving dialysate solution) may be covered by a spike cap that seals the spike closed and is removable.

In another aspect of the invention, a disposable fluid handling cassette, for use with a reusable automated peritoneal dialysis cycler device, includes a generally planar body having at least one pump chamber formed as a depression in a first side of the body and a plurality of flowpaths for fluid that includes a channel, a patient line port arranged for connection to a patient line, the patient line port being in fluid communication with the at least one pump chamber via at least one flowpath, and a flexible membrane attached to the first side of the body over the at least one pump chamber. A pump chamber portion of the membrane over the at least one pump chamber may have an unstressed shape that generally conforms to usable area of the pump chamber depression in the body and be arranged to be movable for movement of fluid in the pump chamber. In one embodiment, the cassette is configured for operative engagement with a reusable automated peritoneal dialysis cycler device.

The cassette may include a drain line port arranged for connection to a drain line, the drain line port being in fluid communication with the at least one pump chamber via at least one flowpath, and/or a plurality of solution line spikes that are in fluid communication with the at least one pump chamber via at least one flowpath. The pump chamber portion of the membrane may be generally dome shaped, and may include two pump chamber portions that have a shape that generally conforms to usable area of a corresponding pump chamber depression. In one embodiment, a volume of the pump chamber portion may be between 85-110% of the useable volume of the pump chamber depression. In another embodiment, the pump chamber portion may be arranged to be 85-110% of the depth of the useable area of the pump chamber depression. In another embodiment, the pump chamber portion may be arranged to have a size that is between 85-100% of the circumference of the useable area of the pump chamber depression. The useable area of the pump chamber may be defined at least in part by one or more spacer elements that extend from an inner wall of the depression. In one embodiment, a plurality of spacer elements may be of graduated lengths or varying height that define a generally dome-shaped region or other shape. The spacer elements may be arranged in a concentric elliptical pattern or other shape when viewed in plan. One or more breaks in the pattern may be provided, e.g., to allow communication between voids. In one embodiment, the spacer elements may be arranged to minimize deformation of the membrane at edges of the spacer elements when the membrane is forced against the spacer elements. In another embodiment, one or more spacers may be configured to inhibit the membrane from covering the fluid inlet and/or outlet of the pump chamber.

In another aspect of the invention, a fluid handling cassette for use with a fluid handling system of a medical infusion device includes a generally planar body having at least one pump chamber formed as a depression in a first side of the body and a plurality of flowpaths for fluid that includes a channel, the at least one pump chamber including one or more spacer elements that extend from an inner wall of the depression, a patient line port arranged for connection to a patient line, the patient line port being in fluid communication with the at least one pump chamber via at least one flowpath, a drain line port arranged for connection to a drain line, the drain line port being in fluid communication with the at least one pump chamber via at least one flowpath, and a plurality of solution line spikes being in fluid communication with the at least one pump chamber via at least one flowpath.

In one aspect of the invention, a disposable component system for use with a fluid line connection system of a peritoneal dialysis system includes a fluid handling cassette having a generally planar body with at least one pump chamber formed as a depression in a first side of the body and a plurality of flowpaths for fluid, a solution line spike located at a first end of the body, the solution line spike being in fluid communication with the at least one pump chamber via at least one flowpath, and a spike cap configured to removably cover the solution line spike, wherein the cap includes at least one raised feature (e.g., an asymmetrical or symmetrical flange) to aid in removal of the cap for connection to a solution line prior to the commencement of a peritoneal dialysis therapy.

In one embodiment, the cassette includes a skirt arranged around the spike to receive the end of the spike cap, and there may be a recess between the skirt and the spike that are arranged to aid in forming a seal between the spike cap and skirt.

In another embodiment, a solution line cap may be removably connected to a solution line, and the solution line cap may include a recessed feature (such as a symmetrical or asymmetrical groove). At least a portion of the solution line cap may include a flexible material, such as silicone rubber. The recessed feature may aid in the removal of a spike cap from the cassette.

In another embodiment, the spike cap includes a second raised feature that may function as a stop for the solution line cap.

In another embodiment, a main axis of one or more spikes is in substantially a same plane as the generally planar body of the fluid handling cassette.

In another aspect of the invention, a fluid handling cassette for use with a peritoneal dialysis system includes a generally planar body with at least one pump chamber formed as a depression in a first side of the body and a plurality of flowpaths for fluid, and a spike located at a first end of the body for engagement with a dialysate solution line. The spike may be in fluid communication with the at least one pump chamber via at least one flowpath and include a distal tip and a lumen arranged so that the distal tip of the spike is positioned substantially near the longitudinal axis of the spike. In one embodiment, the lumen may be positioned substantially off the longitudinal axis.

In another aspect of the invention, a disposable component system for use with a fluid line connection system of a peritoneal dialysis system includes a spike cap configured to removably cover a spike of a fluid handling cassette. The cap may include at least one feature to aid in removal of the cap for connection to a solution line prior to the commencement of a peritoneal dialysis therapy. The feature may be a raised feature, or a recessed feature, and may be configured for engagement with a solution line cap.

In another aspect of the invention, a disposable component system for use with a fluid line connection system of a peritoneal dialysis system includes a solution line cap for removable attachment to a solution line, wherein the solution line cap includes at least one feature to aid in removal of a spike cap to enable connection between a solution line and a spike prior to the commencement of a peritoneal dialysis therapy. The feature may be a raised feature, or a recessed feature, and may be configured for engagement with a spike cap. Indicia may e associated with a solution line, e.g., so that a solution associated with the line may be identified and affect at least one function of the peritoneal dialysis system.

In another aspect of the invention, a medical infusion fluid handling system, such as an APD system, may be arranged to de-cap and connect one or more lines (such as solution lines) with one or more spikes or other connection ports on a fluid handling cassette. This feature may provide advantages, such as a reduced likelihood of contamination since no human interaction is required to de-cap and connect the lines and spikes. For example, an APD system may include a carriage arranged to receive a plurality of solution lines each having a connector end and a cap. The carriage may be arranged to move along a first direction so as to move the connector ends of the solution lines along the first direction, and a cap stripper may be arranged to engage with caps on the solution lines on the carriage. The cap stripper may be arranged to move in a second direction transverse to the first direction, as well as to move with the carriage along the first direction. For example, the carriage may move toward a cassette in an APD cycler in a first direction so as to engage caps on the solution lines with caps on spikes of the cassette. The cap stripper may engage the caps (e.g., by moving in a direction transverse to the motion of the carriage) and then move with the carriage as the carriage pulls away from the cassette to remove the caps from the spikes. The carriage may then pull the connector ends of the solution lines from the caps on the cap stripper, which may retract to allow the carriage to engage the now exposed solution line connector ends with the exposed spikes on the cassette.

In one embodiment, the carriage may include a plurality of grooves that each receive a corresponding solution line. By positioning solution lines in corresponding grooves, each of the lines may be more easily individually identified, e.g., by reading a barcode or other identifier on the line, and controlling the system accordingly. The carriage may be mounted to a door of a cycler housing, and a carriage drive may move the carriage along the first direction. In one embodiment, the carriage drive may engage the carriage when the door is moved to a closed position, and disengage from the carriage when the door is moved to an open position.

In one embodiment, the cap stripper may include a plurality of fork-shaped elements arranged to engage with a corresponding cap on a solution line carried by the carriage. The fork-shaped elements may hold the caps when they are removed from the solution lines, and each of the solution line caps may itself hold a spike cap. In another embodiment, the cap stripper may include a plurality of rocker arms each associated with a fork-shaped element. Each of the rocker arms may be arranged to move to engage a spike cap, e.g., to assist in removing the spike cap from the corresponding spike. Each of the rocker arms may be arranged to engage with a corresponding spike cap only when the associated fork-shaped element engages with a cap on a solution line. Thus, the cap stripper may not engage or remove spike caps from the cassette in locations where there is no corresponding solution line to connect with the spike.

In another aspect of the invention, a method for connecting fluid lines in a medical infusion fluid handling system, such as an APD cycler, may involve locating solution lines and spikes of a cassette in an enclosed space away from human touch. The solution lines and/or spikes may have caps removed and the lines connected to spikes while in the enclosed space, thus providing the connection while minimizing potential contamination at the connection, e.g., by fingers carrying pathogens or other potentially harmful substances. For example, one method in accordance with this aspect of the invention includes providing a plurality of solution lines each having a connector end and a cap, providing a fluid handling cassette having a plurality of spikes each covered by a spike cap, enclosing the connector ends of the plurality of solution lines with caps covering the connector ends and the plurality of spikes with spike caps covering the spikes in a space that prevents human touch of the caps or spike caps, removing the caps from the connector ends of the plurality of solution lines without removing the caps or connector ends from the space, removing the spike caps from the spikes without removing the spike caps or spikes from the space, engaging the caps with respective ones of the spike caps, and fluidly connecting the plurality of connector ends to corresponding spikes while maintaining the connector ends and spikes in the space and protected from human touch.

In one embodiment, the solution line caps and spike caps may be engaged with each other before their removal from the lines or spikes, and then may be removed from both the lines and the spikes while engaged with each other. This technique may simplify the de-capping/capping process, as well as allow for easier storage of the caps.

In another embodiment, the solution lines may be disconnected from the spikes, and the connector ends of the lines and the spikes may be re-capped, e.g., after a treatment is completed.

In another aspect of the invention, a dialysis machine may include a fluid handling cassette having a plurality of spikes and a plurality of spike caps covering a respective spike, a plurality of solution lines each having a cap covering a connector end of the respective line, and a cap stripper arranged to remove one or more caps from a connector end of a solution line, and remove one or more spike caps from a spike on the cassette while the one or more caps are secured to a corresponding one of the spike caps. As discussed above, the machine may be arranged to automatically fluidly connect a connector end of a solution line with a corresponding spike after the caps are removed.

In another aspect of the invention, a dialysis machine, such as an APD system, may include a cassette having a plurality of fluid spikes and a plurality of spike caps covering a respective spike, a carriage arranged to receive a plurality of solution lines each having a cap covering a connector end of the respective line, and a cap stripper arranged to engage one or more caps covering a connector end of a line. The carriage and cap stripper may be configured to engage one or more caps on a connector end of a line while the one or more caps are engaged with a corresponding spike cap covering a spike on the cassette, and to remove the spike cap from the spike and the cap from the connector end of the solution line, and to fluidly connect the spike and the connector end of the solution line after the caps are removed.

In another aspect of the invention, a dialysis machine may include a cap stripper that is arranged to remove one or more caps on a connector end of a solution line, remove one or more spike caps from spikes on a fluid handling cassette, and to retain and reattach the caps to the solution lines and the spike caps to the spikes on the cassette.

In another aspect of the invention, a fluid line connection system for a peritoneal dialysis system includes a fluid handling cassette having a generally planar body with at least one pump chamber formed as a depression in a first side of the body and a plurality of flowpaths for fluid, a plurality of dialysate solution line spikes located at a first end of the body, the solution line spikes being in fluid communication with the at least one pump chamber via at least one flowpath and arranged so that the spikes are generally co-planar with the generally planar body of the fluid handing cassette, and a carriage arranged to receive a plurality of solution lines, where each solution line has a connector end. The carriage may be arranged to automatically fluidly connect a connector end of a solution line with a corresponding spike.

In one embodiment, the carriage is arranged to move the solution lines and respective caps along a first direction substantially parallel to the generally planar body of the fluid handling cassette. A carriage drive that moves the carriage only the first direction may include a drive element and a pneumatic bladder or screw drive to move the drive element along the first direction. A cap stripper may be provided that is arranged to remove one or more caps from a connector end of a solution line, and remove one or more spike caps from a spike on the cassette while the one or more caps are secured to a corresponding one of the spike caps. In one embodiment, the cap stripper may be arranged to r retain and reattach the caps to the solution lines and the spike caps to the spikes on the cassette.

In another aspect of the invention, a peritoneal dialysis system may include a cycler device with components suitable for controlling delivery of dialysate to the peritoneal cavity of a patient. The cycler device may have a housing that encloses at least some of the components and have a heater bag receiving section. (The term "heater bag" is used herein to refer to any suitable container to heat dialysate, such as a flexible or rigid container, whether made of polymer, metal or other suitable material.) A lid may be mounted to the housing and be movable between an open position in which a heater bag is placeable in the heater bag receiving section and a closed position in which the lid covers the heater bag receiving section. Such an arrangement may allow for faster or more efficient heating of dialysate in the heater bag, e.g., because heat may be retained by the lid. Also, the lid may help prevent human touch of potentially hot surfaces.

In on embodiment, the dialysis system may include a fluid handling cassette with a heater bag port attached to a heater bag line, a patient port attached to a patient line, and at least one pump chamber to move fluid in the patient line and the heater bag line. A heater bag may be attached to the heater bag line and be arranged for placement in the heater bag receiving section.

In another embodiment, the system may include an interface (such as a visual display with a touch screen component) that is movably mounted to the housing and is movable between a first position in which the interface is received in the heater bag receiving section, and a second position in which the interface is located out of the heater bag receiving section (e.g., a position in which a user may interact with the interface). Thus, the interface may be hidden from view when the system is idle, allowing the interface to be protected. Also, storing the interface in the heater bag receiving section may make the system more compact, at least in an "as stored" condition.

In another aspect of the invention, a dialysis system includes a supply of pneumatic pressure and/or vacuum suitable for controlling pneumatically-operated components of the system, a pneumatically-operated component that is fluidly connected to the supply of pneumatic pressure and/or vacuum, and a control system that provides pneumatic pressure or vacuum to the pneumatically-operated component and subsequently isolates the pneumatically-operated component from the supply of pneumatic pressure or vacuum for a substantial period of time before again providing pneumatic pressure or vacuum to the pneumatically-operated component. Such an arrangement may be useful for components that are actuated relatively infrequently, such as the occluder arrangement described herein. Small motions of some components may cause the component to emit noise that may be found bothersome by a patient. By isolating the component from the pneumatic pressure/vacuum, the component may avoid slight movement caused by variations in the supply pressure/vacuum, e.g., resulting from draws on the pressure/vacuum by other system components. In one embodiment, the substantial period of time may be 5 minutes or more, 1 hour or more, 50% or more of a time period required to deliver or remove a volume of dialysate suitable for a dialysis treatment with respect to a patient's peritoneal cavity, or other suitable periods.

In another aspect of the invention, a dialysis system includes a supply of pneumatic pressure and/or vacuum suitable for controlling pneumatically-operated components of the system, a pneumatically-operated component that is fluidly connected to the supply of pneumatic pressure and/or vacuum, and a control system that provides pneumatic pressure or vacuum to the pneumatically-operated component and controls the pneumatic pressure or vacuum so as to reduce noise generated by the pneumatically-operated component. For example, the pneumatically-operated component may include at least one moving part (such as a pump diaphragm), and the control system may reduce the pneumatic pressure or vacuum provided to the pneumatically-operated component so as to slow movement of the moving part as the moving part stops and/or changes direction (e.g., the pressure/vacuum may be controlled to slow movement of the diaphragm before the diaphragm changes direction). In another embodiment, a pulse width modulation control of a pressure/vacuum supply valve may be used, e.g., to reduce noise emitted by moving parts of the valve.

In another aspect of the invention, a dialysis system includes a supply of pneumatic pressure and vacuum suitable for controlling pneumatically-operated components of the system. A first pneumatically-operated component may be fluidly connected to the supply of pneumatic pressure and/or vacuum, and have a first output line to release pneumatic pressure. A second pneumatically-operated component may be fluidly connected to the supply of pneumatic pressure and/or vacuum, and have a second output line to release pneumatic vacuum. A space, such as that defined by an accumulator, manifold or sound-insulated chamber, may be fluidly connected to both the first and second output lines. A control system may provide pneumatic pressure or vacuum to the pneumatically-operated components so that when the first and second components release pressure/ vacuum during operation, the released pressure/vacuum may be received into the common space (e.g., a manifold). In some circumstances, gas under positive pressure released by components may be balanced by negative pressure released by other components, thus reducing noise generated.

In another aspect of the invention, a peritoneal dialysis system may include a fluid handling cassette having a patient line fluidly connected to and leading from the peritoneal cavity of a patient, and which includes at least one pump chamber to move dialysate solution in the patient line. A cycler device may be arranged to receive and interact with the fluid handling cassette and cause the at least one pump chamber to move dialysate solution in the patient line. The cycler may include a control system arranged to control the at least one pump chamber to operate in a priming operation to force dialysate solution into the patient line so as to remove any air in the patient line, and may be adapted to interact with two types of fluid handling cassettes that differ with respect to a volume of the patient line connected to the cassette body. A first type of cassette may have a relatively low volume patient line (e.g., for pediatric applications), and a second type of cassette may have a relatively high volume patient line (e.g., for adult applications), and the control system may detect whether a cassette received by the cycler is a first type or a second type and to adjust cycler operation accordingly.

In one embodiment, the control system may detect whether a cassette received by the cycler is a first type or a second type by determining the volume of the patient line during priming, and to adjust the amount of fluid moved through the cassette during operation of the system. In another embodiment, indicia, such as a barcode, on the cassette may be detected by the cycler and cause the cycler to adjust a pumping operation based on the type of cassette.

In another aspect of the invention, a dialysis machine includes a fluid handling cassette having a plurality of spikes and at least one pump chamber to move fluid in the spikes, a plurality of solution lines each engaged with a respective spike on the cassette, and a control system that reads indicia on each of the solution lines to determine a type for each of the solution lines. The control system may adjust a pumping operation or other cycler operation based in the identity of one or more of the solution lines. For example, a solution line may be identified as being an effluent sampling line and the pumping operation may be adjusted to direct used dialysate from a patient to the effluent sampling line during a drain cycle.

In another aspect of the invention, a method of automatically recovering from a tilt condition in a dialysis system may include (A) detecting an angle of tilt of at least a portion of a dialysis system, the portion of the dialysis system including machinery for performing a dialysis therapy, (B) determining that a tilt condition exists in which the angle of tilt exceeds a predetermined threshold, (C) in response to (B), pausing the dialysis therapy, (D) monitoring the angle of tilt while the dialysis therapy is paused, (E) determining that the tilt condition no longer exists, and (F) in response to (E), automatically resuming the dialysis therapy.

In another aspect of the invention, a patient data interface for a dialysis system includes a device port comprising a recess in a chassis of at least a portion of the dialysis system and a first connector disposed within the recess. A patient data storage device may include a housing and a second connector coupled to the housing, where the second connector is adapted to be selectively coupled to the first connector. The recess may have a first shape and the housing may have a second shape corresponding to the first shape such that when the first and second connectors are coupled, the housing of the patient data storage device is received at least partially within the recess. The first and second shapes may be irregular and the patient data storage device may have a verification code that is readable by the dialysis system to verify that the patient data storage device is of an expected type and/or origin.

In another aspect of the invention, a method for providing peritoneal dialysis includes delivering or withdrawing dialysate with respect to the patient's peritoneal cavity at a first pressure, and adjusting a pressure at which dialysate is delivered or withdrawn to minimize patient sensation of dialysate movement. In one embodiment, the pressure may be adjusted during a same fill or empty cycle of a peritoneal dialysis therapy, and/or within different fill or empty cycles of a peritoneal dialysis therapy. For example, when withdrawing dialysate from a patient, the pressure at which dialysate is withdrawn may be reduced when an amount of dialysate remaining in the peritoneal cavity drops below a threshold volume. Reducing the pressure (negative pressure or vacuum) near the end of a drain cycle may reduce the sensation the patient may have of the dialysate withdrawal.

In another aspect of the invention, a method for providing peritoneal dialysis includes providing a first solution to a patient's peritoneal cavity using a reusable cycler device during a first treatment of peritoneal dialysis, and providing a second solution to the patient's peritoneal cavity using the reusable cycler device during a second treatment of peritoneal dialysis immediately subsequent to the first treatment, where the second solution has a different chemical makeup relative to the first solution. The different solutions may be created by mixing liquid material from two or more solution containers that are connected to the cycler (e.g., via a cassette mounted to the cycler). The solution containers may be automatically identified by the cycler, e.g., by reading a barcode, RFID tag, or other indicia.

In another aspect of the invention, a medical infusion system includes a housing that encloses at least some of the components of the system, and a control surface attached to the housing and constructed and arranged to control the operation of a fluid handling cassette that may be removably mounted to the housing. The control surface may have a plurality of movable portions arranged to control fluid pumping and valve operations of the cassette, and at least one of the movable portions may have an associated vacuum port arranged to draw fluid from a region near the movable portion.

In one embodiment, the control surface includes a sheet of resilient polymer material, and each of the movable portions may have an associated vacuum port. In another embodiment, the cassette includes a membrane that is positionable adjacent the control surface, and the vacuum port is arranged to remove fluid from a space between the membrane and the control surface. A liquid sensor may be arranged to detect liquid drawn into the vacuum port, e.g., in case the membrane ruptures, allowing liquid to leak from the cassette.

In another aspect of the invention, a volume of fluid moved by a pump, such as a pump in an APD system, may be determined based on pressure measurement and certain known chamber and/or line volumes, but without direct measurement of the fluid, such as by flow meter, weight, etc. In one embodiment, a volume of a pump chamber having a movable element that varies the volume of the pump chamber may be determined by measuring pressure in the pump chamber, and a reference chamber both while isolated from each other, and after the two chambers are fluidly connected so that pressures in the chambers may equalize. In one embodiment, equalization of the pressures may be assumed to occur in an adiabatic way, e.g., a mathematical model of the system that is based on an adiabatic pressure equalization process may be used to determine the pump chamber volume. In another embodiment, pressures measured after the chambers are fluidly connected may be measured at a time before complete equalization has occurred, and thus the pressures for the pump and reference chambers measured after the chambers are fluidly connected may be unequal, yet still be used to determine the pump chamber volume. This approach may reduce a time between measurement of initial and final pressures, thus reducing a time during which heat transfer may take place and reducing error that may be introduced given the adiabatic model used to determine the pump chamber volume.

In one aspect of the invention, a method for determining a volume of fluid moved by a pump includes measuring a first pressure for a pump control chamber when the pump control chamber is isolated from a reference chamber. The pump control chamber may have a volume that varies at least in part based on movement of a portion of the pump, such as a pump membrane or diaphragm. A second pressure may be measured for the reference chamber when the reference chamber is isolated from the pump control chamber. The reference chamber may have a known volume. A third pressure associated with the pump control chamber after fluidly connecting the reference chamber and the pump control chamber may be measured, but the measurement may occur before substantial equalization of pressures between the pump control and reference chambers has occurred. Similarly, a fourth pressure associated with the reference chamber after fluidly connecting the reference chamber and the pump control chamber may be measured, but before substantial equalization of pressures between the pump control and reference chambers has occurred. A volume for the pump control chamber may be determined based on the first, second, third and fourth measured pressures.

In one embodiment, the third and fourth pressures are measured at approximately a same time and the third and fourth pressures are substantially unequal to each other. For example, equalization of the pressures in the pump control and reference chambers may occur after an equalization time period once the pump control and reference chambers are fluidly connected, but the third and fourth pressures may be measured at a time after the pump control and reference chambers are fluidly connected that is approximately 10% to 50% of the equalization time period. Thus, the third and fourth pressures may be measured long before (in time sense) the pressures in the chambers have fully equalized. In another embodiment, the third and fourth pressures may be measured at a time when the pressures in the chambers has reached approximately 50-70% equalization, e.g., the pressures in the chambers have changed from an initial value that is within about 50-70% of an equalized pressure value. Thus, a time period between measurement of the first and second pressures and measurement of the third and fourth pressures may be minimized.

In another embodiment, a model for determining the volume of the pump control chamber may incorporate an assumption that an adiabatic system exists from a point in time when the first and second pressures are measured for the isolated pump control chamber and the reference chamber until a point in time when the third and fourth pressures are measured.

To determine a volume of fluid moved by the pump, the steps of measuring the first, second, third and fourth pressures and the step of determining may be performed for two different positions of a pump membrane to determine two different volumes for the pump control chamber. A difference between the two different volumes may represent a volume of fluid delivered by the pump.

As mentioned above, this aspect of the invention may be used in any suitable system, such as a system in which the pump is part of a disposable cassette and the pump control chamber is part of a dialysis machine used in a dialysis procedure.

In one embodiment, the first and/or second pressure may be selected from a plurality of pressure measurements as coinciding with a point in time at which a pressure in the pump control chamber or reference chamber (as appropriate) first begins to change from a previously stable value. For example, the point in time may be identified based on a determination of when a best fit line for a plurality of consecutive sets of measured pressures first deviates from a constant slope. This approach may help identify initial pressures for the pump control and reference chambers that are as late in time as possible, while reducing error in the pump volume determination.

In another embodiment, a technique may be used to identify an optimal point in time at which the third and fourth pressures are measured. For example, a plurality of pressure values for the pump control chamber may be measured after the pump control and reference chambers are fluidly connected, and a plurality of change in volume values may be determined for the pump control chamber based on the plurality of pressure values for the pump control chamber. Each of the plurality of change in volume values may corresponding to a unique point in time and a measured pressure value for the pump chamber. In this case, the change in volume values are due to movement of an imaginary piston that is present at the valve or other component that initially isolates the pump control and reference chambers, but moves upon opening of the valve or other component. Thus, the pump chamber does not actually change size or volume, but rather the change in volume is an imaginary condition due to the pressures in the pump chamber and reference chamber being different from each other initially. Similarly, a plurality of pressure values for the reference chamber may be measured after the pump control and reference chambers are fluidly connected, and a plurality of change in volume values for the reference chamber may be determined based on the plurality of pressure values for the reference chamber. Each of the plurality of change in volume values may correspond to a unique point in time and a measured pressure value for the reference chamber, and like the change in volume values for the pump chamber, are a result of movement of an imaginary piston. A plurality of difference values between change in volume values for the pump control chamber and for the reference chamber may be determined, with each difference value being determined for corresponding change in volume values for the pump control chamber and change in volume values for the reference chamber, i.e., the pairs of change in volume values for which a difference value is determined correspond to a same or substantially same point in time. The difference values may be analyzed, and a minimum difference value (or a difference value that is below a desired threshold) may indicate a point in time for which the third and fourth pressures should be measured. Thus, the third and fourth pressure values may be identified as being equal to the pump control chamber pressure value and the reference chamber pressure value, respectively, that correspond to a difference value that is a minimum or below a threshold.

In another embodiment, the pressures measured are pressures of a gas within the pump control chamber and the reference chamber, the equalization of pressures within the pump control chamber and reference chamber is assumed to occur adiabatically, the equalization of pressures between the pump control chamber and reference chamber is assumed to include a change in the volume of a gas in the pump control chamber and reference chamber in equal but opposite directions, and the volume of gas in the reference chamber at the time of the fourth pressure measurement is calculated from the known volume of the reference chamber, and the second and fourth pressures. The change in volume of gas in the reference chamber may be assumed to be the difference between the known volume of the reference chamber and the calculated value of the volume of gas in the reference chamber at the time of the fourth pressure measurement. Also, the change in volume of gas in the pump control chamber may be assumed to be the difference between the initial volume of the pump control chamber and the volume of gas in the pump control chamber at the time of the third pressure measurement, wherein the change in volume of gas in the pump control chamber is equal to but opposite the change in volume of gas in the reference chamber.

In another aspect of the invention, a method for determining a volume of fluid moved by a pump includes providing a fluid pump apparatus having a pump chamber separated from a pump control chamber by a movable membrane, and a reference chamber that is fluidly connectable to the pump control chamber, adjusting a first pressure in the pump control chamber to cause the membrane to move and thereby move fluid in the pump chamber, isolating the reference chamber from the pump control chamber and establishing a second pressure in the reference chamber that is different from a pressure in the pump control chamber, fluidly connecting the reference chamber and the pump control chamber to initiate equalization of pressures in the pump control chamber and the reference chamber, and determining a volume for the pump control chamber based on the first and second pressures, and an assumption that the pressures in the pump control and reference chambers initiate equalization in an adiabatic way.

In one embodiment, third and fourth pressures for the pump control and reference chambers, respectively, may be measured after fluidly connecting the reference chamber and the pump control chamber, and the third and fourth pressures may be used to determine the volume for the pump control chamber. The third and fourth pressures may be substantially unequal to each other. Similar to that mentioned above, the adjusting, isolating, fluidly connecting and determining steps may be repeated, and a difference between the two determined volumes for the pump control chamber may be determined, where the difference represents a volume of fluid delivered by the pump.

In another embodiment, the pump is part of a disposable cassette and the pump control chamber is part of a dialysis machine used in a dialysis procedure.

In another aspect of the invention, a medical infusion system includes a pump control chamber, a control surface associated with the pump control chamber so that at least a portion of the control surface is movable in response to a pressure change in the pump control chamber, a fluid handling cassette having at least one pump chamber positioned adjacent the control surface and arranged so that fluid in the at least one pump chamber moves in response to movement of the portion of the control surface, a reference chamber that is fluidly connectable to the pump control chamber, and a control system arranged to adjust a pressure in the pump control chamber and thus control movement of fluid in the pump chamber of the fluid handling cassette. The control system may be arranged to measure a first pressure for the pump control chamber when the pump control chamber is isolated from the reference chamber, measure a second pressure for the reference chamber when the reference chamber is isolated from the pump control chamber, fluidly connect the pump control chamber and the reference chamber, measure third and fourth pressures associated with the pump control chamber and the reference chamber, respectively, after fluidly connecting the reference chamber and the pump control chamber, and determine a volume for the pump control chamber based on the first, second, third and fourth measured pressures and a mathematical model that defines equalization of pressure in the pump control and reference chambers as occurring adiabatically when the pump control and reference chambers are fluidly connected.

In one embodiment, the third and fourth pressures are substantially unequal to each other, e.g., the third and fourth pressures may be measured prior to substantial equalization of pressures in the pump control and reference chambers.

In another aspect of the invention, a method for determining a volume of fluid moved by a pump includes measuring a first pressure for a pump control chamber when the pump control chamber is isolated from a reference chamber, the pump control chamber having a volume that varies at least in part based on movement of a portion of the pump, measuring a second pressure for the reference chamber when the reference chamber is isolated from the pump control chamber, measuring a third pressure associated with both the pump control chamber and the reference chamber after fluidly connecting the reference chamber and the pump control chamber, and determining a volume for the pump control chamber based on the first, second and third measured pressures.

In one embodiment, the third pressure may be measured after complete equalization of pressures in the pump control and reference chambers is complete. In one embodiment, a model used to determine the pump chamber volume may assume an adiabatic system in equalization of pressure between the pump chamber and the reference chamber.

In one aspect of the invention, a method for determining a presence of air in a pump chamber includes measuring a pressure for a pump control chamber when the pump control chamber is isolated from a reference chamber, the pump control chamber having a known volume and being separated from a pump chamber, that is at least partially filled with liquid, by a membrane, measuring a pressure for the reference chamber when the reference chamber is isolated from the pump control chamber, the reference chamber having a known volume, measuring a pressure after fluidly connecting the reference chamber and the pump control chamber and prior to a time when the pressure in the chambers has equalized, and determining a presence or absence of an air bubble in the pump chamber based on the measured pressures and known volumes.

In one embodiment, a model used to determine the presence or absence of an air bubble assumes an adiabatic system from a point in time when the pressures are measured for the isolated pump control chamber and the reference chamber until a point in time after the chambers are fluidly connected. In another embodiment, the pressure for the pump control chamber is measured with the membrane drawn toward a wall of the pump control chamber.

In another aspect of the invention, an automated peritoneal dialysis system includes a reusable cycler that is constructed and arranged for coupling to a disposable fluid handling cassette containing at least one pumping chamber. The disposable fluid handling cassette may be configured to be connected in fluid communication with the peritoneum of a patient via a first collapsible tube and with a second source and/or destination (such as a solution container line) via a second collapsible tube. An occluder may be configured and positioned within the cycler to selectively occlude the first collapsible tube while not occluding the second collapsible tube. In one embodiment, the occluder can occlude a plurality of collapsible tubes, such as a patient line, a drain line and/or a heater bag line. The cassette may have a generally planar body with at least one pump chamber formed as a depression in a first side of the body and a plurality of flowpaths for fluid, a patient line port located at a first end of the body arranged for connection to the first collapsible tube, and a solution line port located at a second end of the body opposite the first end, and arranged for connection to the second collapsible tube. The occluder may be configured and positioned within the cycler to selectively occlude the first tube and a third collapsible tube (e.g., for a drain) while not occluding the second collapsible tube.

In another embodiment, the occluder includes first and second opposed occluding members pivotally connected to each other, a tube contacting member connected to, or comprising at least a portion of, at least one of the first and second occluding members, and a force actuator constructed and positioned to apply a force to at least one of the first and second occluding members. Application of the force by the force actuator may cause the tube contacting members to move between a tube occluding and an open position. The occluder may include a release member configured and positioned to enable an operator to manually move the tube contacting member from the tube occluding position to the open position even with no force applied to the occluding member by the force actuator. The force actuator may apply a force sufficient to bend both the first and second occluding members, so that upon application of the force by the force actuator to bend the first and second occluding members, the tube contacting member may move between a tube occluding and an open position. The occluding members may be spring plates pivotally connected together at opposite first and second ends, and the tube contacting member may be a pinch head connected to the spring plates at the first ends, while the second ends of the spring plates may be affixed directly or indirectly to a housing to which the occluder is connected. In one embodiment, the force actuator comprises an inflatable bladder positioned between the first and second occluding members. The force actuator may increase a distance between the first and second occluding members in a region where the first and second occluding members are in opposition so as to move the tube contacting member between a tube occluding and an open position. In one embodiment, the force actuator may bend one or both of the occluding members to move the tube contacting member from a tube occluding position to an open position.

Various aspects of the invention are described above and below with reference to illustrative embodiments. It should be understood that the various aspects of the invention may be used alone and/or in any suitable combination with other aspects of the invention. For example, the pump volume determination features described herein may be used with a liquid handling cassette having the specific features described, or with any other suitable pump configuration.

BRIEF DESCRIPTION OF THE DRAWINGS

Aspects of the invention are described below with reference to illustrative embodiments that are shown, at least in part, in the following figures, in which like numerals reference like elements, and wherein.

DETAILED DESCRIPTION

Although aspects of the invention are described in relation to a peritoneal dialysis system, certain aspects of the invention can be used in other medical applications, including infusion systems such as intravenous infusion systems or extracorporeal blood flow systems, and irrigation and/or fluid exchange systems for the stomach, intestinal tract, urinary bladder, pleural space or other body or organ cavity. Thus, aspects of the invention are not limited to use in peritoneal dialysis in particular, or dialysis in general.

Figure 1:
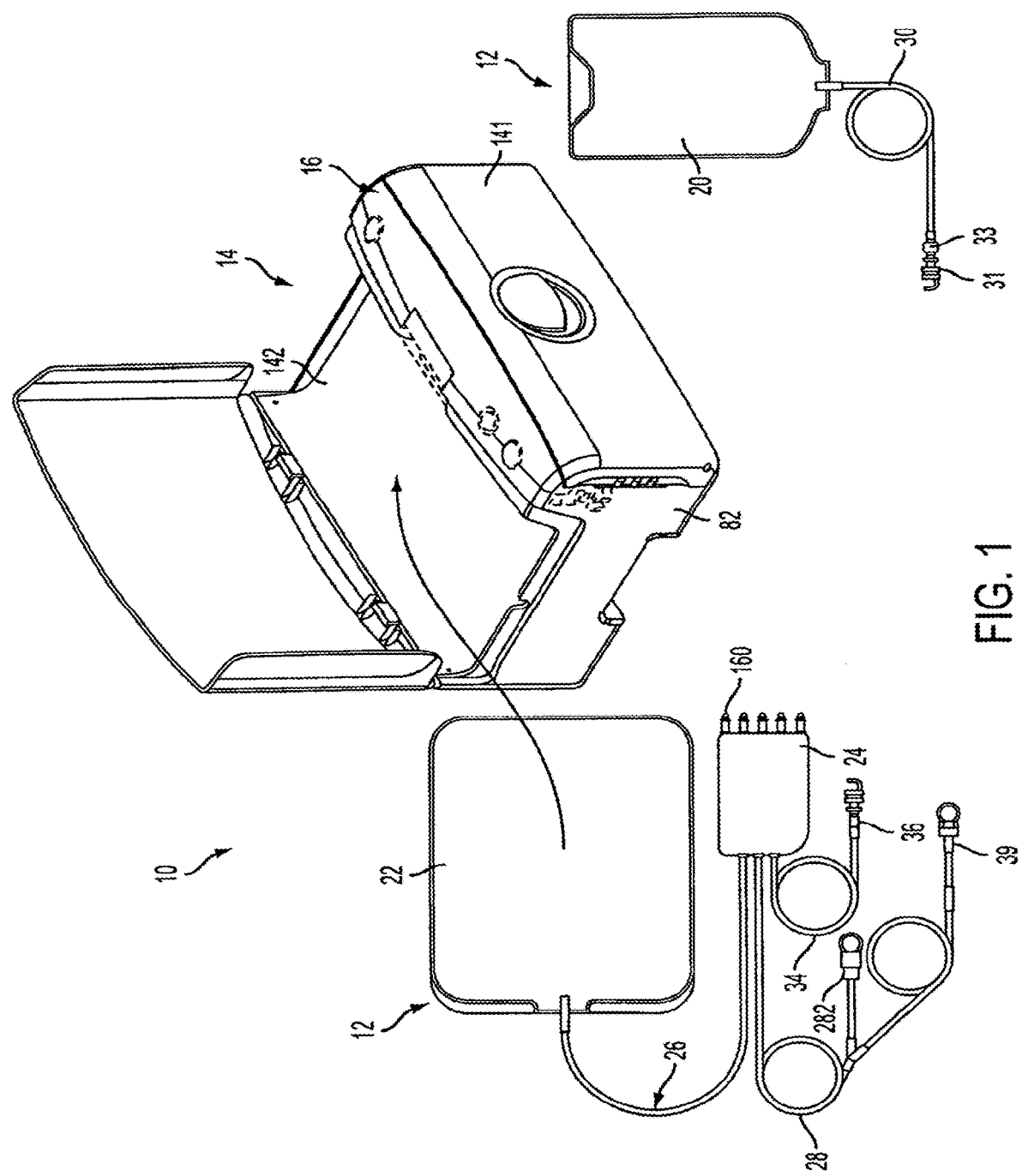
FIG. 1 shows a schematic view of an automated peritoneal dialysis (APD) system that incorporates one or more aspects of the invention.

APD System FIG. 1 shows an automated peritoneal dialysis (APD) system 10 that may incorporate one or more aspects of the invention. As shown in FIG. 1, for example, the system 10 in this illustrative embodiment includes a dialysate delivery set 12 (which, in certain embodiments, can be a disposable set), a cycler 14 that interacts with the delivery set 12 to pump liquid provided by a solution container 20 (e.g., a bag), and a control system 16 (e.g., including a programmed computer or other data processor, computer memory, an interface to provide information to and receive input from a user or other device, one or more sensors, actuators, relays, pneumatic pumps, tanks, a power supply, and/or other suitable components—only a few buttons for receiving user control input are shown in FIG. 1, but further details regarding the control system components are provided below) that governs the process to perform an APD procedure. In this illustrative embodiment, the cycler 14 and the control system 16 are associated with a common housing 82, but may be associated with two or more housings and/or may be separate from each other. The cycler 14 may have a compact footprint, suited for operation upon a table top or other relatively small surface normally found in the home. The cycler 14 may be lightweight and portable, e.g., carried by hand via handles at opposite sides of the housing 82.

The set 12 in this embodiment is intended to be a single use, disposable item, but instead may have one or more reusable components, or may be reusable in its entirety. The user associates the set 12 with the cycler 14 before beginning each APD therapy session, e.g., by mounting a cassette 24 within a front door 141 of the cycler 14, which interacts with the cassette 24 to pump and control fluid flow in the various lines of the set 12. For example, dialysate may be pumped both to and from the patient to effect APD. Post therapy, the user may remove all or part of the components of the set 12 from the cycler 14.

As is known in the art, prior to use, the user may connect a patient line 34 of the set 12 to his/her indwelling peritoneal catheter (not shown) at a connection 36. In one embodiment, the cycler 14 may be configured to operate with one or more different types of cassettes 24, such as those having differently sized patient lines 34. For example, the cycler 14 may be arranged to operate with a first type of cassette with a patient line 34 sized for use with an adult patient, and a second type of cassette with a patient line 34 sized for an infant or pediatric use. The pediatric patient line 34 may be shorter and have a smaller inner diameter than the adult line so as to minimize the volume of the line, allowing for more controlled delivery of dialysate and helping to avoid returning a relatively large volume of used dialysate to the pediatric patient when the set 12 is used for consecutive drain and fill cycles. A heater bag 22, which is connected to the cassette 24 by a line 26, may be placed on a heater container receiving portion (in this case, a tray) 142 of the cycler 14. The cycler 14 may pump fresh dialysate (via the cassette 24) into the heater bag 22 so that the dialysate may be heated by the heater tray 142, e.g., by electric resistance heating elements associated with the tray 142 to a temperature of about 37 degrees C. Heated dialysate may be provided from the heater bag 22 to the patient via the cassette 24 and the patient line 34. In an alternative embodiment, the dialysate can be heated on its way to the patient as it enters, or after it exits, the cassette 24 by passing the dialysate through tubing in contact with the heater tray 142, or through an in-line fluid heater (which may be provided in the cassette 24). Used dialysate may be pumped from the patient via the patient line 34 to the cassette 24 and into a drain line 28, which may include one or more clamps to control flow through one or more branches of the drain line 28. In this illustrative embodiment, the drain line 28 may include a connector 39 for connecting the drain line 28 to a dedicated drain receptacle, and an effluent sample port 282 for taking a sample of used dialysate for testing or other analysis. The user may also mount the lines 30 of one or more containers 20 within the door 141. The lines 30 may also be connected to a continuous or real-time dialysate preparation system. (The lines 26, 28, 30, 34 may include a flexible tubing and/or suitable connectors and other components (such as pinch valves, etc.) as desired.) The containers 20 may contain sterile peritoneal dialysis solution for infusion, or other materials (e.g., materials used by the cycler 14 to formulate dialysate by mixing with water, or admixing different types of dialysate solutions).

The lines 30 may be connected to spikes 160 of the cassette 24, which are shown in FIG. 1 covered by removable caps. In one aspect of the invention described in more detail below, the cycler 14 may automatically remove caps from one or more spikes 160 of the cassette 24 and connect lines 30 of solution containers 20 to respective spikes 160. This feature may help reduce the possibility of infection or contamination by reducing the chance of contact of non-sterile items with the spikes 160.

With various connections made, the control system 16 may pace the cycler 14 through a series of fill, dwell, and/or drain cycles typical of an APD procedure. For example, during a fill phase, the cycler 14 may pump dialysate (by way of the cassette 24) from one or more containers 20 (or other source of dialysate supply) into the heater bag 22 for heating. Thereafter, the cycler 14 may infuse heated dialysate from the heater bag 22 through the cassette 24 and into the patient's peritoneal cavity via the patient line 34. Following a dwell phase, the cycler 14 may institute a drain phase, during which the cycler 14 pumps used dialysate from the patient via the line 34 (again by way of the cassette 24), and discharges spent dialysis solution into a nearby drain (not shown) via the drain line 28.

The cycler 14 does not necessarily require the solution containers 20 and/or the heater bag 22 to be positioned at a prescribed head height above the cycler 14, e.g., because the cycler 14 is not necessarily a gravity flow system. Instead, the cycler 14 may emulate gravity flow, or otherwise suitably control flow of dialysate solution, even with the source solution containers 20 above, below or at a same height as the cycler 14, with the patient above or below the cycler, etc. For example, the cycler 14 can emulate a fixed head height during a given procedure, or the cycler 14 can change the effective head height to either increase or decrease pressure applied to the dialysate during a procedure. The cycler 14 may also adjust the rate of flow of dialysate. In one aspect of the invention, the cycler 14 may adjust the pressure and/or flow rate of dialysate when provided to the patient or drawn from the patient so as to reduce the patient's sensation of the fill or drain operation. Such adjustment may occur during a single fill and/or drain cycle, or may be adjusted across different fill and/or drain cycles. In one embodiment, the cycler 14 may taper the pressure used to draw used dialysate from the patient near the end of a drain operation. Because the cycler 14 may establish an artificial head height, it may have the flexibility to interact with and adapt to the particular physiology or changes in the relative elevation of the patient.

Cassette

In one aspect of the invention, a cassette 24 may include patient and drain lines that are separately occludable with respect to solution supply lines. That is, safety critical flow to and from patient line may be controlled, e.g., by pinching the lines to stop flow, without the need to occlude flow through one or more solution supply lines. This feature may allow for a simplified occluder device since occlusion may be performed with respect to only two lines as opposed to occluding other lines that have little or no effect on patient safety. For example, in a circumstance where a patient or drain connection becomes disconnected, the patient and drain lines may be occluded. However, the solution supply and/or heater bag lines may remain open for flow, allowing the cycler 14 to prepare for a next dialysis cycle; e.g., separate occlusion of patient and drain lines may help ensure patient safety while permitting the cycler 14 to continue to pump dialysate from one or more containers 20 to the heater bag 22 or to other solution containers 20.

In another aspect of the invention, the cassette may have patient, drain and heater bag lines at one side or portion of the cassette and one or more solution supply lines at another side or portion of the cassette, e.g., an opposite side of the cassette. Such an arrangement may allow for separate occlusion of patient, drain or heater bag lines with respect to solution lines as discussed above. Physically separating the lines attached to the cassette by type or function allows for more efficient control of interaction with lines of a certain type or function. For example, such an arrangement may allow for a simplified occluder design because less force is required to occlude one, two or three of these lines than all lines leading to or away from the cassette. Alternately, this arrangement may allow for more effective automated connection of solution supply lines to the cassette, as discussed in more detail below. That is, with solution supply lines and their respective connections located apart from patient, drain and/or heater bag lines, an automated de-capping and connection device may remove caps from spikes on the cassette as well as caps on solution supply lines, and connect the lines to respective spikes without interference by the patient, drain or heater bag lines.

Figure 2:
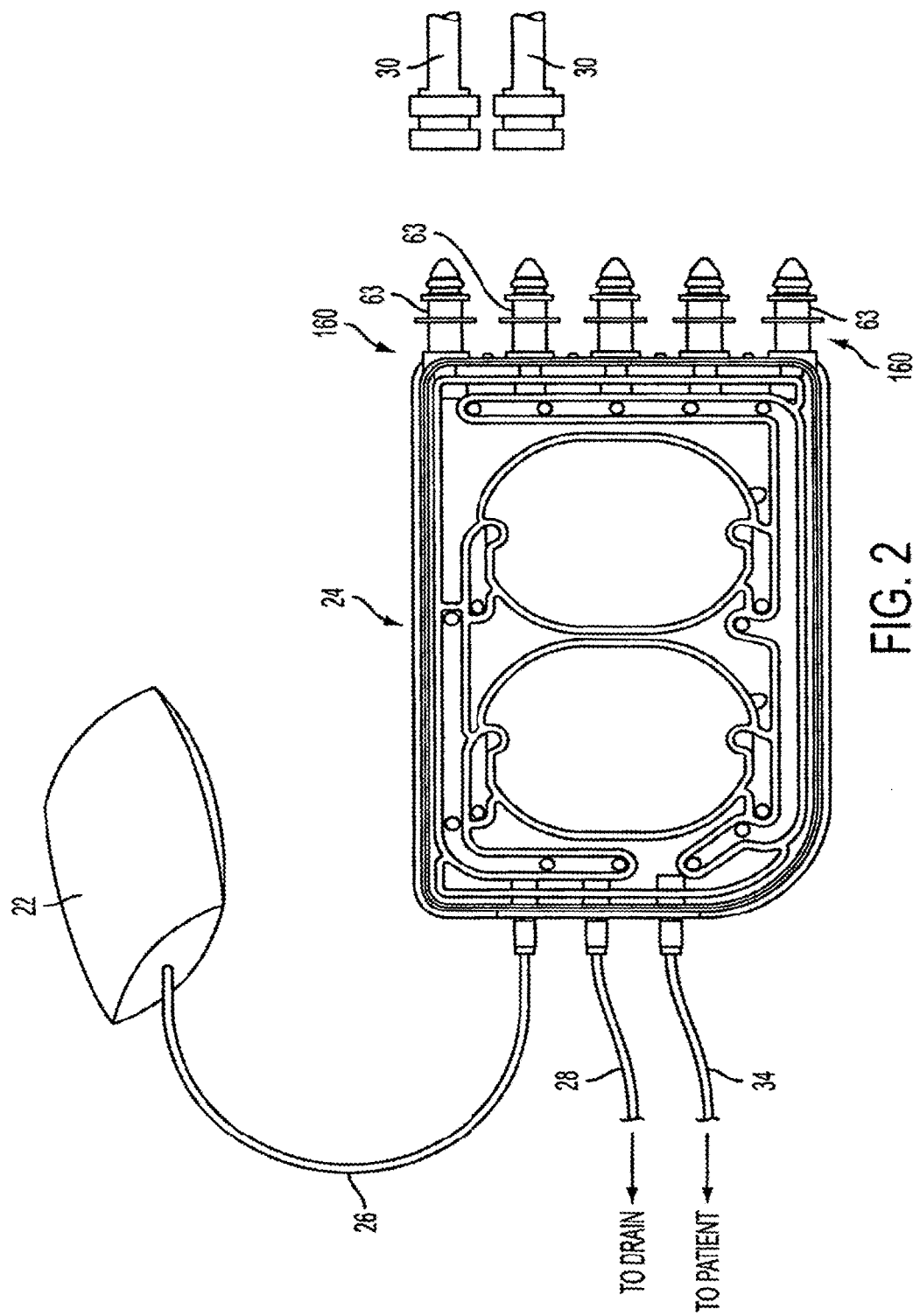
FIG. 2 is a schematic view of an illustrative set for use with the APD system of FIG. 1.

FIG. 2 shows an illustrative embodiment of a cassette 24 that incorporates aspects of the invention described above. In this embodiment, the cassette 24 has a generally planar body and the heater bag line 26, the drain line 28 and the patient line 34 are connected at respective ports on the left end of the cassette body, while the right end of the cassette body may include five spikes 160 to which solution supply lines 30 may be connected. In the arrangement shown in FIG. 2, each of the spikes 160 is covered by a spike cap 63, which may be removed, exposing the respective spike and allowing connection to a respective line 30. As described above, the lines 30 may be attached to one or more solution containers or other sources of material, e.g., for use in dialysis and/or the formulation of dialysate, or connected to one or more collection bags for sampling purposes or for peritoneal equilibration testing (PET test).

Figure 3:
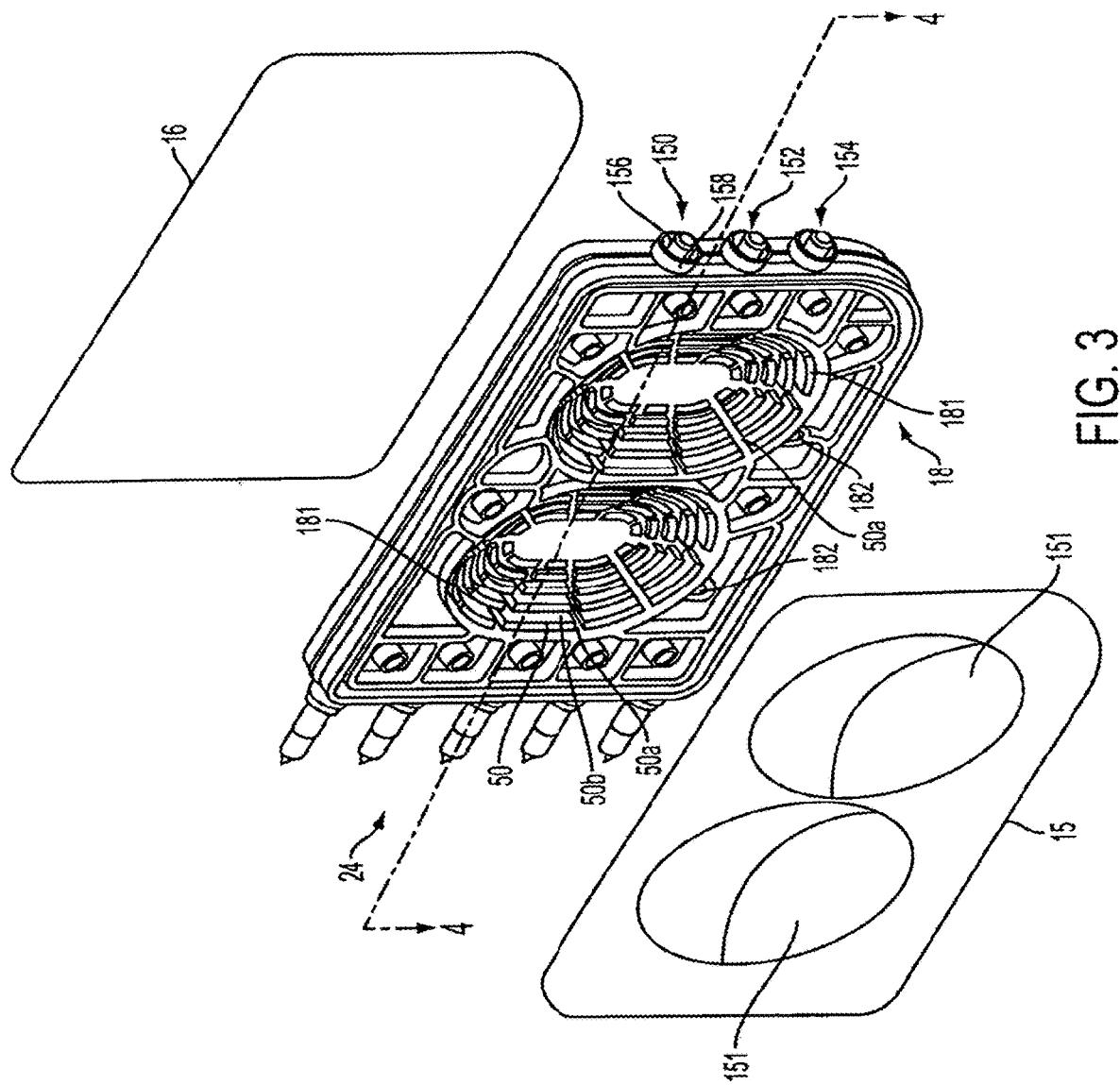
FIG. 3 is an exploded perspective view of a cassette in a first embodiment.
Figure 4:
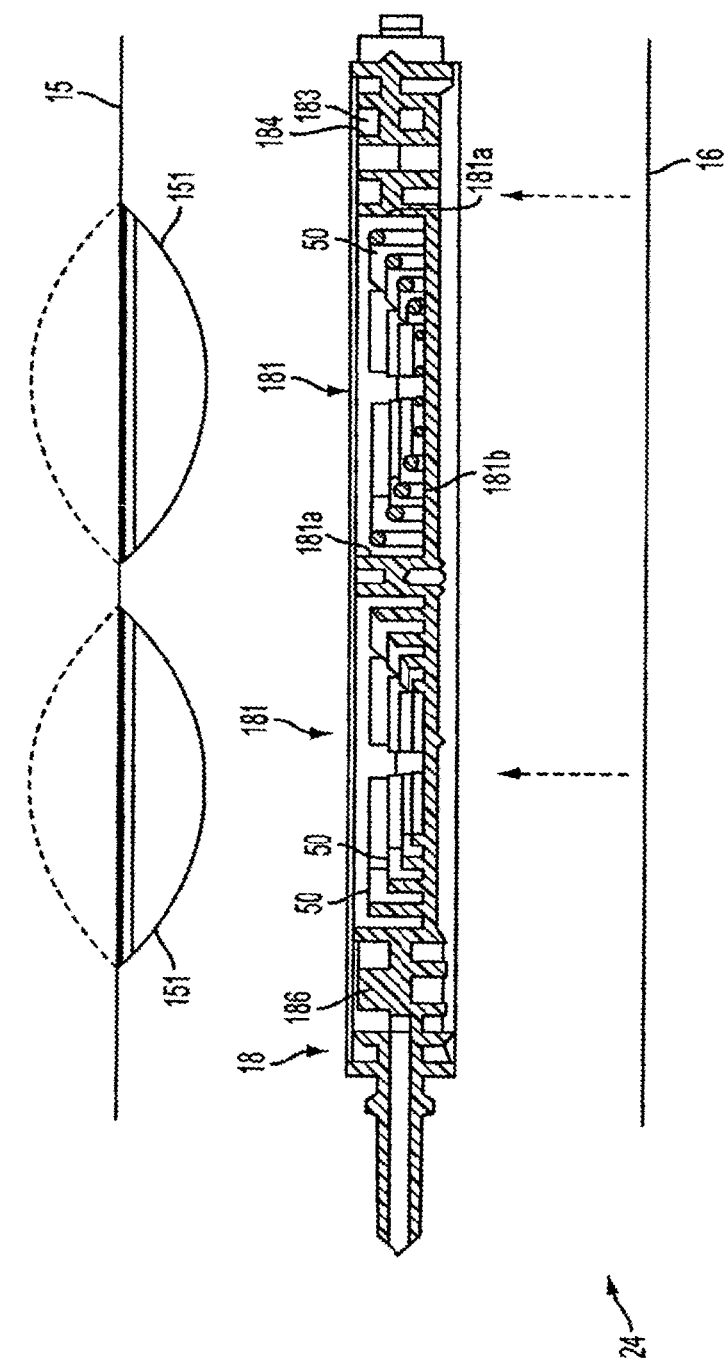
FIG. 4 is a cross sectional view of the cassette along the line 4-4 in FIG. 3.

FIGS. 3 and 4 show exploded views (perspective and top views, respectively) of the cassette 24 in this illustrative embodiment. The cassette 24 is formed as a relatively thin and flat member having a generally planar shape, e.g., may include components that are molded, extruded or otherwise formed from a suitable plastic. In this embodiment, the cassette 24 includes a base member 18 that functions as a frame or structural member for the cassette 24 as well as forming, at least in part, various flow channels, ports, valve portions, etc. The base member 18 may be molded or otherwise formed from a suitable plastic or other material, such as a polymethyl methacrylate (PMMA) acrylic, or a cyclic olefin copolymer/ultra low density polyethylene (COC/ULDPE), and may be relatively rigid. In an embodiment, the ratio of COC to ULDPE can be approximately 85%/15%. FIG. 3 also shows the ports for the heater bag (port 150), drain (port 152) and the patient (port 154) that are formed in the base member 18. Each of these ports may be arranged in any suitable way, such as, for example, a central tube 156 extending from an outer ring or skirt 158, or a central tube alone. Flexible tubing for each of the heater bag, drain and patient lines 26, 28, 34 may be connected to the central tube 156 and engaged by the outer ring 158, if present.

Both sides of the base member 18 may be covered, at least in part, by a membrane 15 and 16, e.g., a flexible polymer film made from, for example, polyvinyl chloride (PVC), that is cast, extruded or otherwise formed. Alternatively, the sheet may be formed as a laminate of two or more layers of poly-cyclohexylene dimethylene cyclohexanedicarboxylate (PCCE) and/or ULDPE, held together, for example, by a coextrudable adhesive (CXA). In some embodiments, the membrane thickness may be in the range of approximately 0.002 to 0.020 inches thick. In a preferred embodiment, the thickness of a PVC-based membrane may be in the range of approximately 0.012 to 0.016 inches thick, and more preferably approximately 0.014 inches thick. In another preferred embodiment, such as, for example, for laminate sheets, the thickness of the laminate may be in the range of approximately 0.006 to 0.010 inches thick, and more preferably approximately 0.008 inches thick.

Both membranes 15 and 16 may function not only to close or otherwise form a part of flowpaths of the cassette 24, but also may be moved or otherwise manipulated to open/close valve ports and/or to function as part of a pump diaphragm, septum or wall that moves fluid in the cassette 24. For example, the membranes 15 and 16 may be positioned on the base member 18 and sealed (e.g., by heat, adhesive, ultrasonic welding or other means) to a rim around the periphery of the base member 18 to prevent fluid from leaking from the cassette 24. The membrane 15 may also be bonded to other, inner walls of the base member 18, e.g., those that form various channels, or may be pressed into sealing contact with the walls and other features of the base member 18 when the cassette 24 suitably mounted in the cycler 14. Thus, both of the membranes 15 and 16 may be sealed to a peripheral rim of the base member 18, e.g., to help prevent leaking of fluid from the cassette 24 upon its removal from the cycler 14 after use, yet be arranged to lie, unattached, over other portions of the base member 18. Once placed in the cycler 14, the cassette 24 may be squeezed between opposed gaskets or other members so that the membranes 15 and 16 are pressed into sealing contact with the base member 18 at regions inside of the periphery, thereby suitably sealing channels, valve ports, etc., from each other.

Other arrangements for the membranes 15 and 16 are possible. For example, the membrane 16 may be formed by a rigid sheet of material that is bonded or otherwise made integral with the body 18. Thus, the membrane 16 need not necessarily be, or include, a flexible member. Similarly, the membrane 15 need not be flexible over its entire surface, but instead may include one or more flexible portions to permit pump and/or valve operation, and one or more rigid portions, e.g., to close flowpaths of the cassette 24. It is also possible that the cassette 24 may not include the membrane 16 or the membrane 15, e.g., where the cycler 14 includes a suitable member to seal pathways of the cassette, control valve and pump function, etc.

Figure 5:
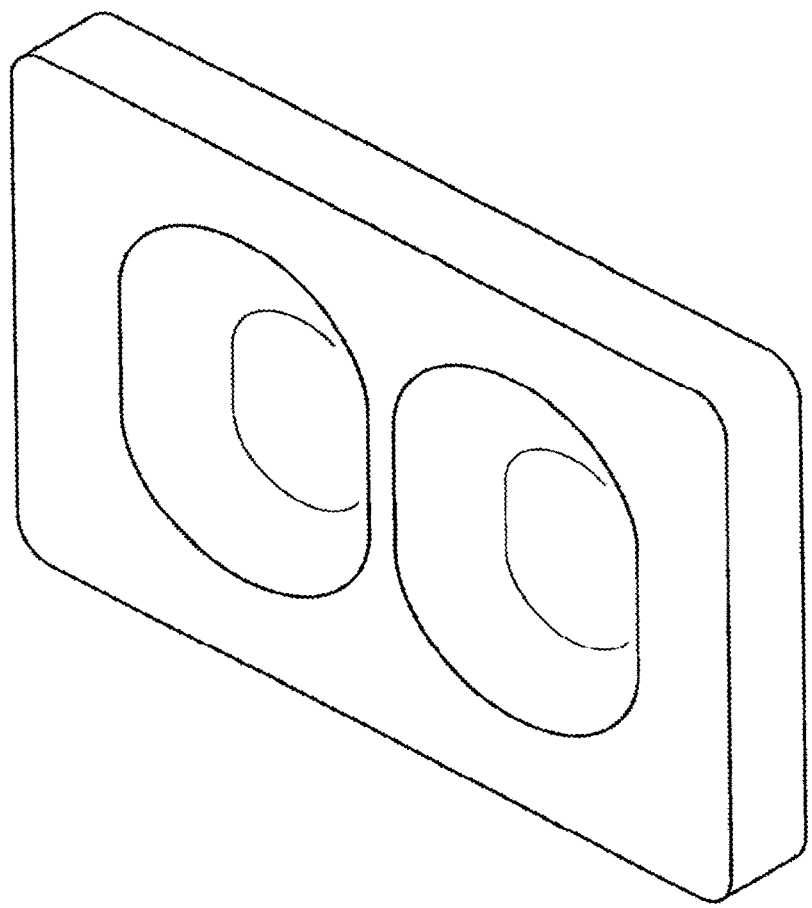
FIG. 5 is a perspective view of a vacuum mold that may be used to form a membrane having pre-formed pump chamber portions in an illustrative embodiment.

In accordance with another aspect of the invention, the membrane 15 may include a pump chamber portion 151 ("pump membrane") that is formed to have a shape that closely conforms to the shape of a corresponding pump chamber 181 depression in the base 18. For example, the membrane 15 may be generally formed as a flat member with thermoformed (or otherwise formed) dome-like shapes 151 that conform to the pump chamber depressions of the base member 18. The dome-like shape of the pre-formed pump chamber portions 151 may be constructed, for example, by heating and forming the membrane over a vacuum form mold of the type shown in FIG. 5. As shown in FIG. 5, the vacuum may be applied through a collection of holes along the wall of the mold. Alternatively, the wall of the mold can be constructed of a porous gas-permeable material, which may result in a more uniformly smooth surface of the molded membrane. In this way, the membrane 15 may move relative to the pump chambers 181 to effect pumping action without requiring stretching of the membrane 15 (or at least minimal stretching of the membrane 15), both when the membrane 15 is moved maximally into the pump chambers 181 and (potentially) into contact with spacer elements 50 (e.g., as shown in solid line in FIG. 4 while pumping fluid out of the pump chamber 181), and when the membrane 15 is maximally withdrawn from the pump chamber 181 (e.g., as shown in dashed line in FIG. 4 when drawing fluid into the pump chamber 181). Avoiding stretching of the membrane 15 may help prevent pressure surges or other changes in fluid delivery pressure due to sheet stretch and/or help simplify control of the pump when seeking to minimize pressure variation during pump operation. Other benefits may be found, including reduced likelihood of membrane 15 failure (e.g., due to tears in the membrane 15 resulting from stresses place on the membrane 15 during stretching), and/or improved accuracy in pump delivery volume measurement, as described in more detail below. In one embodiment, the pump chamber portions 151 may be formed to have a size (e.g., a define a volume) that is about 85-110% of the pump chamber 181, e.g., if the pump chamber portions 151 define a volume that is about 100% of the pump chamber volume, the pump chamber portion 151 may lie in the pump chamber 181 and in contact with the spacers 50 while at rest and without being stressed.

Providing greater control of the pressure used to generate a fill and delivery stroke of liquid into and out of a pump chamber may have several advantages. For example, it may be desirable to apply the minimum negative pressure possible when the pump chamber draws fluid from the patient's peritoneal cavity during a drain cycle. A patient may experience discomfort during the drain cycle of a treatment in part because of the negative pressure being applied by the pumps during a fill stroke. The added control that a pre-formed membrane can provide to the negative pressure being applied during a fill stroke may help to reduce the patient's discomfort.

A number of other benefits may be realized by using pump membranes pre-formed to the contour of the cassette pump chamber. For example, the flow rate of liquid through the pump chamber can be made more uniform, because a constant pressure or vacuum can be applied throughout the pump stroke, which in turn may simplify the process of regulating the heating of the liquid. Moreover, temperature changes in the cassette pump may have a smaller effect on the dynamics of displacing the membrane, as well as the accuracy of measuring pressures within the pump chambers. In addition, pressure spikes within the fluid lines can be minimized. Also, correlating the pressures measured by pressure transducers on the control (e.g. pneumatic) side of the membrane with the actual pressure of the liquid on the pump chamber side of the membrane may be simpler. This in turn may permit more accurate head height measurements of the patient and fluid source bags prior to therapy, improve the sensitivity of detecting air in the pump chamber, and improve the accuracy of volumetric measurements. Furthermore, eliminating the need to stretch the membrane may allow for the construction and use of pump chambers having greater volumes.

In this embodiment, the cassette 24 includes a pair of pump chambers 181 that are formed in the base member 18, although one pump chamber or more than two pump chambers are possible. In accordance with an aspect of the invention, the inner wall of pump chambers 181 includes spacer elements 50 that are spaced from each other and extend from the inner wall of pump chamber 18 to help prevent portions of the membrane 15 from contacting the inner wall of pump chamber 181. (As shown on the right-side pump chamber 181 in FIG. 4, the inner wall is defined by side portions 181a and a bottom portion 181b. The spacers 50 extend upwardly from the bottom portion 181b in this embodiment, but could extend from the side portions 181a or be formed in other ways.) By preventing contact of the membrane 15 with the pump chamber inner wall, the spacer elements 50 may provide a dead space (or trap volume) which may help trap air or other gas in the pump chamber 181 and inhibit the gas from being pumped out of the pump chamber 181 in some circumstances. In other cases, the spacers 50 may help the gas move to an outlet of the pump chamber 181 so that the gas may be removed from the pump chamber 181, e.g., during priming. Also, the spacers 50 may help prevent the membrane 15 from sticking to the pump chamber inner wall and/or allow flow to continue through the pump chamber 181, even if the membrane 15 is pressed into contact with the spacer elements 50. In addition, the spacers 50 help to prevent premature closure of the outlet port of the pump chamber (openings 187 and/or 191) if the sheet happens to contact the pump chamber inner wall in a non-uniform manner. Further details regarding the arrangement and/or function of spacers 50 are provided in U.S. Pat. Nos. 6,302,653 and 6,382,923, both of which are incorporated herein by reference.

In this embodiment, the spacer elements 50 are arranged in a kind of "stadium seating" arrangement such that the spacer elements 50 are arranged in a concentric elliptical pattern with ends of the spacer elements 50 increasing in height from the bottom portion 181b of the inner wall with distance away from the center of the pump chamber 181 to form a semi-elliptical domed shaped region (shown by dotted line in FIG. 4). Positioning spacer elements 50 such that the ends of the spacer elements 50 form a semi-elliptical region that defines the domed region intended to be swept by the pump chamber portion 151 of the membrane 15 may allow for a desired volume of dead space that minimizes any reduction to the intended stroke capacity of pump chambers 181. As can be seen in FIG. 3 (and FIG. 6), the "stadium seating" arrangement in which spacer elements 50 are arranged may include "aisles" or breaks 50a in the elliptical pattern. Breaks (or aisles) 50a help to maintain an equal gas level throughout the rows (voids or dead space) 50b between spacer elements 50 as fluid is delivered from the pump chamber 181. For example, if the spacer elements 50 were arranged in the stadium seating arrangement shown in FIG.

6 without breaks (or aisles) 50a or other means of allowing liquid and air to flow between spacer elements 50, the membrane 15 might bottom out on the spacer element 50 located at the outermost periphery of the pump chamber 181, trapping whatever gas or liquid is present in the void between this outermost spacer element 50 and the side portions 181a of the pump chamber wall. Similarly, if the membrane 15 bottomed out on any two adjacent spacer elements 50, any gas and liquid in the void between the elements 50 may become trapped. In such an arrangement, at the end of the pump stroke, air or other gas at the center of pump chamber 181 could be delivered while liquid remains in the outer rows. Supplying breaks (or aisles) 50a or other means of fluidic communication between the voids between spacer elements 50 helps to maintain an equal gas level throughout the voids during the pump stroke, such that air or other gas may be inhibited from leaving the pump chamber 181 unless the liquid volume has been substantially delivered.

In certain embodiments, spacer elements 50 and/or the membrane 15 may be arranged so that the membrane 15 generally does not wrap or otherwise deform around individual spacers 50 when pressed into contact with them, or otherwise extend significantly into the voids between spacers 50. Such an arrangement may lessen any stretching or damage to membrane 15 caused by wrapping or otherwise deforming around one or more individual spacer elements 50. For example, it has also been found to be advantageous in this embodiment to make the size of the voids between spacers 50 approximately equal in width to the width of the spacers 50. This feature has shown to help prevent deformation of the membrane 15, e.g., sagging of the membrane into the voids between spacers 50, when the membrane 15 is forced into contact with the spacers 50 during a pumping operation.

In accordance with another aspect of the invention, the inner wall of pump chambers 181 may define a depression that is larger than the space, for example a semi-elliptical or domed space, intended to be swept by the pump chamber portion 151 of the membrane 15. In such instances, one or more spacer elements 50 may be positioned below the domed region intended to be swept by the membrane portion 151 rather than extending into that domed region. In certain instances, the ends of spacer elements 50 may define the periphery of the domed region intended to be swept by the membrane 15. Positioning spacer elements 50 outside of, or adjacent to, the periphery of the domed region intended to be swept by the membrane portion 151 may have a number of advantages. For example, positioning one or more spacer elements 50 such that the spacer elements are outside of, or adjacent to, the domed region intended to be swept by the flexible membrane provides a dead space between the spacers and the membrane, such as described above, while minimizing any reduction to the intended stroke capacity of pump chambers 181.

Figure 6:
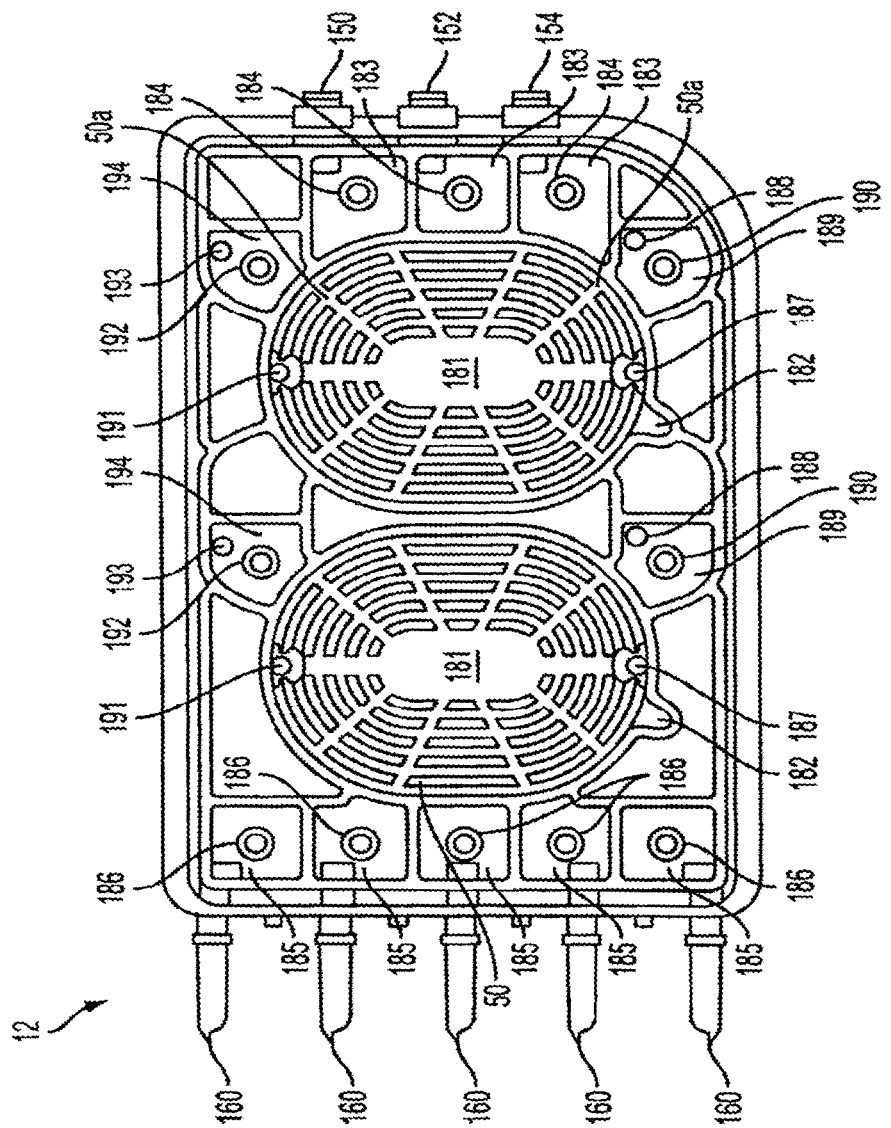
FIG. 6 shows a front view of the cassette body of FIG. 3.
Figure 7:
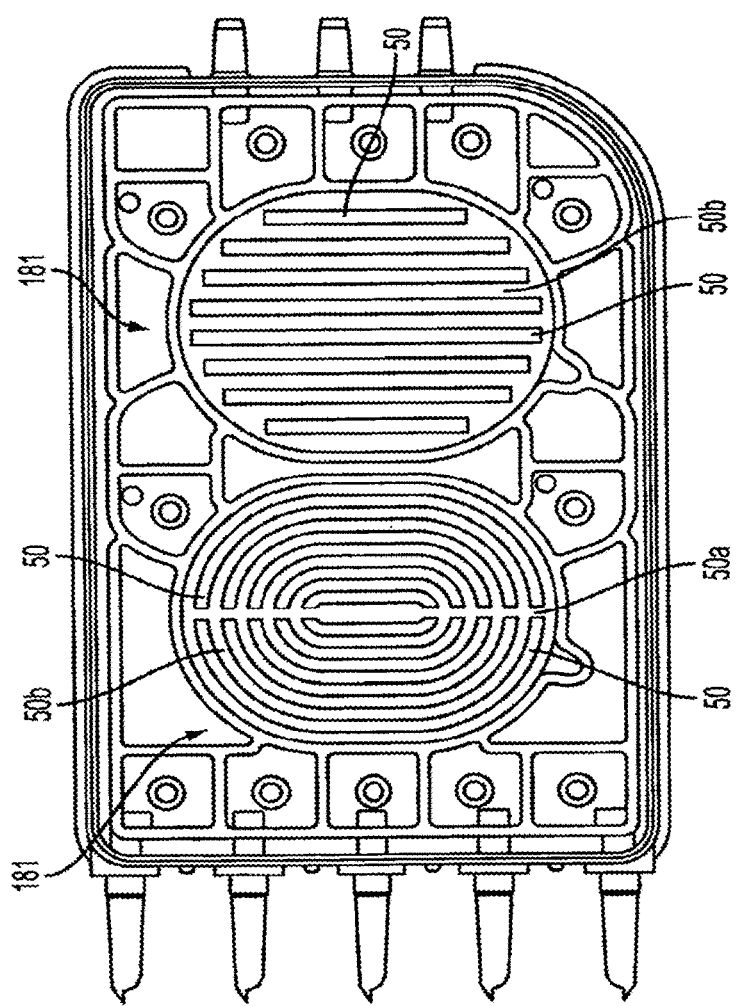
FIG. 7 is a front view of a cassette body including two different spacer arrangements in an illustrative embodiment.

It should be understood that the spacer elements 50, if present, in a pump chamber may be arranged in any other suitable way, such as for example, shown in FIG. 7. The left side pump chamber 181 in FIG. 7 includes spacers 50 arranged similarly to that in FIG. 6, but there is only one break or aisle 50a that runs vertically through the approximate center of the pump chamber 181. The spacers 50 may be arranged to define a concave shape similar to that in FIG. 6 (i.e., the tops of the spacers 50 may form the semi-elliptical shape shown in FIGS. 3 and 4), or may be arranged in other suitable ways, such as to form a spherical shape, a box-like shape, and so on. The right-side pump chamber 181 in FIG. 7 shows an embodiment in which the spacers 50 are arranged vertically with voids 50b between spacers 50 also arranged vertically. As with the left-side pump chamber, the spacers 50 in the right-side pump chamber 181 may define a semi-elliptical, spherical, box-like or any other suitably shaped depression. It should be understood, however, that the spacer elements 50 may have a fixed height, a different spatial pattern that those shown, and so on.

Also, the membrane 15 may itself have spacer elements or other features, such as ribs, bumps, tabs, grooves, channels, etc., in addition to, or in place of the spacer elements 50. Such features on the membrane 15 may help prevent sticking of the membrane 15, etc., and/or provide other features, such as helping to control how the sheet folds or otherwise deforms when moving during pumping action. For example, bumps or other features on the membrane 15 may help the sheet to deform consistently and avoid folding at the same area(s) during repeated cycles. Folding of a same area of the membrane 15 at repeated cycles may cause the membrane 15 to prematurely fail at the fold area, and thus features on the membrane 15 may help control the way in which folds occur and where.

Figure 8:
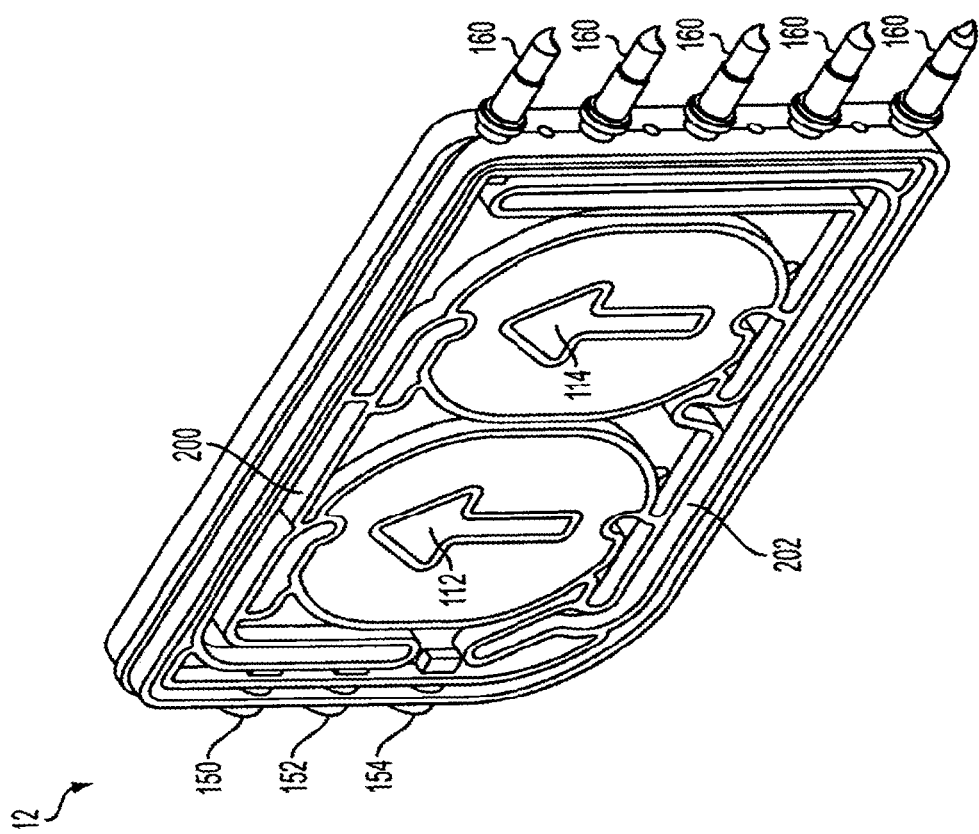
FIG. 8 is a rear perspective view of the cassette body of FIG. 3.
Figure 9:
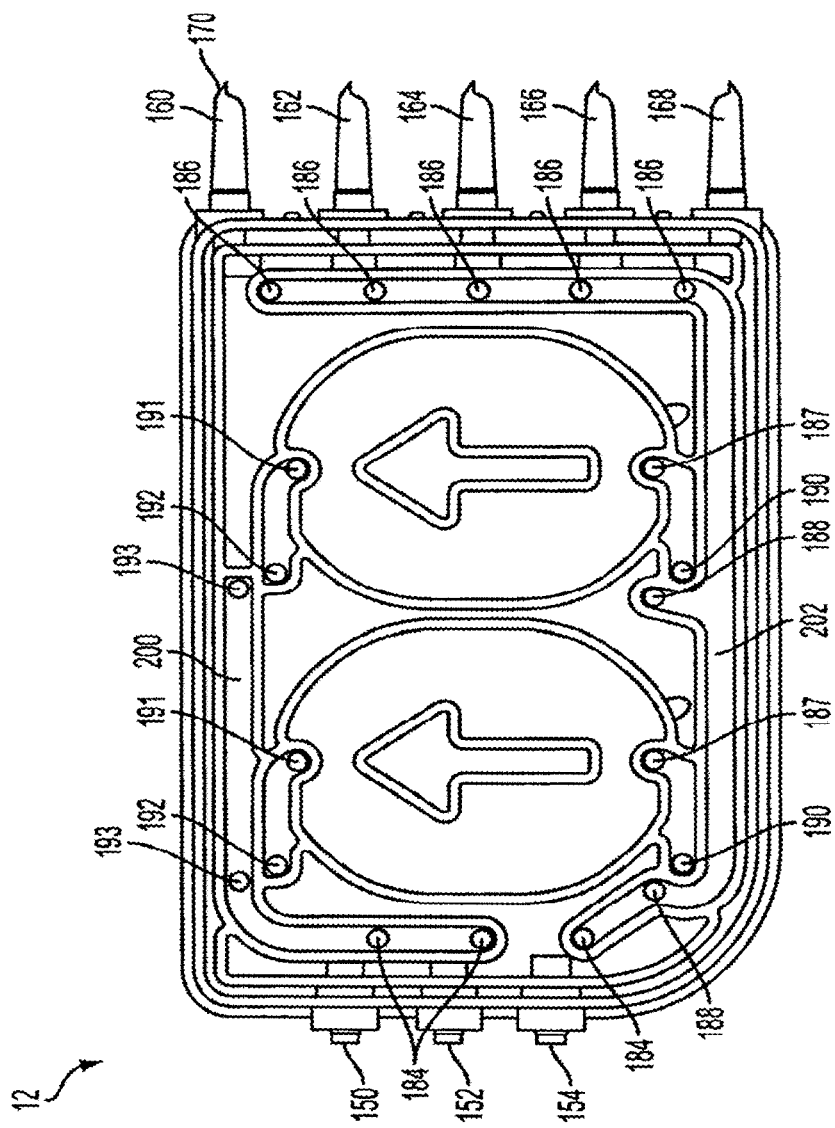
FIG. 9 is a rear view of the cassette body of FIG. 3.

In this illustrative embodiment, the base member 18 of the cassette 24 defines a plurality of controllable valve features, fluid pathways and other structures to guide the movement of fluid in the cassette 24. FIG. 6 shows a plan view of the pump chamber side of the base member 18, which is also seen in perspective view in FIG. 3. FIG. 8 shows a perspective view of a back side of the base member 18, and FIG. 9 shows a plan view of the back side of the base member 18. The tube 156 for each of the ports 150, 152 and 154 fluidly communicates with a respective valve well 183 that is formed in the base member 18. The valve wells 183 are fluidly isolated from each other by walls surrounding each valve well 183 and by sealing engagement of the membrane 15 with the walls around the wells 183. As mentioned above, the membrane 15 may sealingly engage the walls around each valve well 183 (and other walls of the base member 18) by being pressed into contact with the walls, e.g., when loaded into the cycler 14. Fluid in the valve wells 183 may flow into a respective valve port 184, if the membrane 15 is not pressed into sealing engagement with the valve port 184. Thus, each valve port 184 defines a valve (e.g., a "volcano valve") that can be opened and closed by selectively moving a portion of the membrane 15 associated with the valve port 184. As will be described in more detail below, the cycler 14 may selectively control the position of portions of the membrane 15 so that valve ports (such as ports 184) may be opened or closed so as to control flow through the various fluid channels and other pathways in the cassette 24. Flow through the valve ports 184 leads to the back side of the base member 18. For the valve ports 184 associated with the heater bag and the drain (ports 150 and 152), the valve ports 184 lead to a common channel 200 formed at the back side of the base member 18. As with the valve wells 183, the channel 200 is isolated from other channels and pathways of the cassette 24 by the sheet 16 making sealing contact with the walls of the base member 18 that form the channel 200. For the valve port 184 associated with the patient line port 154, flow through the port 184 leads to a common channel 202 on the back side of the base member 18.

Returning to FIG. 6, each of the spikes 160 (shown uncapped in FIG. 6) fluidly communicates with a respective valve well 185, which are isolated from each other by walls and sealing engagement of the membrane 15 with the walls that form the wells 185. Fluid in the valve wells 185 may flow into a respective valve port 186, if the membrane 15 is not in sealing engagement with the port 186. (Again, the position of portions of the membrane 15 over each valve port 186 can be controlled by the cycler 14 to open and close the valve ports 186.) Flow through the valve ports 186 leads to the back side of the base member 18 and into the common channel 202. Thus, in accordance with one aspect of the invention, a cassette may have a plurality of solution supply lines (or other lines that provide materials for providing dialysate) that are connected to a common manifold or channel of the cassette, and each line may have a corresponding valve to control flow from/to the line with respect to the common manifold or channel. Fluid in the channel 202 may flow into lower openings 187 of the pump chambers 181 by way of openings 188 that lead to lower pump valve wells 189 (see FIG. 6). Flow from the lower pump valve wells 189 may pass through a respective lower pump valve port 190 if a respective portion of the membrane 15 is not pressed in sealing engagement with the port 190. As can be seen in FIG. 9, the lower pump valve ports 190 lead to a channel that communicates with the lower openings 187 of the pump chambers 181. Flow out of the pump chambers 181 may pass through the upper openings 191 and into a channel that communicates with an upper valve port 192. Flow from the upper valve port 192 (if the membrane 15 is not in sealing engagement with the port 192) may pass into a respective upper valve well 194 and into an opening 193 that communicates with the common channel 200 on the back side of the base member 18.

As will be appreciated, the cassette 24 may be controlled so that the pump chambers 181 can pump fluid from and/or into any of the ports 150, 152 and 154 and/or any of the spikes 160. For example, fresh dialysate provided by one of the containers 20 that is connected by a line 30 to one of the spikes 160 may be drawn into the common channel 202 by opening the appropriate valve port 186 for the proper spike 160 (and possibly closing other valve ports 186 for other spikes). Also, the lower pump valve ports 190 may be opened and the upper pump valve ports 192 may be closed. Thereafter, the portion of the membrane 15 associated with the pump chambers 181 (i.e., pump membranes 151) may be moved (e.g., away from the base member 18 and the pump chamber inner wall) so as to lower the pressure in the pump chambers 181, thereby drawing fluid in through the selected spike 160 through the corresponding valve port 186, into the common channel 202, through the openings 188 and into the lower pump valve wells 189, through the (open) lower pump valve ports 190 and into the pump chambers 181 through the lower openings 187. The valve ports 186 are independently operable, allowing for the option to draw fluid through any one or a combination of spikes 160 and associated source containers 20, in any desired sequence, or simultaneously. (Of course, only one pump chamber 181 need be operable to draw fluid into itself. The other pump chamber may be left inoperable and closed off to flow by closing the appropriate lower pump valve port 190.)

With fluid in the pump chambers 181, the lower pump valve ports 190 may be closed, and the upper pump valve ports 192 opened. When the membrane 15 is moved toward the base member 18, the pressure in the pump chambers 181 may rise, causing fluid in the pump chambers 181 to pass through the upper openings 191, through the (open) upper pump valve ports 192 and into the upper pump valve wells 194, through the openings 193 and into the common channel 200. Fluid in the channel 200 may be routed to the heater bag port 150 and/or the drain port 152 (and into the corresponding heater bag line or drain line) by opening the appropriate valve port 184. In this way, for example, fluid in one or more of the containers 20 may be drawn into the cassette 24, and pumped out to the heater bag 22 and/or the drain.

Fluid in the heater bag 22 (e.g., after having been suitably heated on the heater tray for introduction into the patient) may be drawn into the cassette 24 by opening the valve port 184 for the heater bag port 150, closing the lower pump valve ports 190, and opening the upper pump valve ports 192. By moving the portions of the membrane 15 associated with the pump chambers 181 away from the base member 18, the pressure in the pump chambers 181 may be lowered, causing fluid flow from the heater bag 22 and into the pump chambers 181. With the pump chambers 181 filled with heated fluid from the heater bag 22, the upper pump valve ports 192 may be closed and the lower pump valve ports 190 opened. To route the heated dialysate to the patient, the valve port 184 for the patient port 154 may be opened and valve ports 186 for the spikes 160 closed. Movement of the membrane 15 in the pump chambers 181 toward the base member 18 may raise the pressure in the pump chambers 181 causing fluid to flow through the lower pump valve ports 190, through the openings 188 and into the common channel 202 to, and through, the (open) valve port 184 for the patient port 154. This operation may be repeated a suitable number of times to transfer a desired volume of heated dialysate to the patient.

When draining the patient, the valve port 184 for the patient port 154 may be opened, the upper pump valve ports 192 closed, and the lower pump valve ports 190 opened (with the spike valve ports 186 closed). The membrane 15 may be moved to draw fluid from the patient port 154 and into the pump chambers 181. Thereafter, the lower pump valve ports 190 may be closed, the upper valve ports 192 opened, and the valve port 184 for the drain port 152 opened. Fluid from the pump chambers 181 may then be pumped into the drain line for disposal or for sampling into a drain or collection container. (Alternatively, fluid may also be routed to one or more spikes 160/lines 30 for sampling or drain purposes). This operation may be repeated until sufficient dialysate is removed from the patient and pumped to the drain.

The heater bag 22 may also serve as a mixing container. Depending on the specific treatment requirements for an individual patient, dialysate or other solutions having different compositions can be connected to the cassette 24 via suitable solution lines 30 and spikes 160. Measured quantities of each solution can be added to heater bag 22 using cassette 24, and admixed according to one or more predetermined formulae stored in microprocessor memory and accessible by control system 16. Alternatively, specific treatment parameters can be entered by the user via user interface 144. The control system 16 can be programmed to compute the proper admixture requirements based on the type of dialysate or solution containers connected to spikes 160, and can then control the admixture and delivery of the prescribed mixture to the patient.

In accordance with an aspect of the invention, the pressure applied by the pumps to dialysate that is infused into the patient or removed from the patient may be controlled so that patient sensations of "tugging" or "pulling" resulting from pressure variations during drain and fill operations may be minimized. For example, when draining dialysate, the suction pressure (or vacuum/negative pressure) may be reduced near the end of the drain process, thereby minimizing patient sensation of dialysate removal. A similar approach may be used when nearing the end of a fill operation, i.e., the delivery pressure (or positive pressure) may be reduced near the end of fill. Different pressure profiles may be used for different fill and/or drain cycles in case the patient is found to be more or less sensitive to fluid movement during different cycles of the therapy. For example, a relatively higher (or lower) pressure may be used during fill and/or drain cycles when a patient is asleep, as compared to when the patient is awake. The cycler 14 may detect the patient's sleep/awake state, e.g., using an infrared motion detector and inferring sleep if patient motion is reduced, or using a detected change in blood pressure, brain waves, or other parameter that is indicative of sleep, and so on. Alternately, the cycler 14 may simply "ask" the patient— "are you asleep?" and control system operation based on the patient's response (or lack of response).

Set Loading and Operation

Figure 10:
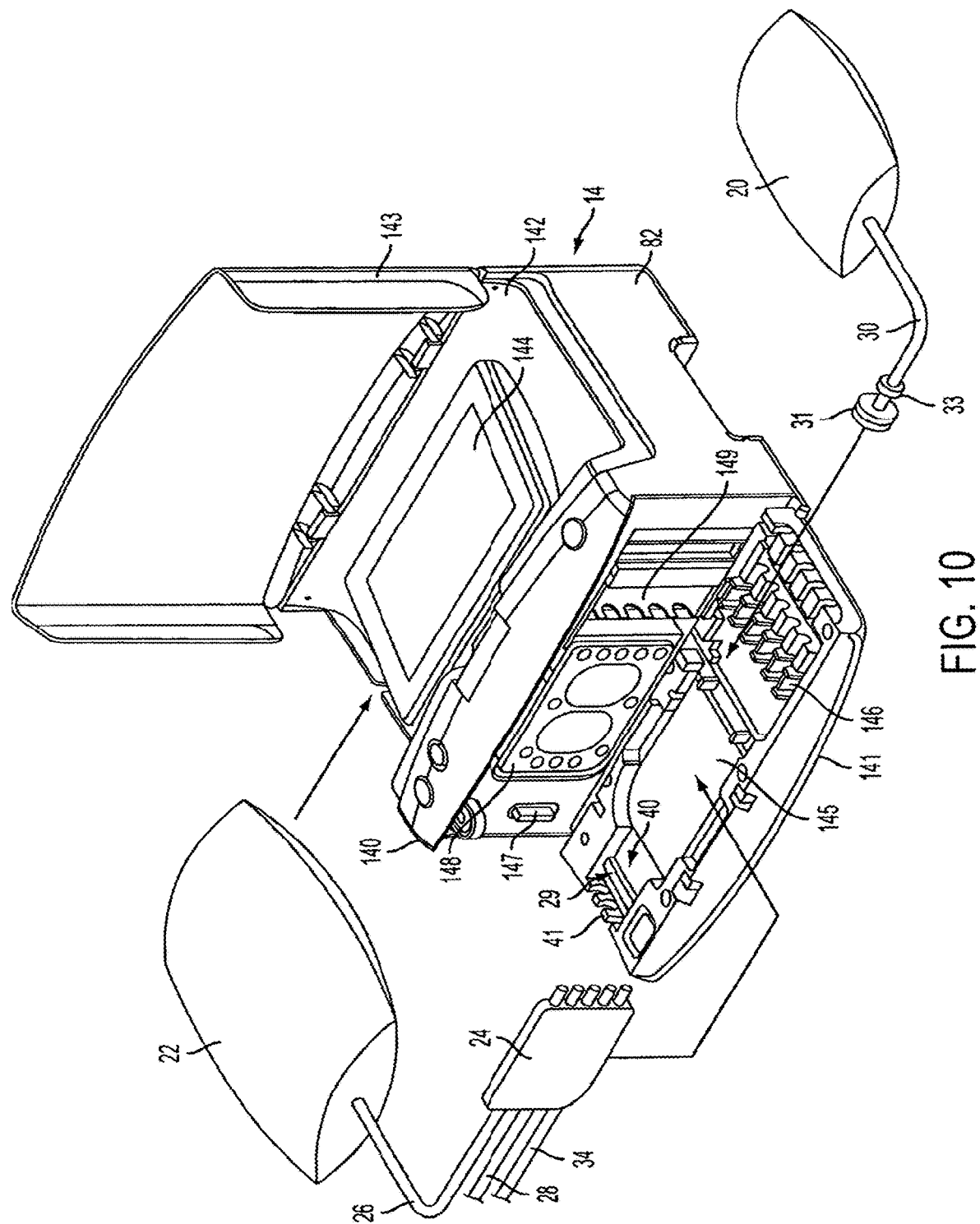
FIG. 10 is a perspective view of the APD system of FIG. 1 with the door of the cycler in an open position.

FIG. 10 shows a perspective view of the APD system 10 of FIG. 1 with the door 141 of the cycler 14 lowered into an open position, exposing a mounting location 145 for the cassette 24 and a carriage 146 for the solution lines 30. (In this embodiment, the door 141 is mounted by a hinge at a lower part of the door 141 to the cycler housing 82.) When loading the set 12, the cassette 24 is placed in the mounting location 145 with the membrane 15 and the pump chamber side of the cassette 24 facing upwardly, allowing the portions of the membrane 15 associated with the pump chambers and the valve ports to interact with a control surface 148 of the cycler 14 when the door 141 is closed. The mounting location 145 may be shaped so as to match the shape of the base member 18, thereby ensuring proper orientation of the cassette 24 in the mounting location 145. In this illustrative embodiment, the cassette 24 and mounting location 145 have a generally rectangular shape with a single larger radius corner which requires the user to place the cassette 24 in a proper orientation into the mounting location 145 or the door 141 will not close. It should be understood, however, that other shapes or orientation features for the cassette 24 and/or the mounting location 145 are possible.

In accordance with an aspect of the invention, when the cassette 24 is placed in the mounting location 145, the patient, drain and heater bag lines 34, 28 and 26 are routed through a channel 40 in the door 141 to the left as shown in FIG. 10. The channel 40, which may include guides 41 or other features, may hold the patient, drain and heater bag lines 34, 28 and 26 so that an occluder 147 may selectively close/open the lines for flow. Upon closing of door 141, occluder 147 can compress one or more of patient, drain and heater bag lines 34, 28 and 26 against occluder stop 29. Generally, the occluder 147 may allow flow through the lines 34, 28 and 26 when the cycler 14 is operating (and operating properly), yet occlude the lines when the cycler 14 is powered down (and/or not operating properly). (Occlusion of the lines may be performed by pressing on the lines, or otherwise pinching the lines to close off the flow path in the lines.) Preferably, the occluder 147 may selectively occlude at least the patient and drain lines 34 and 28.

When the cassette 24 is mounted and the door 141 is closed, the pump chamber side of the cassette 24 and the membrane 15 may be pressed into contact with the control surface 148, e.g., by an air bladder, spring or other suitable arrangement in the door 141 behind the mounting location 145 that squeezes the cassette 24 between the mounting location 145 and the control surface 148. This containment of the cassette 24 may press the membranes 15 and 16 into contact with walls and other features of the base member 18, thereby isolating channels and other flow paths of the cassette 24 as desired. The control surface 148 may include a flexible gasket, e.g., a sheet of silicone rubber or other material, that is associated with the membrane 15 and can selectively move portions of the membrane 15 to cause pumping action in the pump chambers 181 and opening/ closing of valve ports of the cassette 24. The control surface 148 may be associated with the various portions of the membrane 15, e.g., placed into intimate contact with each other, so that portions of the membrane 15 move in response to movement of corresponding portions of the control surface 148. For example, the membrane 15 and control surface 148 may be positioned close together, and a suitable vacuum (or pressure that is lower relative to ambient) may be introduced through vacuum ports suitably located in the control surface 148, and maintained, between the membrane 15 and the control surface 148 so that the membrane 15 and the control surface 148 are essentially stuck together, at least in regions of the membrane 15 that require movement to open/close valve ports and/or to cause pumping action. In another embodiment, the membrane 15 and control surface 148 may be adhered together, or otherwise suitably associated.

Before closing the door 141 with the cassette 24 loaded, one or more solution lines 30 may be loaded into the carriage 146. The end of each solution line 30 may include a cap 31 and a region 33 for labeling or attaching an indicator or identifier. The indicator, for example, can be an identification tag that snaps onto the tubing at indicator region 33. In accordance with an aspect of the invention and as will be discussed in more detail below, the carriage 146 and other components of the cycler 14 may be operated to remove the cap(s) 31 from lines 30, recognize the indicator for each line 30 (which may provide an indication as to the type of solution associated with the line, an amount of solution, etc.) and fluidly engage the lines 30 with a respective spike 160 of the cassette 24. This process may be done in an automated way, e.g., after the door 141 is closed and the caps 31 and spikes 160 are enclosed in a space protected from human touch, potentially reducing the risk of contamination of the lines 30 and/or the spikes 160 when connecting the two together. For example, upon closing of the door 141, the indicator regions 33 may be assessed (e.g., visually by a suitable imaging device and software-based image recognition, by RFID techniques, etc.) to identify what solutions are associated with which lines 30. The aspect of the invention regarding the ability to detect features of a line 30 by way of an indicator at indicator region 33 may provide benefits such as allowing a user to position lines 30 in any location of the carriage 146 without having an affect on system operation. That is, since the cycler 14 can automatically detect solution line features, there is no need to ensure that specific lines are positioned in particular locations on the carriage 146 for the system to function properly. Instead, the cycler 14 may identify which lines 30 are where, and control the cassette 24 and other system features appropriately. For example, one line 30 and connected container may be intended to receive used dialysate, e.g., for later testing. Since the cycler 14 can identify the presence of the sample supply line 30, the cycler 14 can route used dialysate to the appropriate spike 160 and line 30. As discussed above, since the spikes 160 of the cassette 24 all feed into a common channel, the input from any particular spike 160 can be routed in the cassette 24 in any desired way by controlling valves and other cassette features.

With lines 30 mounted, the carriage 146 may be moved to the left as shown in FIG. 10 (again, while the door 141 is closed), positioning the caps 31 over a respective spike cap 63 on a spike 160 of the cassette 24 and adjacent a cap stripper 149. The cap stripper 149 may extend outwardly (toward the door 141 from within a recess in the cycler 14 housing) to engage the caps 31. (For example, the cap stripper 149 may include five fork-shaped elements that engage with a corresponding groove in the caps 31, allowing the cap stripper 149 to resist left/right movement of the cap 31 relative to the cap stripper 149.) By engaging the caps 31 with the cap stripper 149, the caps 31 may also grip the corresponding spike cap 63. Thereafter, with the caps 31 engaged with corresponding spike caps 63, the carriage 146 and cap stripper 149 may move to the right, removing the spike caps 63 from the spikes 160 that are engaged with a corresponding cap 31. (One possible advantage of this arrangement is that spike caps 63 are not removed in locations where no solution line 30 is loaded because engagement of the cap 31 from a solution line 30 is required to remove a spike cap 63. Thus, if a solution line will not be connected to a spike 160, the cap on the spike 160 is left in place.) The cap stripper 149 may then stop rightward movement (e.g., by contacting a stop), while the carriage 146 continues movement to the right. As a result, the carriage 146 may pull the terminal ends of the lines 30 from the caps 31, which remain attached to the cap stripper 149. With the caps 31 removed from the lines 30 (and the spike caps 63 still attached to the caps 31), the cap stripper 149 may again retract with the caps 31 into the recess in the cycler 14 housing, clearing a path for movement of the carriage 146 and the uncapped ends of the lines 30 toward the spikes 160. The carriage 146 then moves left again, attaching the terminal ends of the lines 30 with a respective spike 160 of the cassette 24. This connection may be made by the spikes 160 piercing an otherwise closed end of the lines 30 (e.g., the spikes may pierce a closed septum or wall in the terminal end), permitting fluid flow from the respective containers 20 to the cassette 24. In an embodiment, the wall or septum may be constructed of a flexible and/or self-sealing material such as, for example, PVC, polypropylene, or silicone rubber.

In accordance with an aspect of the invention, the heater bag 22 may be placed in the heater bag receiving section (e.g., a tray) 142, which is exposed by lifting a lid 143. (In this embodiment, the cycler 14 includes a user or operator interface 144 that is pivotally mounted to the housing 82, as discussed below. To allow the heater bag 22 to be placed into the tray 142, the interface 144 may be pivoted upwardly out of the tray 142.) As is known in the art, the heater tray 142 may heat the dialysate in the heater bag 22 to a suitable temperature, e.g., a temperature appropriate for introduction into the patient. In accordance with an aspect of the invention, the lid 143 may be closed after placement of the heater bag 22 in the tray 142, e.g., to help trap heat to speed the heating process, and/or help prevent touching or other contact with a relatively warm portion of the heater tray 142, such as its heating surfaces. In one embodiment, the lid 143 may be locked in a closed position to prevent touching of heated portions of the tray 142, e.g., in the circumstance that portions of the tray 142 are heated to temperatures that may cause burning of the skin. Opening of the lid 143 may be prevented, e.g., by a lock, until temperatures under the lid 143 are suitably low.

In accordance with another aspect of the invention, the cycler 14 includes a user or operator interface 144 that is pivotally mounted to the cycler 14 housing and may be folded down into the heater tray 142. With the interface 144 folded down, the lid 143 may be closed to conceal the interface 144 and/or prevent contact with the interface 144. The interface 144 may be arranged to display information, e.g., in graphical form, to a user, and receive input from the user, e.g., by using a touch screen and graphical user interface. The interface 144 may include other input devices, such as buttons, dials, knobs, pointing devices, etc. With the set 12 connected, and containers 20 appropriately placed, the user may interact with the interface 144 and cause the cycler 14 to start a treatment and/or perform other functions.

However, prior to initiating a dialysis treatment cycle, the cycler 14 must at least prime the cassette 24, the patient line 34, heater bag 22, etc., unless the set 12 is provided in a pre-primed condition (e.g., at the manufacturing facility or otherwise before being put into use with the cycler 14). Priming may be performed in a variety of ways, such as controlling the cassette 24 (namely the pumps and valves) to draw liquid from one or more solution containers 20 via a line 30 and pump the liquid through the various pathways of the cassette 24 so as to remove air from the cassette 24. Dialysate may be pumped into the heater bag 22, e.g., for heating prior to delivery to the patient. Once the cassette 24 and heater bag line 26 are primed, the cycler 14 may next prime the patient line 34. In one embodiment, the patient line 34 may be primed by connecting the line 34 (e.g., by the connector 36) to a suitable port or other connection point on the cycler 14 and causing the cassette 24 to pump liquid into the patient line 34. The port or connection point on the cycler 14 may be arranged to detect the arrival of liquid at the end of the patient line (e.g., optically, by conductive sensor, or other), thus detecting that the patient line is primed. As discussed above, different types of sets 12 may have differently sized patient lines 34, e.g., adult or pediatric size. In accordance with an aspect of the invention, the cycler 14 may detect the type of cassette 24 (or at least the type of patient line 34) and control the cycler 14 and cassette 24 accordingly. For example, the cycler 14 may determine a volume of liquid delivered by a pump in the cassette needed to prime the patient line 34, and based on the volume, determine the size of the patient line 34. Other techniques may be used, such as recognizing a barcode or other indicator on the cassette 24, patient line 34 or other component that indicates the patient line type.

Figure 11:
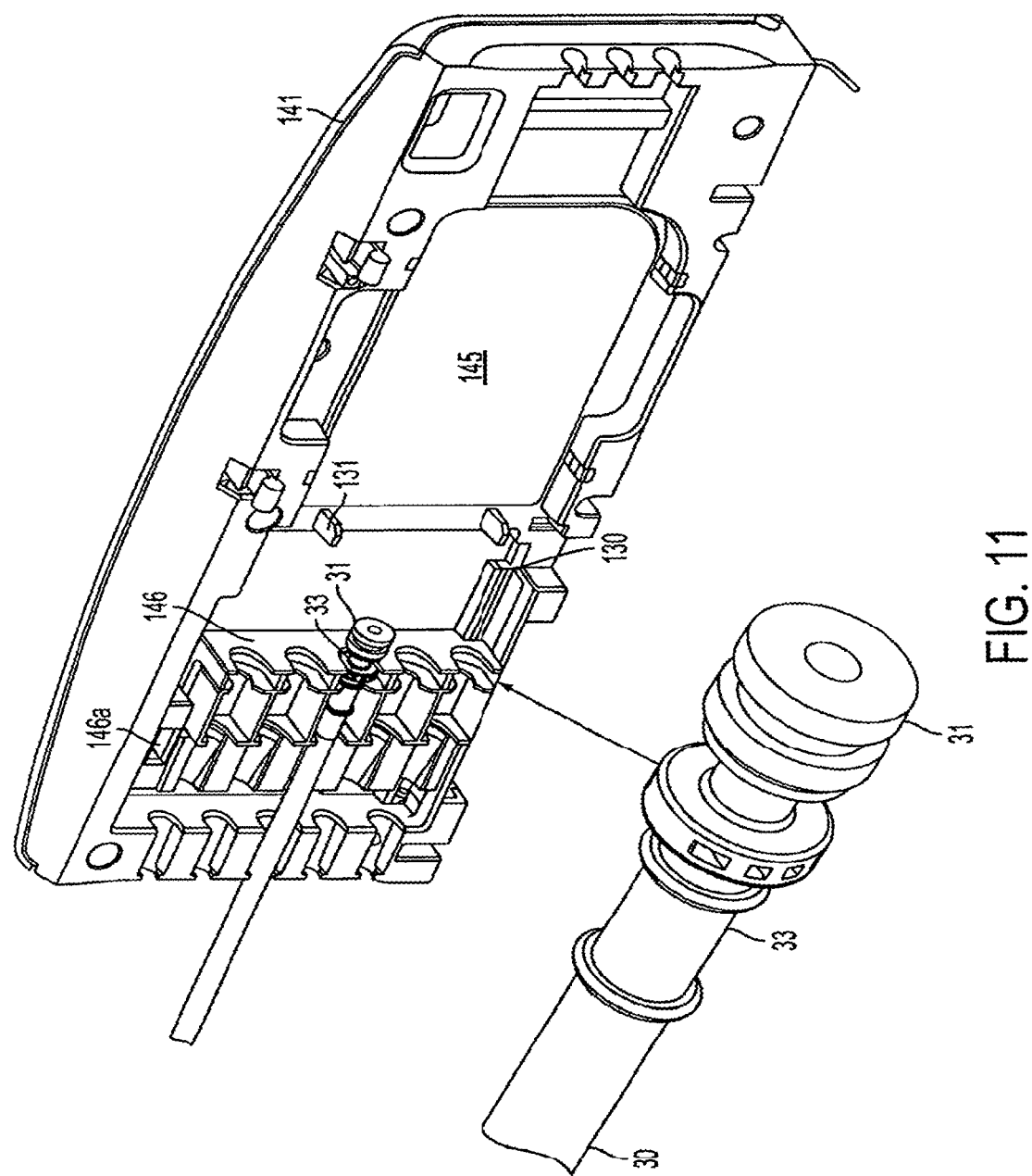
FIG. 11 is a perspective view of the inner side of the door of the cycler show in FIG. 10.

FIG. 11 shows a perspective view of the inner side of the door 141 disconnected from the housing 82 of the cycler 14. This view more clearly shows how the lines 30 are received in corresponding grooves in the door 141 and the carriage 146 such that the indicator region 33 is captured in a specific slot of the carriage 146. With the indicator at indicator region 33 positioned appropriately when the tubing is mounted to the carriage 146, a reader or other device can identify indicia of the indicator, e.g., representing a type of solution in the container 20 connected to the line 30, an amount of solution, a date of manufacture, an identity of the manufacturer, and so on. The carriage 146 is mounted on a pair of guides 130 at top and bottom ends of the carriage 146 (only the lower guide 130 is shown in FIG. 11). Thus, the carriage 146 can move left to right on the door 141 along the guides 130. When moving toward the cassette mounting location 145 (to the right in FIG. 11), the carriage 146 can move until it contacts stops 131.

Figure 12:
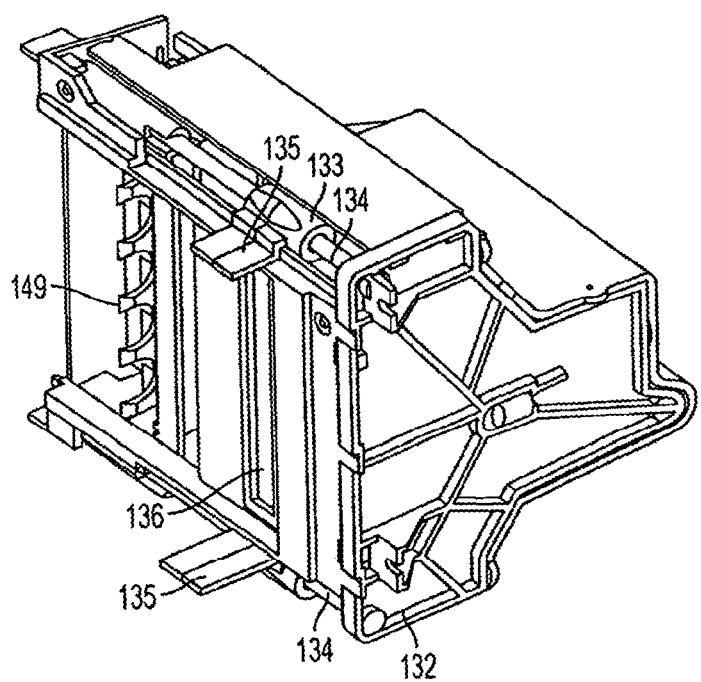
FIG. 12 is a right front perspective view of a carriage drive assembly and cap stripper in a first embodiment.

FIG. 12 shows a perspective view of a carriage drive assembly 132 in a first embodiment that functions to move the carriage 146 to remove the caps from spikes 160 on the cassette, remove caps 31 on the solution lines 30 and connect lines 30 to the spikes 160. A drive element 133 is arranged to move left to right along rods 134. In this illustrative embodiment, an air bladder powers the movement of the drive element 133 along the rods 134, but any suitable drive mechanism may be used, including motors, hydraulic systems, etc. The drive element 133 has forwardly extending tabs 135 that engage with corresponding slots 146*a* on the carriage 146 (see FIG. 11, which shows a top slot 146a on the carriage 146). Engagement of the tabs 135 with the slots 146a allow the drive element 133 to move the carriage 146 along the guides 130. The drive element 133 also includes a window 136, through which an imaging device, such as a CCD or CMOS imager, may capture image information of the indicators at indicator regions 33 on the lines 30 mounted to the carriage 146. Image information regarding the indicators at indicator regions 33 may be provided from the imaging device to the control system 16, which may obtain indicia, e.g., by image analysis. The drive element 133 can selectively move the cap stripper 149 both to the left and right along the rods 134. The cap stripper 149 extends forward and back using a separate drive mechanism, such as a pneumatic bladder.

Figure 13:
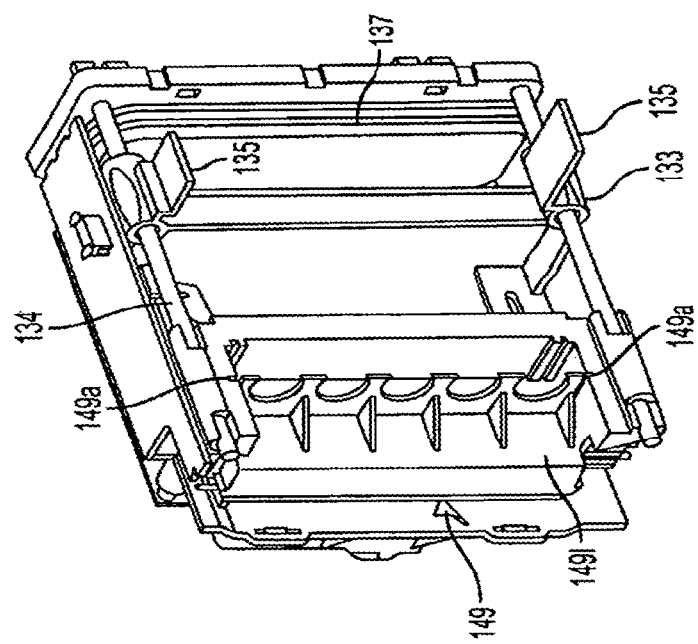
FIG. 13 a left front perspective view of the carriage drive assembly and cap stripper of FIG. 12.
Figure 14:
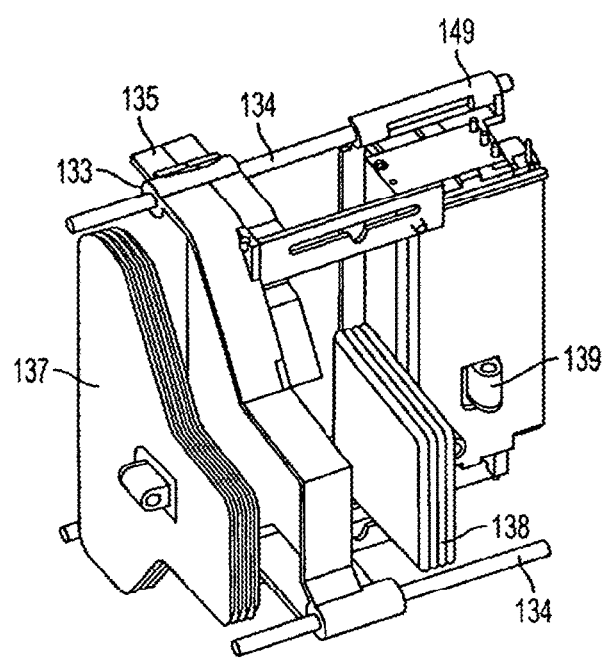
FIG. 14 is a partial rear view of the carriage drive assembly of FIG. 12.
Figure 15:
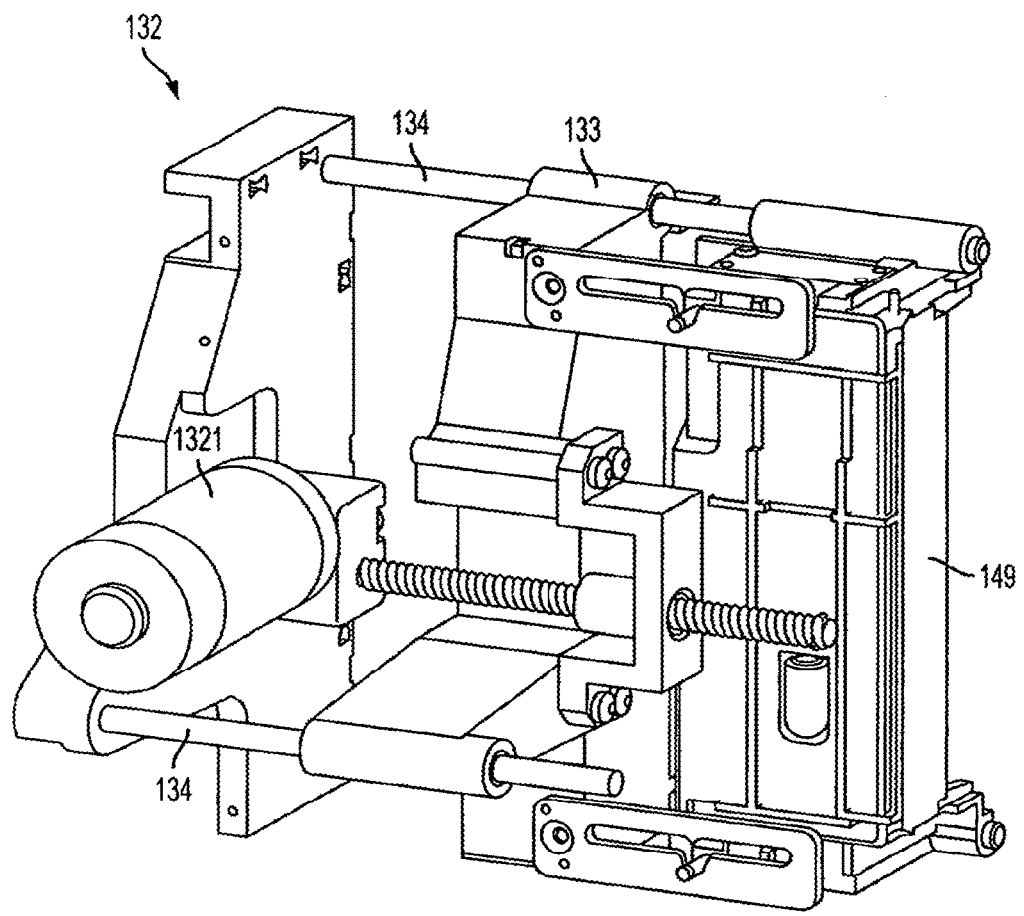
FIG. 15 is a rear perspective view of a carriage drive assembly in a second illustrative embodiment.
Figure 16:
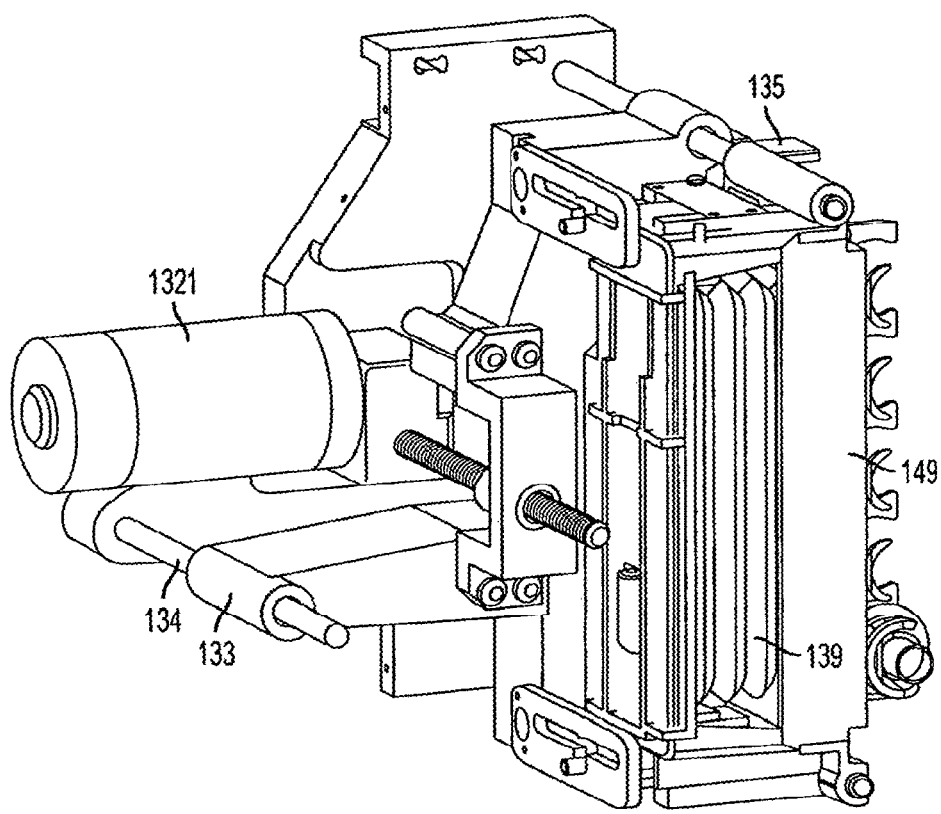
FIG. 16 is a left rear perspective view of the carriage drive assembly and cap stripper of FIG. 15.

FIG. 13 shows a left side perspective view of the carriage drive assembly 132, which more clearly shows how a stripper element of the cap stripper 149 is arranged to move in and out (a direction generally perpendicular to the rods 134) along grooves 149a in the housing of the cap stripper 149. Each of the semicircular cut outs of the stripper element may engage a corresponding groove of a cap 31 on a line 30 by extending forwardly when the cap 31 is appropriately positioned in front of the stripper 149 by the drive element 133 and the carriage 146. With the stripper element engaged with the caps 31, the cap stripper 149 may move with the carriage 146 as the drive element 133 moves. FIG. 14 shows a partial rear view of the carriage drive assembly 132. In this embodiment, the drive element 133 is moved toward the cassette 24 mounting location 145 by a first air bladder 137 which expands to force the drive element 133 to move to the right in FIG. 14. The drive element can be moved to the left by a second air bladder 138. Alternatively, drive element 133 can be moved back and forth by means of one or more motors coupled to a linear drive gear assembly, such as a ball screw assembly (in which the carriage drive assembly is attached to a ball nut), or a rack and pinion assembly, for example. The stripper element 1491 of the cap stripper 149 can be moved in and out of the cap stripper housing by a third bladder, or alternatively, by a motor coupled to a linear drive assembly, as described previously.

FIGS. 15-18 show another embodiment of a carriage drive assembly 132 and cap stripper 149. As can be seen in the rear view of the carriage drive assembly 132 in FIG. 15, in this embodiment the drive element 133 is moved right and left by a screw drive mechanism 1321. As can be seen in the right rear perspective view of the carriage drive assembly 132 in FIG. 16, the stripper element is moved outwardly and inwardly by an air bladder 139, although other arrangements are possible as described above.

Figure 18:
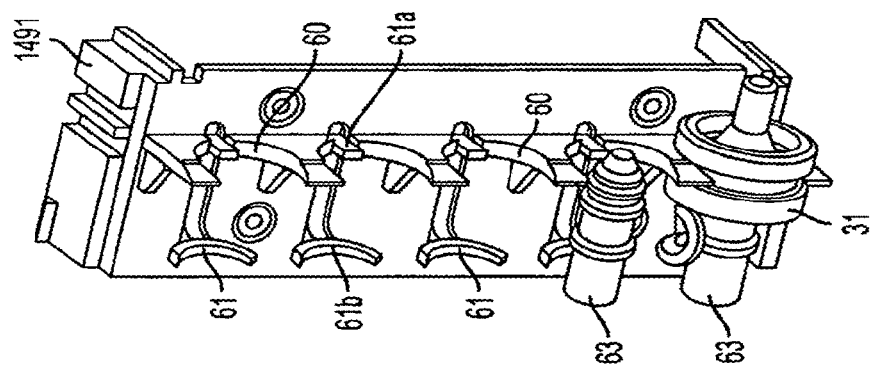
FIG. 18 is a right front perspective view of the cap stripper element of FIG. 17.
Figure 17:
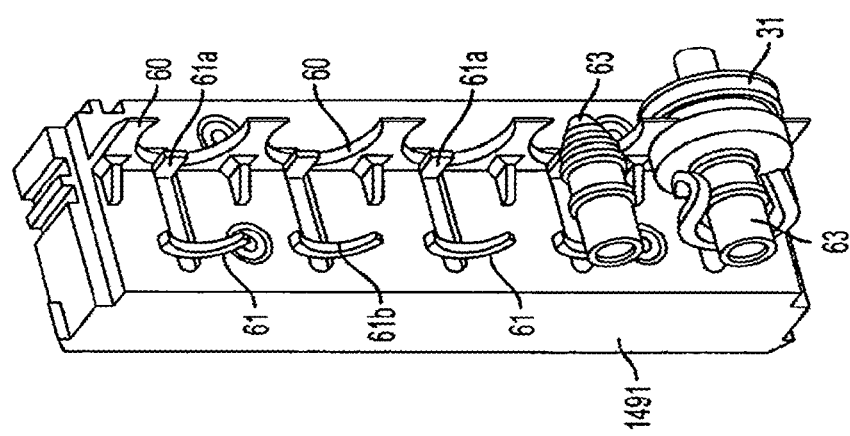
FIG. 17 is a left front perspective view of a cap stripper element in an illustrative embodiment.

FIGS. 17 and 18 show left and right front perspective views of another embodiment for the stripper element 1491 of the cap stripper 149. The stripper element 1491 in the embodiment shown in FIG. 13 included only fork-shaped elements arranged to engage with a cap 31 of a solution line 30. In the FIGS. 17 and 18 embodiment, the stripper element 1491 not only includes the fork-shaped elements 60, but also rocker arms 61 that are pivotally mounted to the stripper element 1491. As will be explained in more detail below, the rocker arms 61 assist in removing spike caps 63 from the cassette 24. Each of the rocker arms 61 includes a solution line cap engagement portion 61a and a spike cap engagement portion 61b. The rocker arms 61 are normally biased to move so that the spike cap engagement portions 61b are positioned near the stripper element 1491, as shown in the rocker arms 61 in FIG. 18. However, when a cap 31 is received by a corresponding fork-shaped element 60, the solution line cap engagement portion 61a contacts the cap 31, which causes the rocker arm 61 to pivot so that the spike cap engagement portion 61b moves away from the stripper element 1491, as shown in FIG. 17. This position enables the spike cap engagement portion 61b to contact a spike cap 63, specifically a flange on the spike cap 63.

Figure 19:
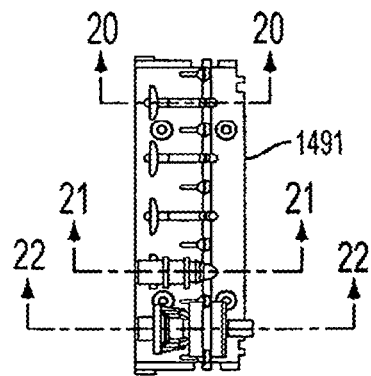
FIG. 19 is a front view of the cap stripper element of FIG. 17.
Figure 20:
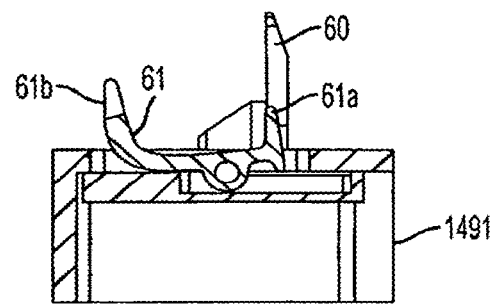
FIG. 20 is a cross sectional view along the line 20-20 in FIG. 19.
Figure 21:
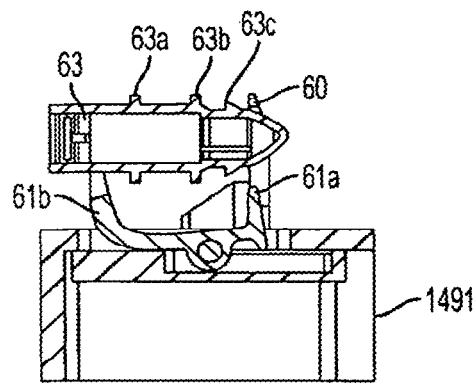
FIG. 21 is a cross sectional view along the line 21-21 in FIG. 19.
Figure 22:
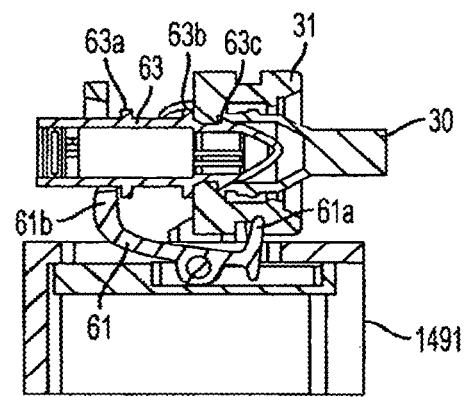
FIG. 22 is a cross sectional view along the line 22-22 in FIG. 19.

FIG. 19 shows a front view of the stripper element 1491 and the location of several cross-sectional views shown in FIGS. 20-22. FIG. 20 shows the rocker arm 61 with no spike cap 63 or solution line cap 31 positioned near the stripper element 1491. The rocker arm 61 is pivotally mounted to the stripper element 1491 at a point approximately midway between the spike cap engagement portion 61b and the solution cap engagement portion 61a. As mentioned above, the rocker arm 61 is normally biased to rotate in a counter-clockwise direction as shown in FIG. 20 so that the spike cap engagement portion 61b is positioned near the stripper element 1491. FIG. 21 shows that the rocker arm 61 maintains this position (i.e., with the spike cap engagement portion 61b located near the stripper element 1491) even when the stripper element 1491 advances toward a spike cap 63 in the absence of a solution line cap 31 engaging with the fork-shaped element 60. As a result, the rocker arm 61 will not rotate clockwise or engage the spike cap 63 unless a solution line cap 31 is present. Thus, a spike cap 63 that does not engage with a solution line cap 31 will not be removed from the cassette 24.

FIG. 22 shows an example in which a solution line cap 31 is engaged with the fork-shaped element 60 and contacts the solution line cap engagement portion 61a of the rocker arm 61. This causes the rocker arm 61 to rotate in a clockwise direction (as shown in the figure) and the spike cap engagement portion 61b to engage with the spike cap 63. In this embodiment, engagement of the portion 61b includes positioning the portion 61b adjacent a second flange 63a on the spike cap 63 so that when the stripper element 1491 moves to the right (as shown in FIG. 22), the spike cap engagement portion 61b will contact the second flange 63a and help pull the spike cap 63 from the corresponding spike 160. Note that the solution line cap 31 is made of a flexible material, such as silicone rubber, to allow a barb 63c of the spike cap 63 to stretch the hole 31b of cap 31 (see FIG. 23) and be captured by a circumferential inner groove or recess within cap 31. A first flange 63b on the spike cap 63 acts as a stop for the end of solution line cap 31. The walls defining the groove or recess in the cap 31 hole 31b may be symmetrical, or preferably asymmetrically arranged to conform to the shape of the barb 63c. (See FIG. 33 for a cross sectional view of the cap 31 and the groove or recess.) The second flange 63a on spike cap 63 acts as a tooth with which the spike cap engagement portion 61b of the rocker arm 61 engages in order to provide an additional pulling force to disengage the spike cap 63 from the spike 160, if necessary.

Figure 23:
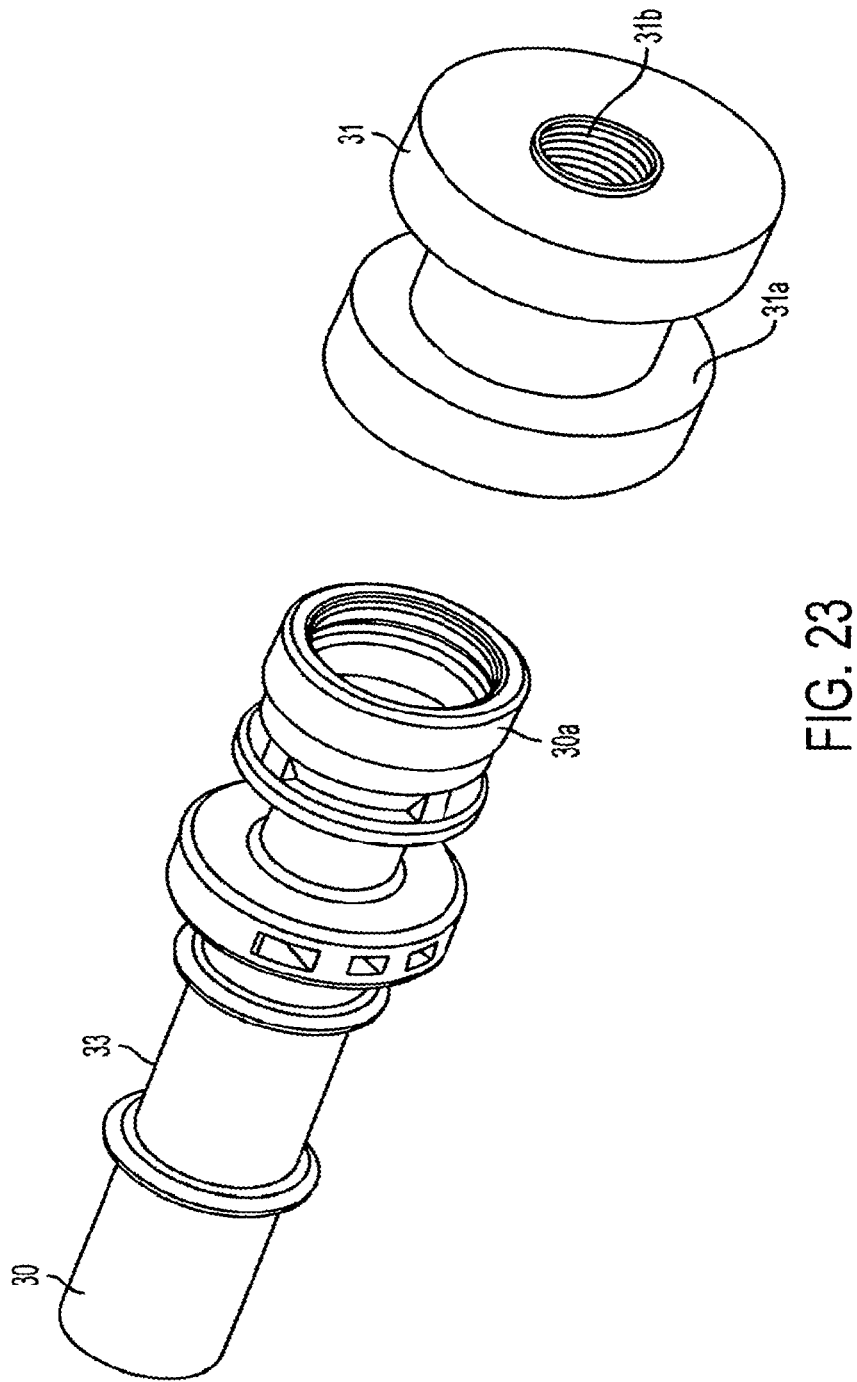
FIG. 23 is a close-up exploded view of the connector end of a solution line in an illustrative embodiment.

FIG. 23 shows a close-up exploded view of the connector end 30a of a solution line 30 with the cap 31 removed. (In FIG. 23, the caps 31 are shown without a finger pull ring like that shown in FIG. 24 for clarity. A pull ring need not be present for operation of the cap 31 with the cycler 14. It may be useful, however, in allowing an operator to manually remove the cap 31 from the terminal end of solution line 30, if necessary). In this illustrative embodiment, the indicator at indicator region 33 has an annular shape that is sized and configured to fit within a corresponding slot of the carriage 146 when mounted as shown in FIGS. 10 and 11. Of course, the indicator may take any suitable form. The cap 31 is arranged to fit over the extreme distal end of the connector end 30a, which has an internal bore, seals, and/or other features to enable a leak-free connection with a spike 160 on a cassette 24. The connector end 30*a* may include a pierceable wall or septum (not shown—see FIG. 33 item 30*b*) that prevents leakage of solution in the line 30 from the connector end 30*a*, even if the cap 31 is removed. The wall or septum may be pierced by the spike 160 when the connector end 30*a* is attached to the cassette 24, allowing flow from the line 30 to the cassette 24. As discussed above, the cap 31 may include a groove 31*a* that is engaged by a fork-shaped element 60 of the cap stripper 149. The cap 31 may also include a hole 31*b* that is arranged to receive a spike cap 63. The hole 31*b* and the cap 31 may be arranged so that, with the cap stripper 149 engaged with the groove 31*a* and the spike cap 63 of a spike 160 received in the hole 31*b*, the cap 31 may grip the spike cap 63 suitably so that when the carriage 146/cap stripper 149 pulls the cap 31 away from the cassette 24, the spike cap 63 is removed from the spike 160 and is carried by the cap 31. This removal may be assisted by the rocker arm 61 engaging with the second flange 63*a* or other feature on the spike cap 63, as described above. Thereafter, the cap 31 and spike cap 63 may be removed from the connector end 30*a* and the line 30 attached to the spike 160 by the carriage 146.

Once treatment is complete, or the line 30 and/or the cassette 24 are ready for removal from cycler 14, the cap 31 and attached spike cap 63 may be re-mounted on the spike 160 and the line 30 before the door 141 is permitted to be opened and the cassette 24 and line 30 removed from the cycler 14. Alternatively, the cassette 24 and solution containers with lines 30 can be removed en bloc from cycler 14 without re-mounting cap 31 and the attached spike cap 63. An advantage of this approach includes a simplified removal process, and avoidance of any possible fluid leaks onto the cycler or surrounding area from improperly re-mounted or inadequately sealing caps.

Figure 24:
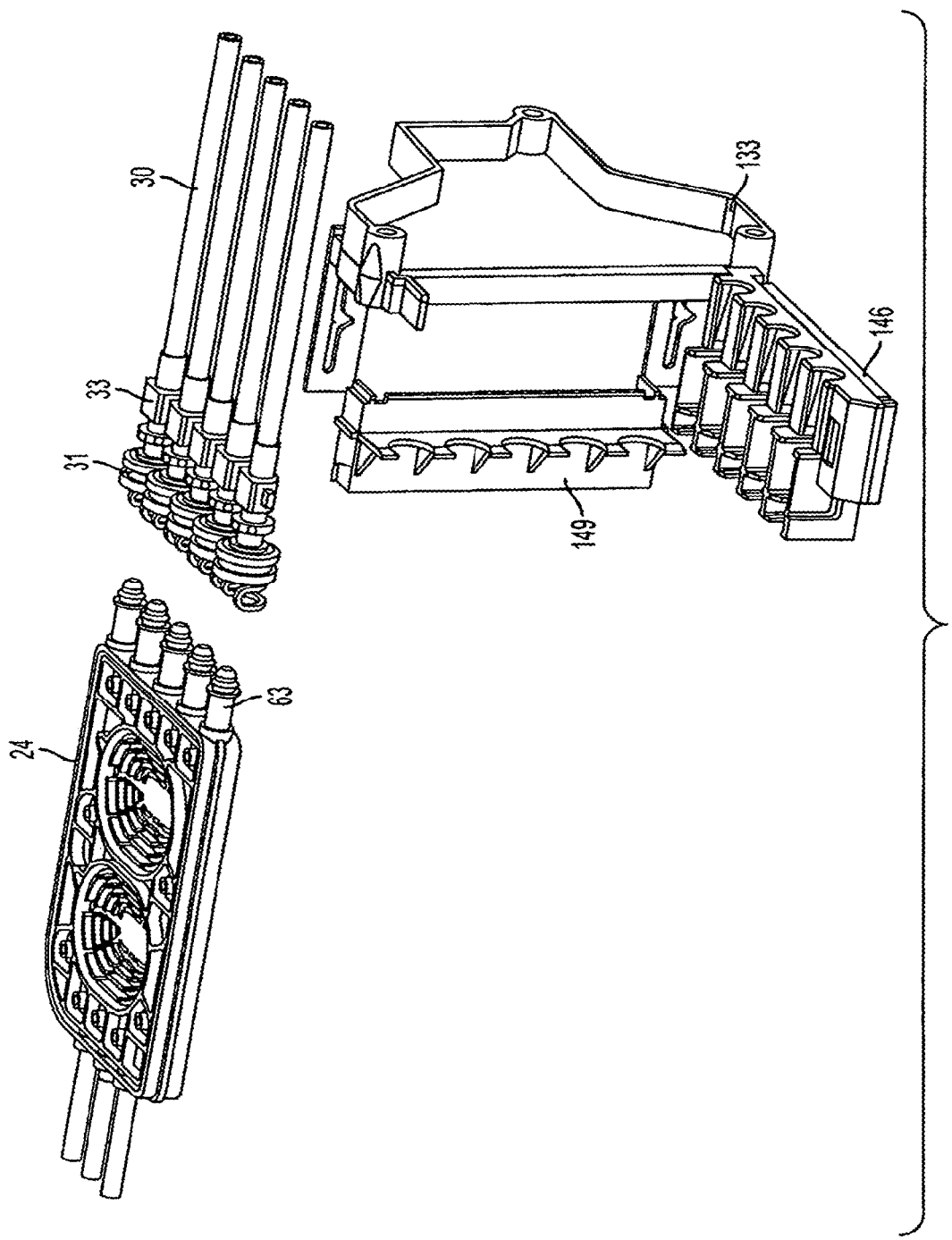
FIG. 24 is a schematic view of a cassette and solution lines being loaded into the cycler of FIG. 10.
Figure 25:
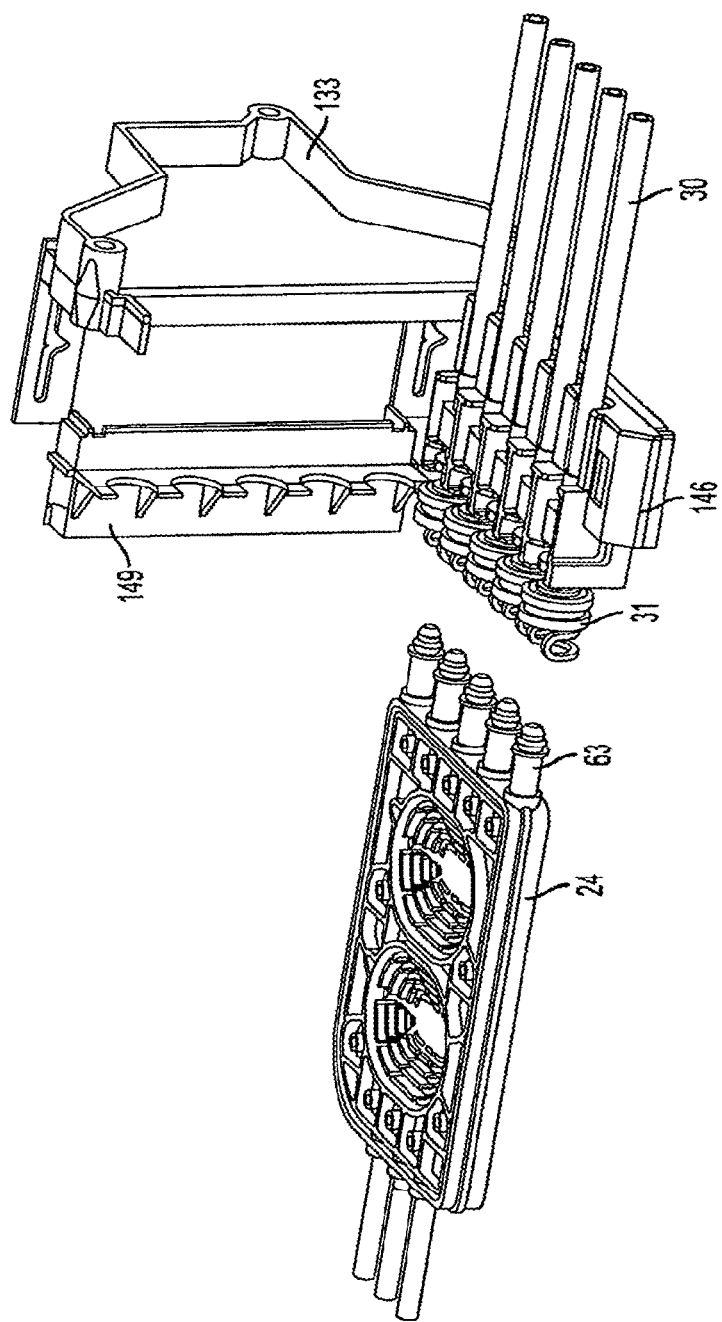
FIG. 25 is a schematic view of the cassette and solution lines after placement in respective locations of the door of the cycler of FIG. 10.
Figure 26:
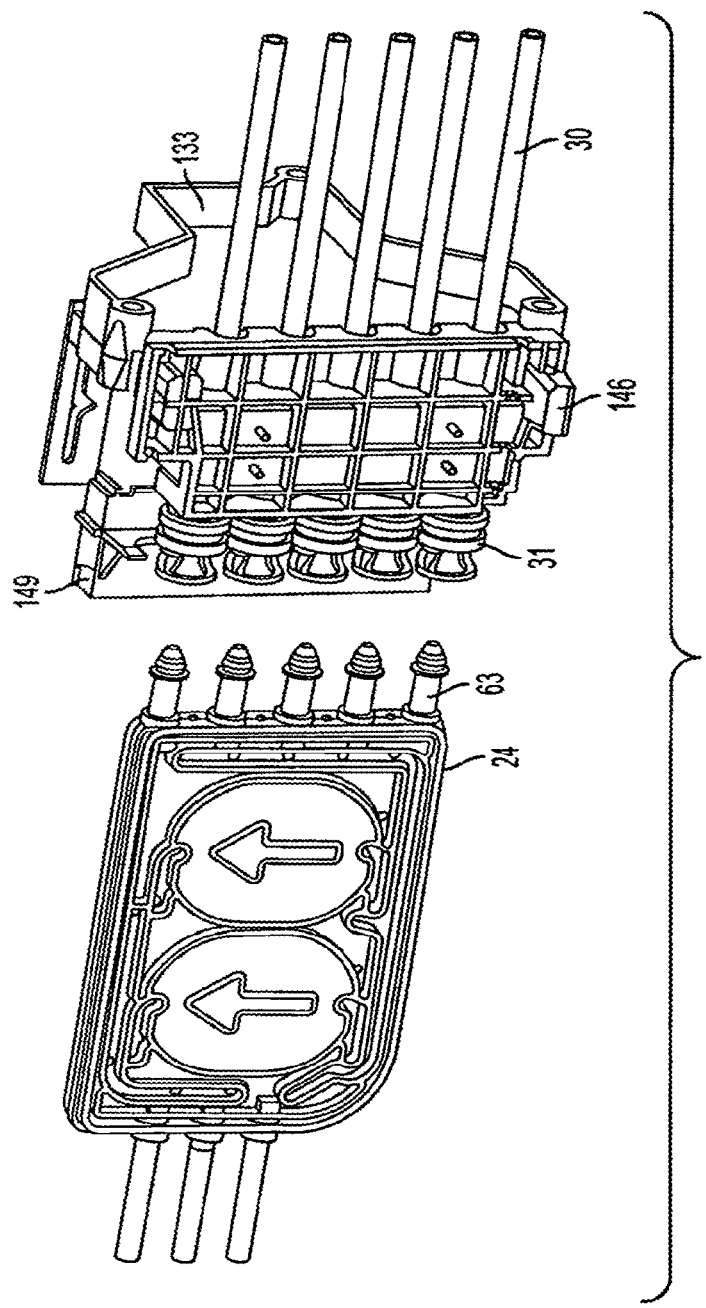
FIG. 26 is a schematic view of the cassette and solution lines after the door of the cycler is closed.
Figure 27:
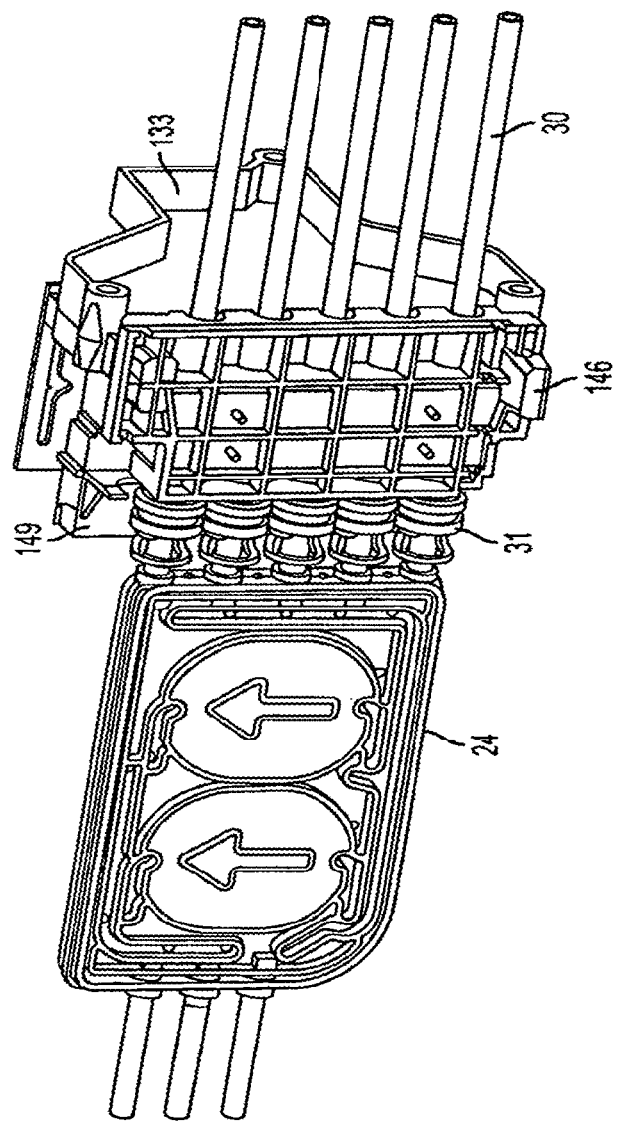
FIG. 27 is a schematic view of the solution lines being engaged with spike caps.
Figure 28:
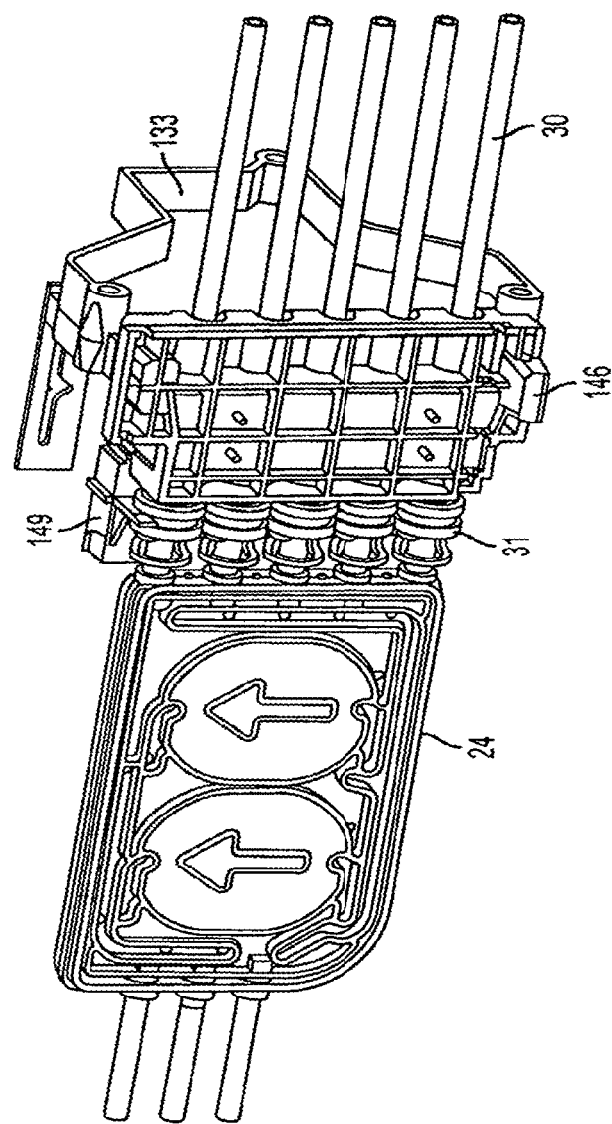
FIG. 28 is a schematic view of the cap stripper engaging with spike caps and solution line caps.
Figure 29:
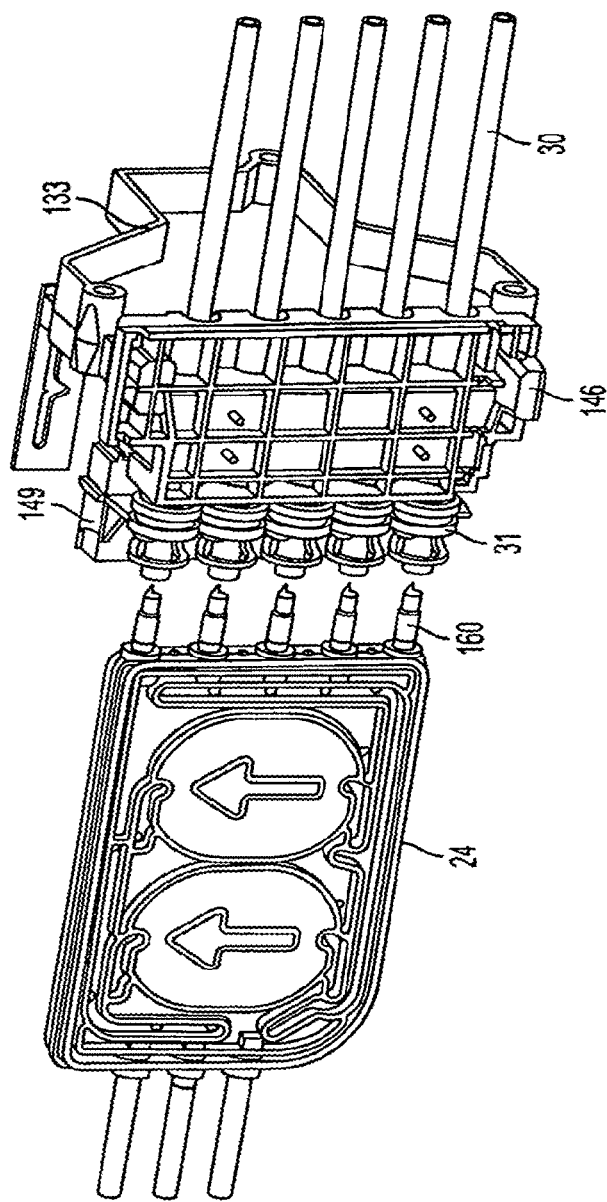
FIG. 29 is a schematic view of the solution lines with attached caps and spike caps after movement away from the cassette.
Figure 30:
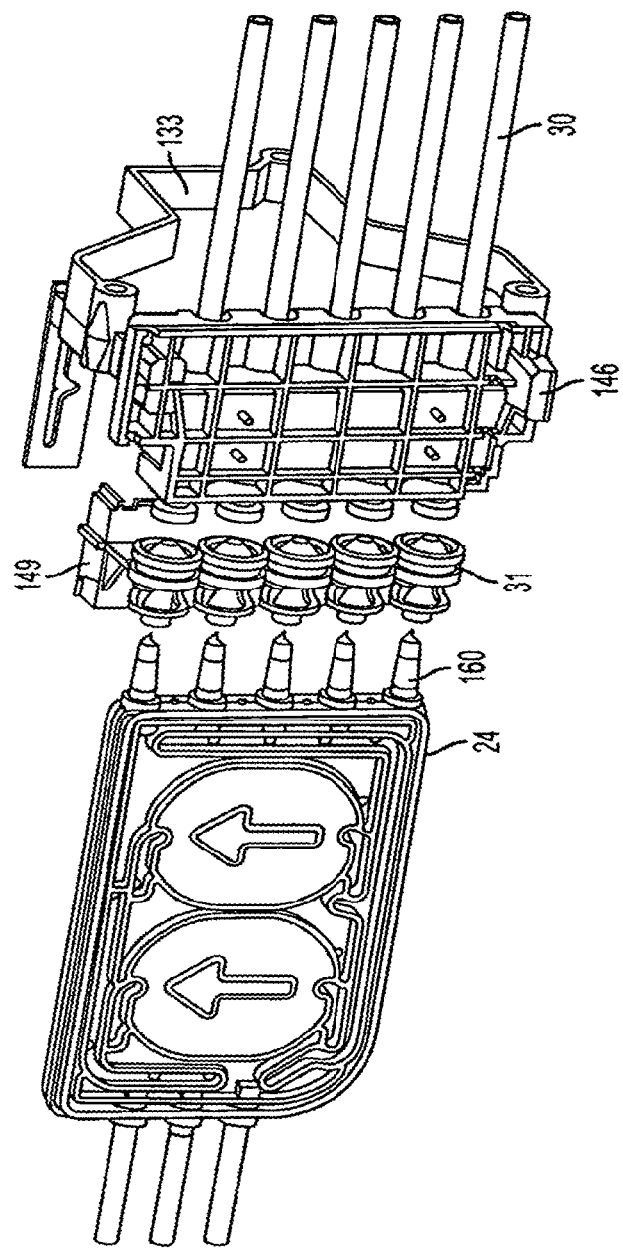
FIG. 30 is a schematic view of the solution lines after movement away from the solution line caps and spike caps.
Figure 31:
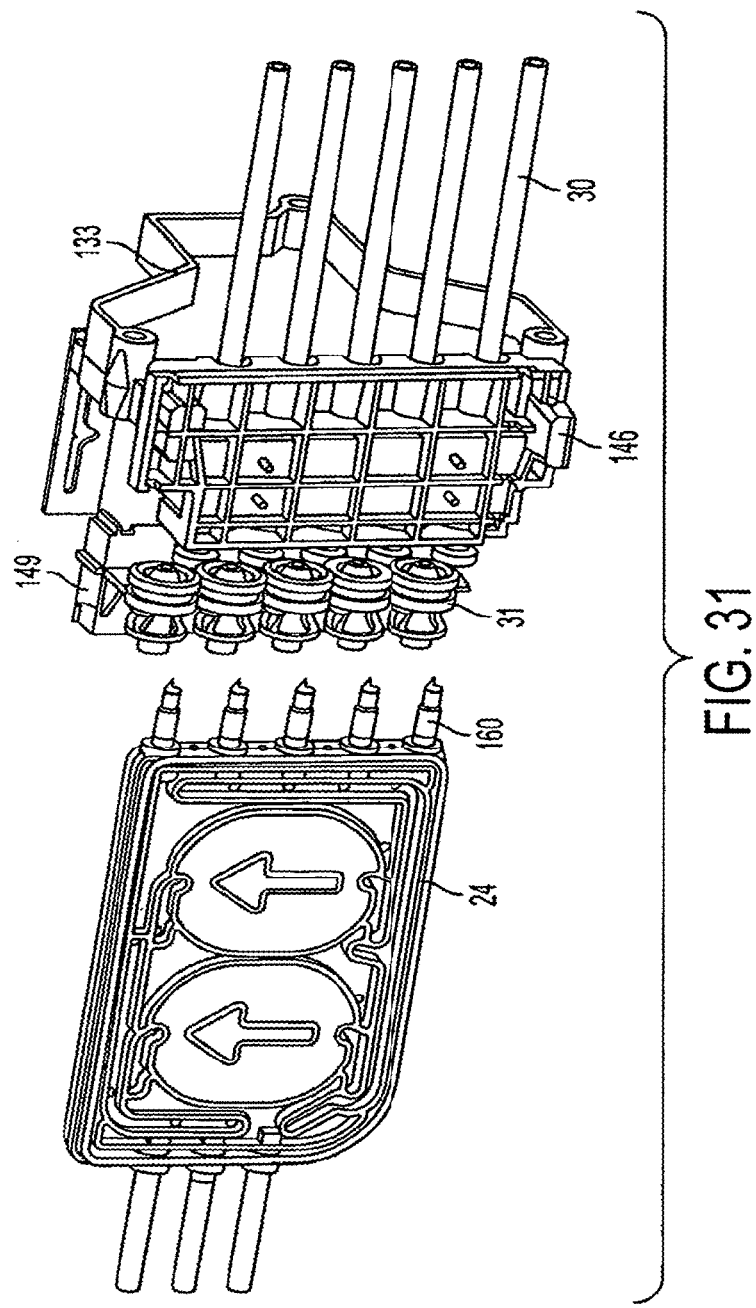
FIG. 31 is a schematic view of the cap stripper retracting with the solution line caps and spike caps.
Figure 32:
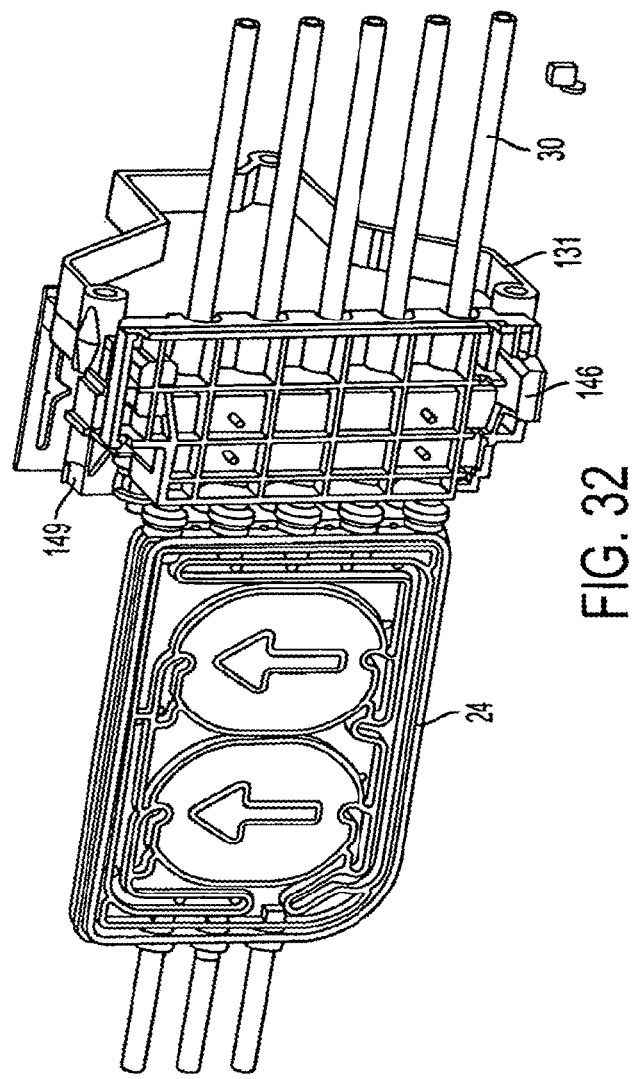
FIG. 32 is a schematic view of the solution lines being engaged with the spikes of the cassette.

FIGS. 24-32 show a perspective view of the carriage 146, cap stripper 149 and cassette 24 during a line mounting and automatic connection operation. The door 141 and other cycler components are not shown for clarity. In FIG. 24, the carriage 146 is shown in a folded down position, as if the door 141 is open in the position shown in FIG. 0.8. The lines 30 and cassette 24 are positioned to be lowered onto the door 141. In FIG. 25, the lines 30 are loaded into the carriage 146 and the cassette 24 is loaded into the mounting location 145. At this point the door 141 can be closed to ready the cycler for operation. In FIG. 26, the door 141 is closed. Identifiers or indicators located at indicator region 33 on the lines 30 may be read to identify various line characteristics so that the cycler 14 can determine what solutions, how much solution, etc., are loaded. In FIG. 27, the carriage 146 has moved to the left, engaging the caps 31 on the lines 30 with corresponding spike caps 63 on the cassette 24. During the motion, the drive element 133 engages the cap tripper 149 and moves the cap stripper 149 to the left as well. However, the cap stripper 149 remains in a retracted position. In FIG. 28, the cap stripper 149 moves forward to engage the fork-shaped elements 60 with the caps 31, thereby engaging the caps 31 that have been coupled to the spike caps 63. If present, the rocker arms 61 may move to an engagement position with respect to the spike caps 63. Next, as shown in FIG. 29, the carriage 146 and the cap stripper 149 move to the right, away from the cassette 24 so as to pull the caps 31 and spike caps 63 from the corresponding spikes 160 on the cassette 24. It is during this motion that the rocker arms 61, if present, may assist in pulling spike caps 63 from the cassette 24. In FIG. 30, the cap stripper 149 has stopped its movement to the right, while the carriage 146 continues to move away from the cassette 24. This causes the connector ends 30*a* of the lines 30 to be pulled from the caps 31, leaving the caps 31 and spike caps 63 mounted on the cap stripper 149 by way of the fork-shaped elements 60. In FIG. 31, the cap stripper 149 retracts, clearing a path for the carriage 146 to move again toward the cassette 24. In FIG. 32, the carriage 146 moves toward the cassette 24 to engage the connector ends 30*a* of the lines 30 with the corresponding spikes 160 of the cassette 24. The carriage 146 may remain in this position during cycler operation. Once treatment is complete, the movements shown in FIGS. 24-32 may be reversed to recap the spikes 160 and the solution lines 30 and remove the cassette 24 and/or lines 30 from the cycler 14.

Figure 33:
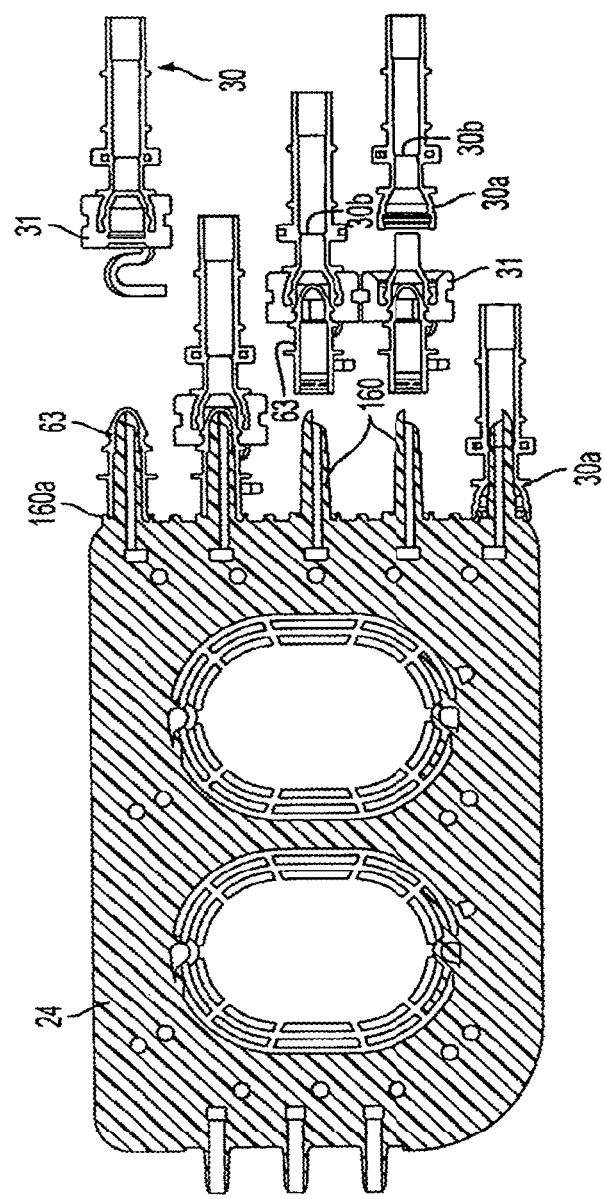
FIG. 33 is a cross sectional view of a cassette with five stages of a solution line connection operation shown with respect to corresponding spikes of the cassette.

To further illustrate the removal of caps 31 and spike caps 63, FIG. 33 shows a cross-sectional view of the cassette 24 at five different stages of line 30 connection. At the top spike 160, the spike cap 63 is still in place on the spike 160 and the solution line 30 is positioned away from the cassette 24, as in FIG. 26. At the second spike 160 down from the top, the solution line 30 and cap 31 are engaged over the spike cap 63, as in FIGS. 27 and 28. At this point, the cap stripper 149 may engage the cap 31 and spike cap 63. At the third spike 160 from the top, the solution line 30, cap 31 and spike cap 63 have moved away from the cassette 24, as in FIG. 29. At this point, the cap stripper 149 may stop movement to the right. At the fourth spike 160 from the top, the solution line 30 continues movement to the right, removing the cap 31 from the line 30, as in FIG. 30. Once the caps 31 and 63 are retracted, the solution line 30 moves to the left to fluidly connect the connector end 30*a* of the line 30 to the spike 160, as in FIG. 32.

Various sensors can be used to help verify that the carriage 146 and cap stripper 149 move fully to their expected positions. In an embodiment, the carriage drive assembly 132 can be equipped with six Hall effect sensors (not shown): four for the carriage 146 and two for the cap stripper 149. A first cap stripper sensor may be located to detect when the cap stripper 149 is fully retracted. A second cap stripper sensor may be located to detect when the cap stripper 149 is fully extended. A first carriage sensor may be located to detect when the carriage 146 is in the "home" position, i.e. in position to permit loading the cassette 24 and lines 30. A second carriage sensor may be located to detect when the carriage 146 is in position to have engaged the spike caps 63. A third carriage sensor may be located to detect when the carriage 146 has reached a position to have removed the caps 31 from the lines 30. A fourth carriage sensor may be located to detect when the carriage 146 has moved to a position to have engaged the connector ends 30*a* of the lines 30 with the corresponding spikes 160 of the cassette 24. In other embodiments, a single sensor can be used to detect more than one of the carriage positions described above. The cap stripper and carriage sensors can provide input signals to an electronic control board ("autoconnect board"), which in turn can communicate specific confirmation or error codes to the user via the user interface 144.

There may be an advantage in adjusting the force with which the carriage 146 engages the spike caps 63, depending on how many lines 30 are being installed. The force required to complete a connection to the cassette 24 increases with the number of caps 31 that must be coupled to spike caps 63. The sensing device for detecting and reading information from the line indicators at indicator regions 33 can also be used to provide the data required to adjust the force applied to drive element 133. The force can be generated by a number of devices, including, for example, the first air bladder 137, or a linear actuator such as a motor/ball screw.

An electronic control board (such as, for example, the autoconnect board) can be programmed to receive input from the line detection sensor(s), and send an appropriate control signal either to the motor of a linear actuator, or to the pneumatic valve that controls inflation of air bladder 137. The controller 16 can control the degree or rate of movement of drive element 133, for example by modulating the voltage applied to the motor of a linear actuator, or by modulating the pneumatic valve controlling the inflation of bladder 137.

The aspect of the invention by which caps 31 on lines 30 are removed together with caps 63 on spikes 160 of the cassette 24 may provide other advantages aside from simplicity of operation. For example, since spike caps 63 are removed by way of their engagement with a cap 31 on a line 30, if there is no line 30 mounted at a particular slot on the carriage 146, the spike cap 63 at that position will not be removed. For example, although the cassette 24 includes five spikes 160 and corresponding spike caps 63, the cycler 14 can operate with four or less (even no) lines 30 associated with the cycler 14. For those slots on the carriage 146 where no line 30 is present, there will be no cap 31, and thus no mechanism by which a spike cap 63 at that position can be removed. Thus, if no line 30 will be connected to a particular spike 160, the cap 63 on that spike 160 may remain in place during use of the cassette 24. This may help prevent leakage at the spike 160 and/or contamination at the spike 160.

Figure 34:
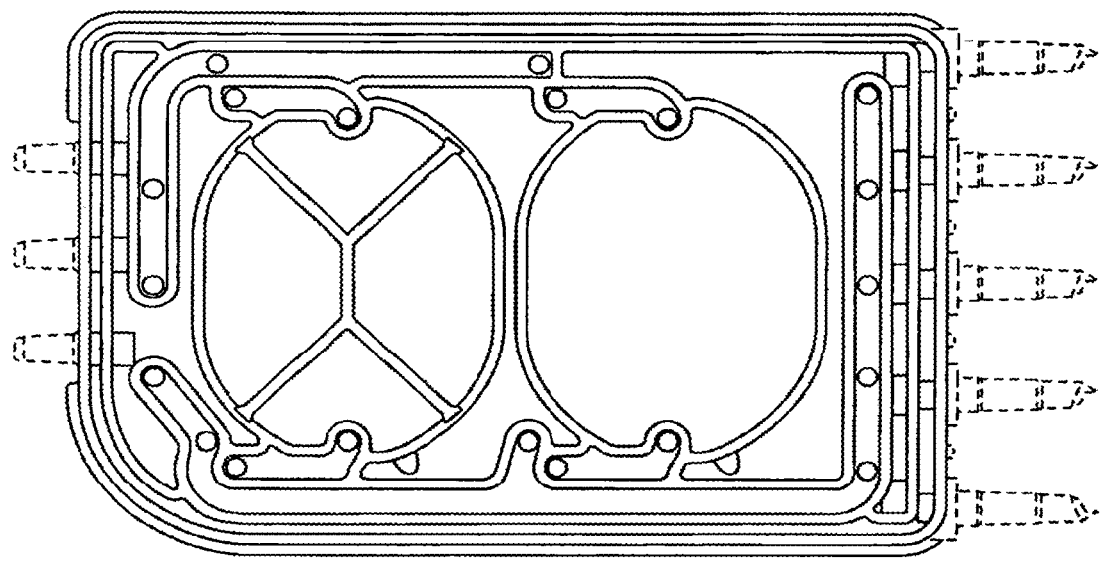
FIG. 34 shows a rear view of a cassette in another illustrative embodiment including different arrangements for a rear side of the cassette adjacent the pump chambers.

The cassette 24 in FIG. 33 includes a few features that are different from those shown, for example, in the embodiment shown in FIGS. 3, 4 and 6. In the FIGS. 3, 4 and 6 embodiment, the heater bag port 150, drain line port 152 and patient line port 154 are arranged to have a central tube 156 and a skirt 158. However, as mentioned above and shown in FIG. 33, the ports 150, 152, 154 may include only the central tube 156 and no skirt 158. This is also shown in FIG. 34. The embodiment depicted in FIG. 34 includes raised ribs formed on the outside surface of the left-side pump chamber 181. The raised ribs may also be provided on the right-side pump chamber 181, and may provide additional contact points of the outside walls of pump chambers 181 with the mechanism in the door 141 at the cassette mounting location 145, which presses the cassette against the control surface 148 when the door 141 is closed. The raised ribs are not required, and instead the pump chambers 181 may have no rib or other features, as shown for the right-side pump chamber 181 in FIG. 34. Similarly, the spikes 160 in the FIGS. 3, 4 and 6 embodiment include no skirt or similar feature at the base of the spike 160, whereas the embodiment in FIG. 33 includes a skirt 160a. This is also shown in FIG. 34. The skirt 160a may be arranged to receive the end of the spike cap 63 in a recess between the skirt 160a and the spike 160, helping to form a seal between the spike 160 and the spike cap 63.

Figure 35:
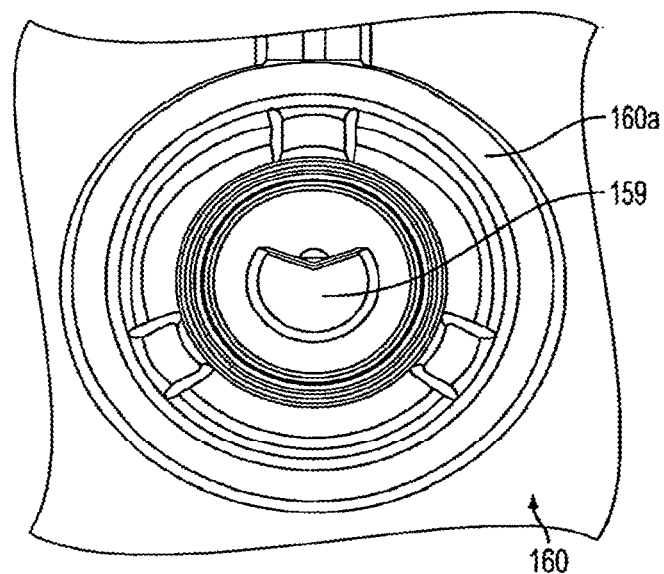
FIG. 35 shows an end view of a spike of a cassette in an illustrative embodiment.

Another inventive feature shown in FIG. 33 relates to the arrangement of the distal tip of the spike 163 and the lumen 159 through the spike 160. In this aspect, the distal tip of the spike 160 is positioned at or near the longitudinal axis of the spike 160, which runs generally along the geometric center of the spike 160. Positioning the distal tip of the spike 160 at or near the longitudinal axis may help ease alignment tolerances when engaging the spike 160 with a corresponding solution line 30 and help the spike 160 puncture a septum or membrane 30b in the connector end 30a of the line 30. As a result, the lumen 159 of the spike 160 is located generally off of the longitudinal axis of the spike 160, e.g., near a bottom of the spike 160 as shown in FIG. 33 and as shown in an end view of a spike 160 in FIG. 35. Also, the distal end of the spike 160 has a somewhat reduced diameter as compared to more proximal portions of the spike 160 (in this embodiment, the spike 160 actually has a step change in diameter at about ⅔ of the length of the spike 160 from the body 18). The reduced diameter of the spike 160 at the distal end may provide clearance between the spike 160 and the inner wall of the line 30, thus allowing the septum 30b a space to fold back to be positioned between the spike 160 and the line 30 when pierced by the spike 160. The stepped feature on the spike 160 may also be arranged to engage the line 30 at the location where the septum 30b is connected to the inner wall of the line 30, thus enhancing a seal formed between the line 30 and the spike 160.

Figure 36:
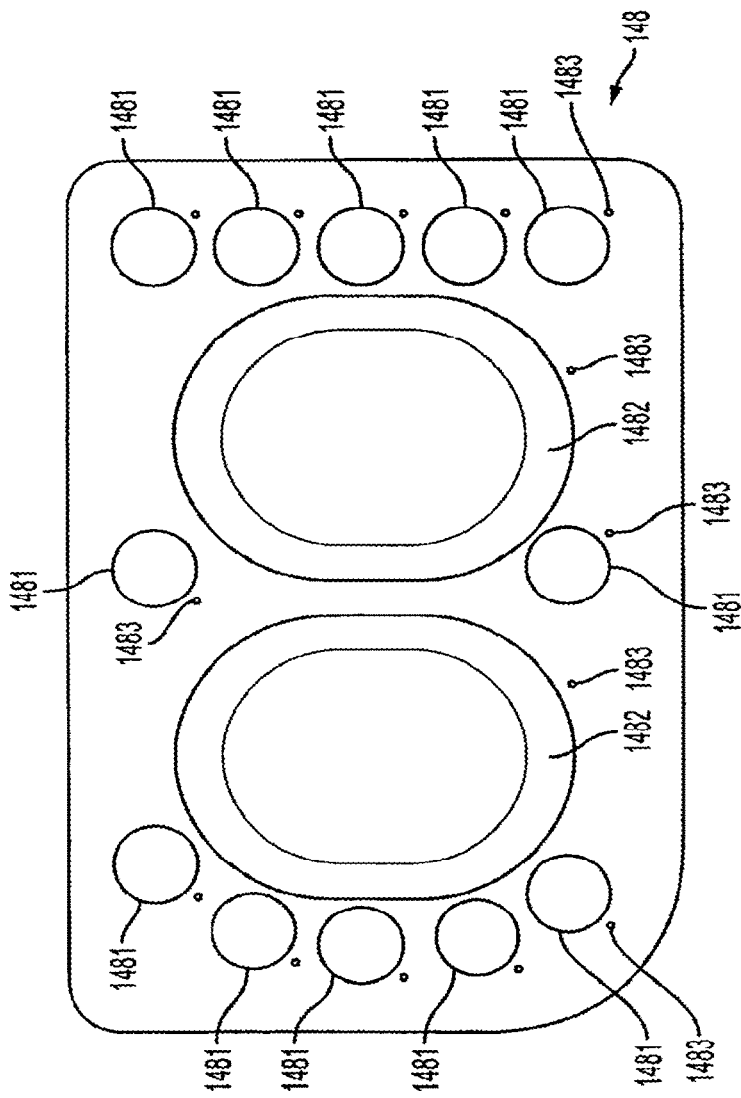
FIG. 36 shows a front view of a control surface of the cycler for interaction with a cassette in the FIG. 10 embodiment.

Once the cassette 24 and lines 30 are loaded into the cycler 14, the cycler 14 must control the operation of the cassette 24 to move fluid from the solution lines 30 to the heater bag 22 and to the patient. FIG. 36 shows a plan view of the control surface 148 of the cycler 14 that interacts with the pump chamber side of the cassette 24 (e.g., shown in FIG. 6) to cause fluid pumping and flowpath control in the cassette 24. When at rest, the control surface 148, which may be described as a type of gasket, and comprise a sheet of silicone rubber, may be generally flat. Valve control regions 1481 may (or may not) be defined in the control surface 148, e.g., by a scoring, groove, rib or other feature in or on the sheet surface, and be arranged to be movable in a direction generally transverse to the plane of the sheet. By moving inwardly/outwardly, the valve control regions 1481 can move associated portions of the membrane 15 on the cassette 24 so as to open and close respective valve ports 184, 186, 190 and 192 of the cassette 24, and thus control flow in the cassette 24. Two larger regions, pump control regions 1482, may likewise be movable so as to move associated shaped portions 151 of the membrane 15 that cooperate with the pump chambers 181. Like the shaped portions 151 of the membrane 15, the pump control regions 1482 may be shaped in a way to correspond to the shape of the pump chambers 181 when the control regions 1482 are extended into the pump chambers 181. In this way, the portion of the control sheet 148 at the pump control regions 1482 need not necessarily be stretched or otherwise resiliently deformed during pumping operation.

Each of the regions 1481 and 1482 may have an associated vacuum or evacuation port 1483 that may be used to remove all or substantially all of any air or other fluid that may be present between the membrane 15 of cassette 24, and the control surface 148 of cycler 14, e.g., after the cassette 24 is loaded into the cycler 14 and the door 141 closed. This may help ensure close contact of the membrane 15 with the control regions 1481 and 1482, and help control the delivery of desired volumes with pump operation and/or the open/closed state of the various valve ports. Note that the vacuum ports 1482 are formed in locations where the control surface 148 will not be pressed into contact with a wall or other relatively rigid feature of the cassette 24. For example, in accordance with one aspect of the invention, one or both of the pump chambers of the cassette may include a vacuum vent clearance region formed adjacent the pump chamber. In this illustrative embodiment as shown in FIGS. 3 and 6, the base member 18 may include vacuum vent port clearance or extension features 182 (e.g., recessed areas that are fluidly connected to the pump chambers) adjacent and outside the oval-shaped depressions forming the pump chambers 181 to allow the vacuum vent port 1483 for the pump control region 1482 to remove any air or fluid from between membrane 15 and control surface 148 (e.g., due to rupture of the membrane 15) without obstruction. The extension feature may also be located within the perimeter of pump chamber 181.

However, locating vent port feature 182 outside the perimeter of pump chamber 181 may preserve more of the pumping chamber volume for pumping liquids, e.g., allows for the full footprint of pump chamber 181 to be used for pumping dialysate. Preferably, extension feature 182 is located in a vertically lower position in relation to pump chamber 181, so that any liquid that leaks between membrane 15 and control surface 148 is drawn out through vacuum port 1483 at the earliest opportunity. Similarly, vacuum ports 1483 associated with valves 1481 are preferably located in a vertically inferior position with respect to valves 1481.

Figure 37:
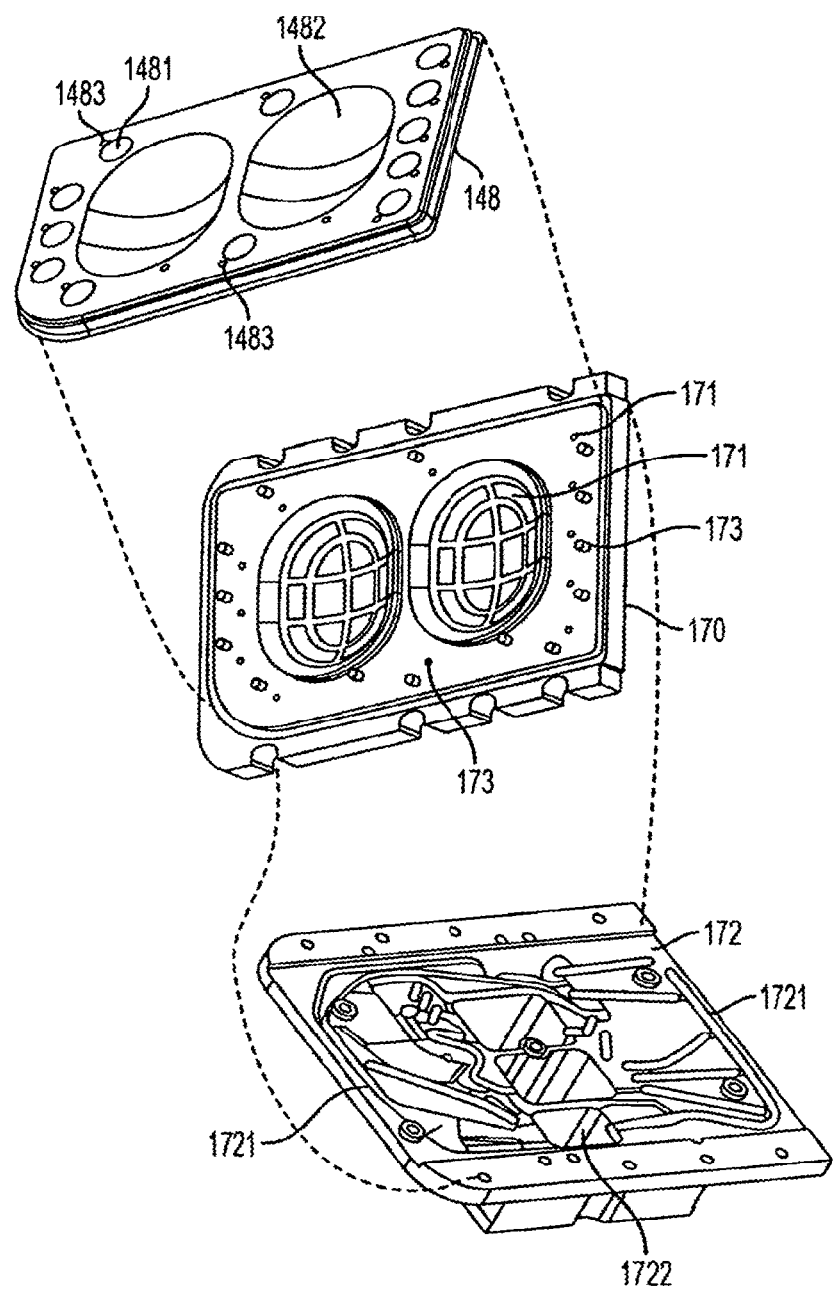
FIG. 37 shows an exploded view of an assembly for the interface of FIG. 36.

The control regions 1481 and 1482 may be moved by controlling a pneumatic pressure and/or volume on a side of the control surface 148 opposite the cassette 24, e.g., on a back side of the rubber sheet that forms the control surface 148. For example, as shown in FIG. 37, the control surface 148 may be backed by a mating block 170 that has control chambers 171 located in association with each control region 1481, 1482, and that are isolated from each other (or at least can be controlled independently of each other if desired). The surface of mating block 170 forms an interface with cassette 24 when cassette 24 is pressed into operative association with control surface 148 backed by mating block 170. The control chambers of mating block 170 are thus coupled to complementary valve or pumping chambers of cassette 24, sandwiching control regions 1481 and 1482 of control surface 148 adjacent to mating block 170, and the associated regions of membrane 15 (such as shaped portion 151) adjacent to cassette 24. Air or other control fluid may be moved into or out of the control chambers 171 of mating block 170 for the regions 1481, 1482, thereby moving the control regions 1481, 1482 as desired to open/close valve ports of the cassette 24 and/or effect pumping action at the pump chambers 181. In one illustrative embodiment shown in FIG. 37, the control chambers 171 may be arranged as cylindrically-shaped regions backing each of the valve control regions 1481 and a pair of elliptical voids backing the pump control regions 1482. Fluid control ports may be provided for each control chamber 171 so that the cycler 14 can control the volume of fluid and/or the pressure of fluid in each of the control chambers. For example, the mating block 170 may be mated with a manifold 172 that includes various ports, channels, openings, voids and/or other features that communicate with the control chambers 171 and allow suitable pneumatic pressure/vacuum to be applied to the control chambers 171. Although not shown, control of the pneumatic pressure/vacuum may be performed in any suitable way, such as through the use of controllable valves, pumps, pressure sensors, accumulators, and so on. Of course, it should be understood that the control regions 1481, 1482 may be moved in other ways, such as by gravity-based systems, hydraulic systems, and/or mechanical systems (such as by linear motors, etc.), or by a combination of systems including pneumatic, hydraulic, gravity-based and mechanical systems.

In accordance with an aspect of the invention, the vacuum ports 1483 may be used to detect leaks in the membrane 15, e.g., a liquid sensor in a conduit or chamber connected to a vacuum port 1483 may detect liquid if the membrane 15 is perforated or liquid otherwise is introduced between the membrane 15 and the control surface 148. For example, vacuum ports 1483 may align with and be sealingly associated with complementary vacuum ports 173 in mating block 170, which in turn may be sealingly associated with fluid passages 1721 leading to a common fluid collection chamber 1722 in manifold 172. The fluid collection chamber 1722 may contain an inlet through which vacuum can be applied and distributed to all vacuum ports 1483 of control surface 148. By applying vacuum to the fluid collection chamber 1722, fluid may be drawn from each of the vacuum ports 173 and 1483, thus removing fluid from any space between the membrane 15 and the control surface 148 at the various control regions. However, if there is liquid present at one or more of the regions, the associated vacuum port 1483 may draw the liquid into the vacuum ports 173 and into the lines 1721 leading to the fluid collection chamber 1722. Any such liquid may collect in the fluid collection chamber 1722, and be detected by one or more suitable sensors, e.g., a pair of conductivity sensors that detect a change in conductivity in the chamber 1722 indicating the presence of liquid. In this embodiment, the sensors may be located at a bottom side of the fluid collection chamber 1722, while a vacuum source connects to the chamber 1722 at an upper end of the chamber 1722. Therefore, if liquid is drawn into the fluid collection chamber 1722, the liquid may be detected before the liquid level reaches the vacuum source. Optionally, a hydrophobic filter, valve or other component may be place at the vacuum source connection point into the chamber 1722 to help further resist the entry of liquid into the vacuum source. In this way, a liquid leak may be detected and acted upon by controller 16 (e.g., generating an alert, closing liquid inlet valves and ceasing pumping operations) before the vacuum source valve is placed at risk of being contaminated by the liquid.

In one embodiment, the inner wall of the control chambers 171 can include raised elements somewhat analogous to the spacer elements 50 of the pump chamber, e.g., as shown in FIG. 37 for the control chambers 171 associated with the pump control regions 1482. These raised elements can take the form of plateau features, ribs, or other protrusions that keep the control ports recessed away from the fully retracted control regions 1482. This arrangement may allow for a more uniform distribution of pressure or vacuum in the control chamber 171, and prevent premature blocking of any control port by the control surface 148. A pre-formed control surface 148 (at least in the pump control regions) may not be under a significant stretching force when fully extended against either the inner wall of the pump chamber of the cassette 24 during a delivery stroke, or the inner wall of the control chamber 171 during a fill stroke. It may therefore be possible for the control region 1482 to extend asymmetrically into the control chamber 171, causing the control region 1482 to prematurely close off one or more ports of the control chamber before the chamber is fully evacuated. Having features on the inner surface of the control chamber 171 that prevent contact between the control region 1482 and the control ports may help to assure that the control region 1482 can make uniform contact with the control chamber inner wall during a fill stroke.

As suggested above, the cycler 14 may include a control system 16 with a data processor in electrical communication with the various valves, pressure sensors, motors, etc., of the system and is preferably configured to control such components according to a desired operating sequence or protocol. The control system 16 may include appropriate circuitry, programming, computer memory, electrical connections, and/or other components to perform a specified task. The system may include pumps, tanks, manifolds, valves or other components to generate desired air or other fluid pressure (whether positive pressure—above atmospheric pressure or some other reference—or negative pressure or vacuum—below atmospheric pressure or some other reference) to control operation of the regions of the control surface 148, and other pneumatically-operated components. Further details regarding the control system 16 (or at least portions of it) are provided below.

In one illustrative embodiment, the pressure in the pump control chambers 171 may be controlled by a binary valve, e.g., which opens to expose the control chamber 171 to a suitable pressure/vacuum and closes to cut off the pressure/vacuum source. The binary valve may be controlled using a saw tooth-shaped control signal which may be modulated to control pressure in the pump control chamber 171. For example, during a pump delivery stroke (i.e., in which positive pressure is introduced into the pump control chamber 171 to move the membrane 15/control surface 148 and force liquid out of the pump chamber 181), the binary valve may be driven by the saw tooth signal so as to open and close at a relatively rapid rate to establish a suitable pressure in the control chamber 171 (e.g., a pressure between about 70-90 mmHg). If the pressure in the control chamber 171 rises above about 90 mmHg, the saw tooth signal may be adjusted to close the binary valve for a more extended period. If the pressure drops below about 70 mmHg in the control chamber 171, the saw tooth control signal may again be applied to the binary valve to raise the pressure in the control chamber 171. Thus, during a typical pump operation, the binary valve will be opened and closed multiple times, and may be closed for one or more extended periods, so that the pressure at which the liquid is forced from the pump chamber 181 is maintained at a desired level or range (e.g., about 70-90 mmHg).

In some embodiments and in accordance with an aspect of the invention, it may be useful to detect an "end of stroke" of the membrane 15/pump control region 1482, e.g., when the membrane 15 contacts the spacers 50 in the pump chamber 181 or the pump control region 1482 contacts the wall of the pump control chamber 171. For example, during a pumping operation, detection of the "end of stroke" may indicate that the membrane 15/pump control region 1482 movement should be reversed to initiate a new pump cycle (to fill the pump chamber 181 or drive fluid from the pump chamber 181). In one illustrative embodiment in which the pressure in the control chamber 171 for a pump is controlled by a binary valve driven by a saw tooth control signal, the pressure in the pump chamber 181 will fluctuate at a relatively high frequency, e.g., a frequency at or near the frequency at which the binary valve is opened and closed. A pressure sensor in the control chamber 171 may detect this fluctuation, which generally has a higher amplitude when the membrane 15/pump control region 1482 are not in contact with the inner wall of the pump chamber 181 or the wall of the pump control chamber 171. However, once the membrane 15/pump control region 1482 contacts the inner wall of the pump chamber 181 or the wall of the pump control chamber 171 (i.e., the "end of stroke"), the pressure fluctuation is generally damped or otherwise changes in a way that is detectable by the pressure sensor in the pump control chamber 171. This change in pressure fluctuation can be used to identify the end of stroke, and the pump and other components of the cassette 24 and/or cycler 14 may be controlled accordingly.

Occluder

In one aspect of the invention, an occluder for opening/closing one or more flexible lines may include a pair of opposed occluding members, which may be configured as resilient elements, such as flat plates made of a spring steel (e.g., leaf springs), having a force actuator configured to apply a force to one or both of the occluding members to operate the occluder. In certain embodiments, the force actuator may comprise an expandable or enlargable member positioned between the resilient elements. With the expandable member in a reduced size condition, the resilient elements may be in a flat or nearly flat condition and urge a pinch head to engage with one or more lines so as to pinch the lines closed. However, when the expandable member urges the resilient elements apart, the resilient elements may bend and withdraw the pinch head, releasing the lines and allowing flow through the lines. In other embodiments, the occluding members could be essentially rigid with respect to the levels of force applied by the force actuator. In certain embodiments, the force actuator may apply a force to one or both opposed occluding members to increase the distance between the occluding members in at least a portion of the region where they are opposed to effect opening or closing of the flexible tubing.

Figure 38:
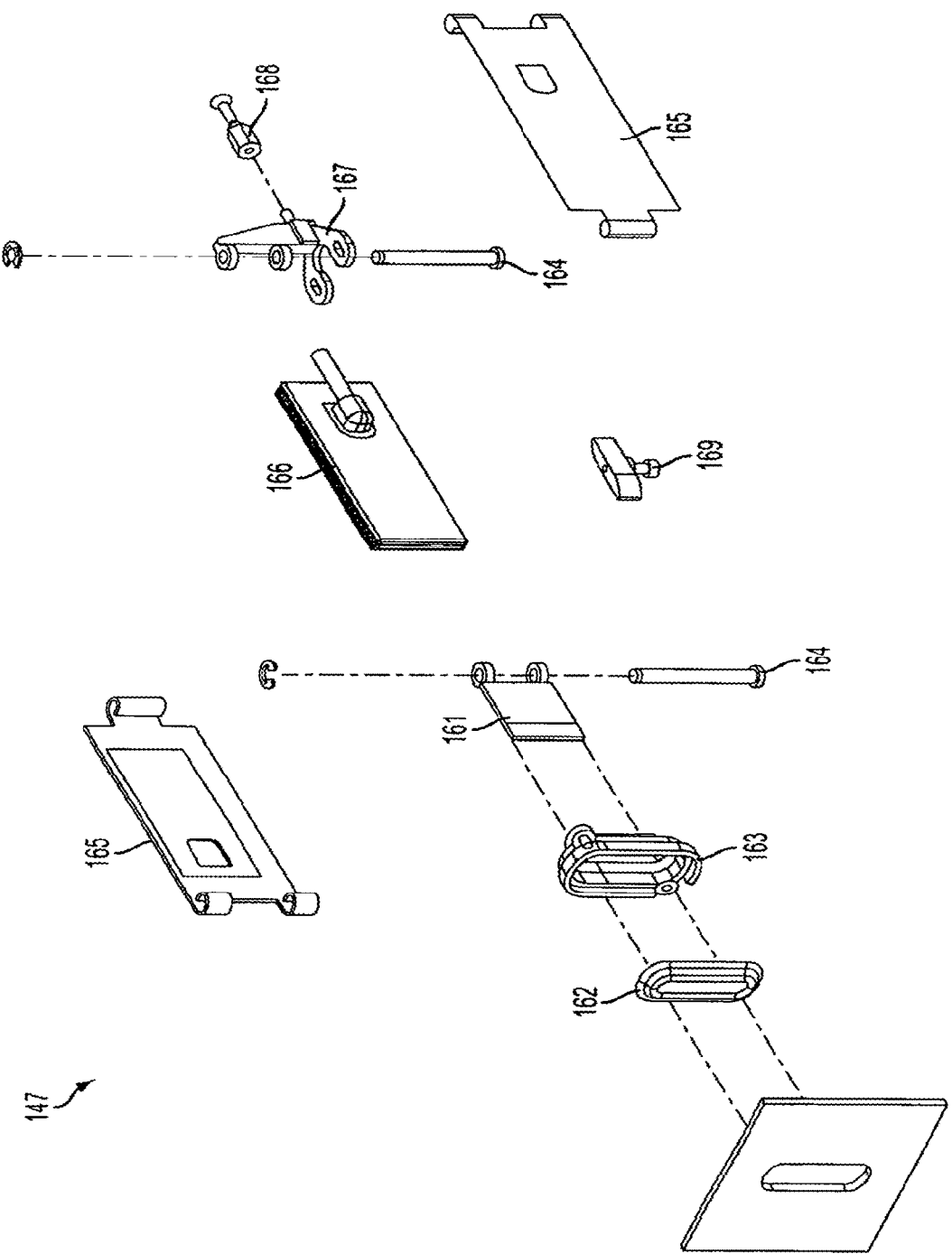
FIG. 38 shows an exploded perspective view of an occluder in an illustrative embodiment.
Figure 39:
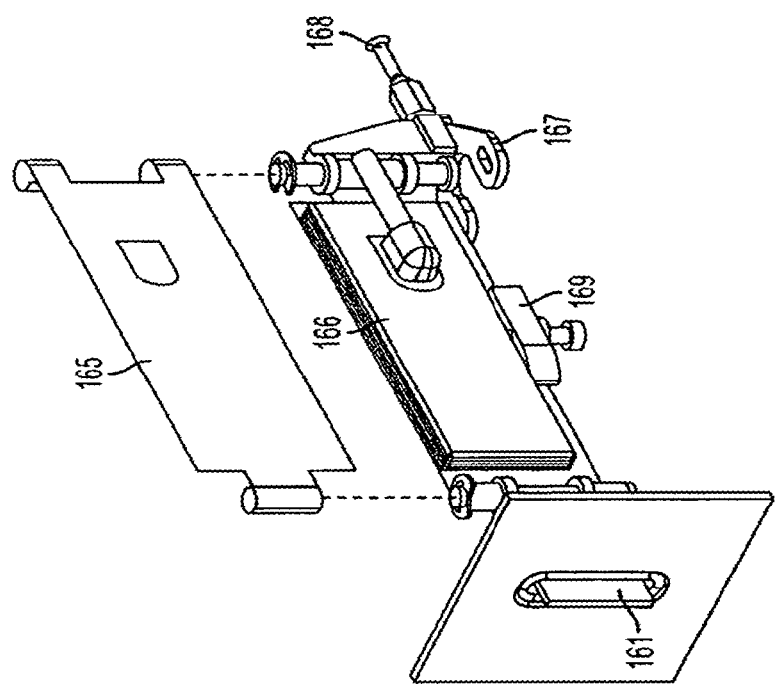
FIG. 39 shows a partially exploded perspective view of the occluder of FIG. 38.

FIG. 38 shows an exploded view and FIG. 39 shows a partially assembled view of an illustrative embodiment of an occluder 147 that may be used to close, or occlude, the patient and drain lines 34 and 28, and/or other lines in the cycler 14 or the set 12 (such as, for example, the heater bag line 26). The occluder 147 includes an optional pinch head 161, e.g., a generally flat blade-like element that contacts the tubes to press the tubes against the door 141 and pinch the tubes closed. In other embodiments, the function of the pinch head could be replaced by an extending edge of one or both of occluding members 165. The pinch head 161 includes a gasket 162, such as an O-ring or other member, that cooperates with the pinch head 161 to help resist entry of fluid (air or liquid for example) into the cycler 14 housing, e.g., in case of leakage in one of the occluded lines. The bellows gasket 162 is mounted to, and pinch head 161 passes through, a pinch head guide 163 that is mounted to the front panel of the cycler housing, i.e., the panel exposed by opening the door 141. The pinch head guide 163 allows the pinch head 161 to move in and out of the pinch head guide 163 without binding and/or substantial resistance to sliding motion of the pinch head 161. A pivot shaft 164 attaches a pair of opposed occluder members, comprising in the illustrated embodiment spring plates 165, that each include a hook-shaped pivot shaft bearing, e.g., like that found on standard door hinges, to the pinch head 161. That is, the openings of shaft guides on the pinch head 161, and the openings formed by the hook-shaped bearings on the spring plates 165 are aligned with each other and the pivot shaft 164 is inserted through the openings so the pinch head 161 and the spring plates 165 are pivotally connected together. The spring plates 165 may be made of any suitable material, such as steel, and may be arranged to be generally flat when unstressed. The opposite end of the spring plates 165 includes similar hook-shaped bearings, which are pivotally connected to a linear adjustor 167 by a second pivot shaft 164. In this embodiment, the force actuator comprises a bladder 166 is positioned between the spring plates 165 and arranged so that when fluid (e.g., air under pressure) is introduced into the bladder, the bladder may expand and push the spring plates 165 away from each other in a region between the pivot shafts 164. A linear adjustor 167 is fixed to the cycler housing 82 while the pinch head 161 is allowed to float, although its movement is guided by the pinch head guide 163. The linear adjustor 167 includes slot holes at its lower end, allowing the entire assembly to be adjusted in position and thus permitting the pinch head to be appropriately positioned when the occluder 147 is installed in the cycler 14. A turnbuckle 168 or other arrangement may be used to help adjust the position of the linear adjustor 167 relative to the housing 82. That is, the pinch head 161 generally needs to be properly positioned so that with the spring plates 165 located near each other and the bladder 166 substantially emptied or at ambient pressure, the pinch head 161 suitably presses on the patient and drain lines so as to pinch the tubes closed to flow without cutting, kinking or otherwise damaging the tubes. The slot openings in the linear adjustor 167 allows for this fine positioning and fixing of the occluder 147 in place. An override release device, such as provided by release blade 169 is optionally positioned between the spring plates 165, and as is discussed in more detail below, may be rotated so as to push the spring plates 165 apart, thereby withdrawing the pinch head 161 into the pinch head guide 163. The release blade 169 may be manually operated, e.g., to disable the occluder 147 in case of power loss, bladder 166 failure or other circumstance.

Additional configurations and descriptions of certain components that may be instructive in constructing certain embodiments of the occluder are provided in U.S. Pat. No. 6,302,653. The spring plates 165 may be constructed from any material that is elastically resistant to bending forces and which has sufficient longitudinal stiffness (resistance to bending) to provide sufficient restoring force, in response to a bending displacement, to occlude a desired number of collapsible tubes. In the illustrated embodiment, each spring plate is essentially flat when unstressed and in the shape of a sheet or plate. In alternative embodiments utilizing one or more resilient occluding members (spring members), any occluding member(s) that is elastically resistant to bending forces and which has sufficient longitudinal stiffness (resistance to bending) to provide sufficient restoring force, in response to a bending displacement to occlude a desired number of collapsible tubes may be utilized. Potentially suitable spring members can have a wide variety of shapes as apparent to those of ordinary skill in the art, including, but not limited to cylindrical, prism-shaped, trapezoidal, square, or rectangular bars or beams, I-beams, elliptical beams, bowl-shaped surfaces, and others. Those of ordinary skill in the art can readily select proper materials and dimensions for spring plates 165 based on the present teachings and the requirements of a particular application.

Figure 40:
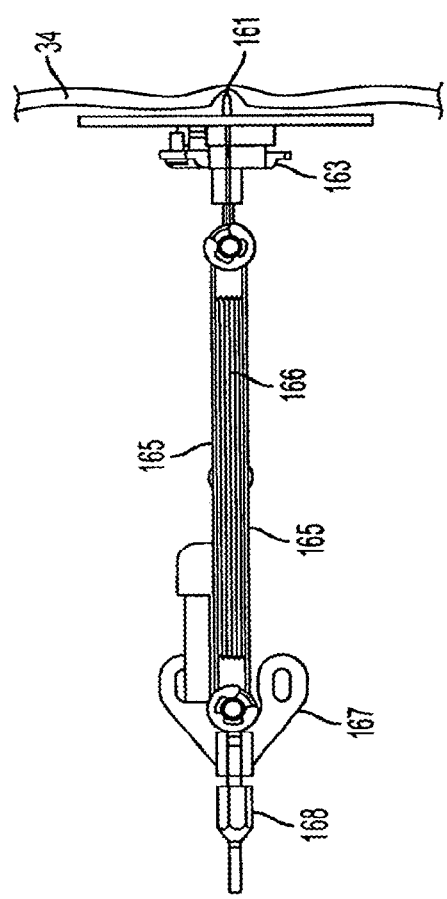
FIG. 40 shows a top view of the occluder of FIG. 38 with the bladder in a deflated state.
Figure 41:
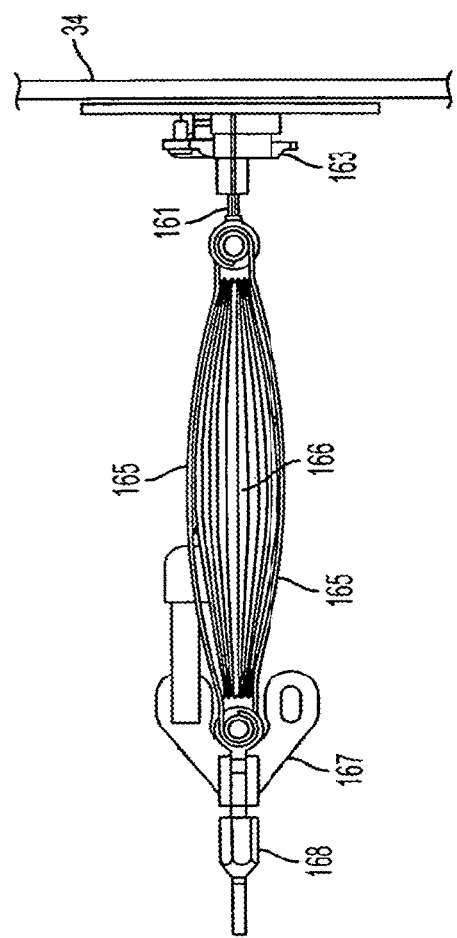
FIG. 41 shows a top view of the occluder of FIG. 38 with the bladder in an inflated state.

FIG. 40 shows a top view of the occluder 147 with the bladder 166 deflated and the spring plates 165 located near each other and in a flat or nearly flat condition. In this position, the pinch head 161 is fully extended from the pinch head guide and the front panel of the cycler 14 (i.e., the panel inside of the door 141) and enabled to occlude the patient and drain lines. FIG. 41, on the other hand, shows the bladder 166 in an inflated state in which the spring plates 165 are pushed apart, thereby retracting the pinch head 161 into the pinch head guide 163. (Note that the linear adjustor 167 is fixed in place relative to the cycler housing 82 and thus fixed relative to the front panel of the housing 82. As the spring plates 165 are moved apart, the pinch head 161 moves rearwardly relative to the front panel since the pinch head 161 is arranged to move freely in and out of the pinch head guide 163.) This condition prevents the pinch head 161 from occluding the patient and drain lines and is the condition in which the occluder 147 remains during normal operation of the cycler 14. That is, as discussed above, various components of the cycler 14 may operate using air pressure/vacuum, e.g., the control surface 148 may operate under the drive of suitable air pressure/vacuum to cause fluid pumping and valve operation for the cassette 24. Thus, when the cycler 14 is operating normally, the cycler 14 may produce sufficient air pressure to not only control system operation, but also to inflate the bladder 166 to retract the pinch head 161 and prevent occlusion of the patient and drain lines.

However, in the case of system shut down, failure, fault or other condition, air pressure to the bladder 166 may be terminated, causing the bladder 166 to deflate and the spring plates 165 to straighten and extend the pinch head 161 to occlude the lines. One possible advantage of the arrangement shown is that the return force of the spring plates 165 is balanced such that the pinch head 161 generally will not bind in the pinch head guide 163 when moving relative to the pinch head guide 163. In addition, the opposing forces of the spring plates 165 will tend to reduce the amount of asymmetrical frictional wear of the pivot shafts and bushings of the assembly. Also, once the spring plates 165 are in an approximately straight position, the spring plates 165 can exert a force in a direction generally along the length of the pinch head 161 that is several times larger than the force exerted by the bladder 166 on the spring plates 165 to separate the spring plates 165 from each other and retract the pinch head 161. Further, with the spring plates 165 in a flat or nearly flat condition, the force needed to be exerted by fluid in the collapsed tubing to overcome the pinching force exerted by the pinch head 161 approaches a relatively high force required, when applied to the spring plates at their ends and essentially parallel to the plane of the flattened spring plates, to buckle the spring plates by breaking the column stability of the flattened spring plates. As a result, the occluder 147 can be very effective in occluding the lines with a reduced chance of failure while also requiring a relatively small force be applied by the bladder 166 to retract the pinch head 161. The dual spring plate arrangement of the illustrative embodiment may have the additional advantage of significantly increasing the pinching force provided by the pinch head, for any given force needed to bend the spring plate, and/or for any given size and thickness of spring plate.

In some circumstances, the force of the occluder 147 on the lines may be relatively large and may cause the door 141 to be difficult to open. That is, the door 141 must oppose the force of the occluder 147 when the pinch head 161 is in contact with and occluding lines, and in some cases this may cause the latch that maintains the door 141 in a closed state to be difficult or impossible to operate by hand. Of course, if the cycler 14 is started and produces air pressure to operate, the occluder bladder 166 can be inflated and the occluder pinch head 161 retracted. However, in some cases, such as with a pump failure in the cycler 14, inflation of the bladder 166 may be impossible or difficult. To allow opening of the door, the occluder 147 may include a manual release. In this illustrative embodiment, the occluder 147 may include a release blade 169 as shown in FIGS. 38 and 39 which includes a pair of wings pivotally mounted for rotary movement between the spring plates 165. When at rest, the release blade wings may be aligned with the springs as shown in FIG. 39, allowing the occluder to operate normally. However, if the spring plates 165 are in a flat condition and the pinch head 161 needs to be retracted manually, the release blade 169 may be rotated, e.g., by engaging a hex key or other tool with the release blade 169 and turning the release blade 169, so that the wings push the spring plates 165 apart. The hex key or other tool may be inserted through an opening in the housing 82 of the cycler 14, e.g., an opening near the left side handle depression in the cycler housing 82, and operated to disengage the occluder 147 and allow the door 141 to be opened.

Pump Volume Delivery Measurement

In another aspect of the invention, the cycler 14 may determine a volume of fluid delivered in various lines of the system 10 without the use of a flowmeter, weight scale or other direct measurement of fluid volume or weight. For example, in one embodiment, a volume of fluid moved by a pump, such as a pump in the cassette 24, may be determined based on pressure measurements of a gas used to drive the pump. In one embodiment, a volume determination can be made by isolating two chambers from each other, measuring the respective pressures in the isolated chambers, allowing the pressures in the chambers to partially or substantially equalize (by fluidly connecting the two chambers) and measuring the pressures. Using the measured pressures, the known volume of one of the chambers, and an assumption that the equalization occurs in an adiabatic way, the volume of the other chamber (e.g., a pump chamber) can be calculated. In one embodiment, the pressures measured after the chambers are fluidly connected may be substantially unequal to each other, i.e., the pressures in the chambers may not have yet completely equalized. However, these substantially unequal pressures may be used to determine a volume of the pump control chamber, as explained below.

Figure 42:
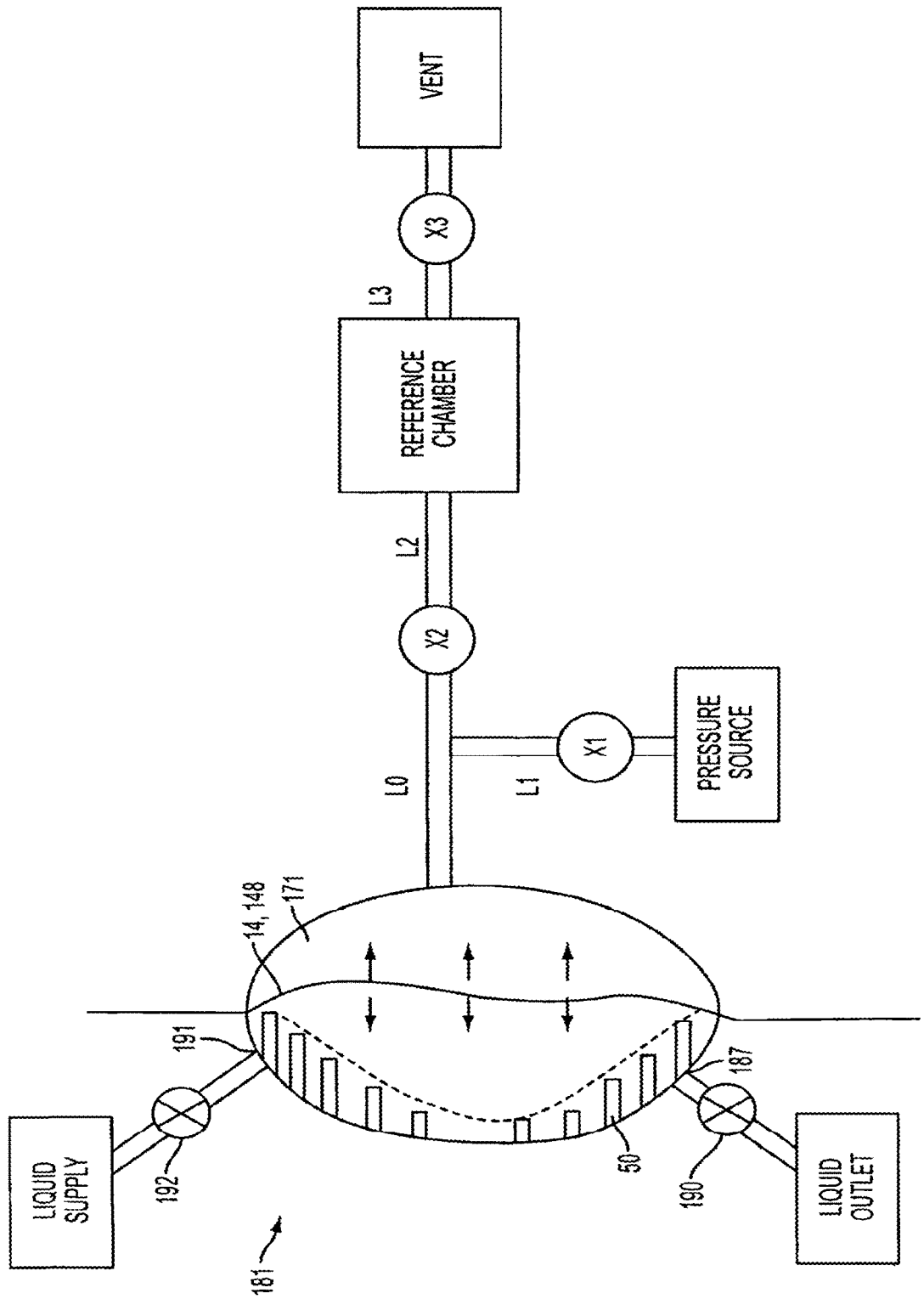
FIG. 42 is a schematic view of a pump chamber of a cassette and associated control components and inflow/outflow paths in an illustrative embodiment.

For example, FIG. 42 shows a schematic view of a pump chamber 181 of the cassette 24 and associated control components and inflow/outflow paths. In this illustrative example, a liquid supply, which may include the heater bag 22, heater bag line 26 and a flow path through the cassette 24, is shown providing a liquid input at the upper opening 191 of the pump chamber. The liquid outlet is shown in this example as receiving liquid from the lower opening 187 of the pump chamber 181, and may include a flow path of the cassette 24 and the patient line 34, for example. The liquid supply may include a valve, e.g., including the valve port 192, that can be opened and closed to permit/impede flow to or from the pump chamber 181. Similarly, the liquid outlet may include a valve, e.g., including the valve port 190, that can be opened and closed to permit/impede flow to or from the pump chamber 181. Of course, the liquid supply could include any suitable arrangement, such as one or more solution containers, the patient line, one or more flow paths in the cassette 24 or other liquid source, and the liquid outlet could likewise include any suitable arrangement, such as the drain line, the heater bag and heater bag line, one or more flow paths in the cassette 24 or other liquid outlet. Generally speaking, the pump chamber 181 (i.e., on the left side of the membrane 14 in FIG. 42) will be filled with an incompressible liquid, such as water or dialysate, during operation. However, air or other gas may be present in the pump chamber 181 in some circumstances, such as during initial operation, priming, or other situations as discussed below. Also, it should be understood that although aspects of the invention relating to volume and/or pressure detection for a pump are described with reference to the pump arrangement of the cassette 24, aspects of the invention may be used with any suitable pump or fluid movement system.

FIG. 42 also shows schematically to the right of the membrane 15 and the control surface 148 (which are adjacent each other) a control chamber 171, which may be formed as a void or other space in the mating block 170 associated with the pump control region 1482 of the control surface 148 for the pump chamber 181, as discussed above. It is in the control chamber 171 that suitable air pressure is introduced to cause the membrane 15/control region 1482 to move and effect pumping of liquid in the pump chamber 181. The control chamber 171 may communicate with a line L0 that branches to another line L1 and a first valve X1 that communicates with a pressure source (e.g., a source of air pressure or vacuum). The pressure source may include a piston pump in which the piston is moved in a chamber to control a pressure delivered to the control chamber 171, or may include a different type of pressure pump and/or tank(s) to deliver suitable gas pressure to move the membrane 15/control region 1482 and perform pumping action. The line L0 also leads to a second valve X2 that communicates with another line L2 and a reference chamber (e.g., a space suitably configured for performing the measurements described below). The reference chamber also communicates with a line L3 having a valve X3 that leads to a vent or other reference pressure (e.g., a source of atmospheric pressure or other reference pressure). Each of the valves X1, X2 and X3 may be independently controlled. Pressure sensors may be arranged, e.g., one sensor at the control chamber 171 and another sensor at the reference chamber, to measure pressure associated with the control chamber and the reference chamber. These pressure sensors may be positioned and may operate to detect pressure in any suitable way. The pressure sensors may communicate with the control system 16 for the cycler 14 or other suitable processor for determining a volume delivered by the pump or other features.

As mentioned above, the valves and other components of the pump system shown in FIG. 42 can be controlled so as to measure pressures in the pump chamber 181, the liquid supply and/or liquid outlet, and/or to measure a volume of fluid delivered from the pump chamber 181 to the liquid supply or liquid outlet. Regarding volume measurement, one technique used to determine a volume of fluid delivered from the pump chamber 181 is to compare the relative pressures at the control chamber 171 to that of the reference chamber in two different pump states. By comparing the relative pressures, a change in volume at the control chamber 171 can be determined, which corresponds to a change in volume in the pump chamber 181 and reflects a volume delivered from/received into the pump chamber 181. For example, after the pressure is reduced in the control chamber 171 during a pump chamber fill cycle (e.g., by applying negative pressure from the pressure source through open valve X1) so as to draw the membrane 15 and pump control region 1482 into contact with at least a portion of the control chamber wall (or to another suitable position for the membrane 15/region 1482), valve X1 may be closed to isolate the control chamber from the pressure source, and valve X2 may be closed, thereby isolating the reference chamber from the control chamber 171. Valve X3 may be opened to vent the reference chamber to ambient pressure, then closed to isolate the reference chamber. With valve X1 closed and the pressures in the control chamber and reference chamber measured, valve X2 is then opened to allow the pressure in the control chamber and the reference chamber to start to equalize. The initial pressures of the reference chamber and the control chamber, together with the known volume of the reference chamber and pressures measured after equalization has been initiated (but not yet necessarily completed) can be used to determine a volume for the control chamber. This process may be repeated at the end of the pump delivery cycle when the sheet 15/control region 1482 are pushed into contact with the spacer elements 50 of the pump chamber 181. By comparing the control chamber volume at the end of the fill cycle to the volume at the end of the delivery cycle, a volume of liquid delivered from the pump can be determined.

Conceptually, the pressure equalization process (e.g., at opening of the valve X2) is viewed as happening in an adiabatic way, i.e., without heat transfer occurring between air in the control and reference chambers and its environment. The conceptual notion is that there is an imaginary piston located initially at the valve X2 when the valve X2 is closed, and that the imaginary piston moves in the line L0 or L2 when the valve X2 is opened to equalize the pressure in the control and reference chambers. Since (a) the pressure equalization process happens relatively quickly, (b) the air in the control chamber and the reference chamber has approximately the same concentrations of elements, and (c) the temperatures are similar, the assumption that the pressure equalization happens in an adiabatic way may introduce only small error into the volume measurements. Also, in one embodiment, the pressures taken after equalization has been initiated may be measured before substantial equalization has occurred—further reducing the time between measuring the initial pressures and the final pressures used to determine the pump chamber volume. Error can be further reduced, for example, by using low thermal conductivity materials for the membrane 15/control surface 148, the cassette 24, the control chamber 171, the lines, the reference chamber, etc., so as to reduce heat transfer.

Given the assumption that an adiabatic system exists between the state when the valve X2 is closed until after the valve X2 is opened and the pressures equalize, the following applies:

$$PV^\gamma = \text{Constant} \tag{1}$$

where P is pressure, V is volume and $\gamma$ is equal to a constant (e.g., about 1.4 where the gas is diatomic, such as air). Thus, the following equation can be written to relate the pressures and volumes in the control chamber and the reference chamber before and after the opening of valve X2 and pressure equalization occurs:

$$PrVr^\gamma + PdVd^\gamma = \text{Constant} = PfVf^\gamma \tag{2}$$

where Pr is the pressure in the reference chamber and lines L2 and L3 prior to the valve X2 opening, Vr is the volume of the reference chamber and lines L2 and L3 prior to the valve X2 opening, Pd is the pressure in the control chamber and the lines L0 and L1 prior to the valve X2 opening, Vd is the volume of the control chamber and the lines L0 and L1 prior to the valve X2 opening, Pf is the equalized pressure in the reference chamber and the control chamber after opening of the valve X2, and Vf is the volume of the entire system including the control chamber, the reference chamber and the lines L0, L1, L2, and L3, i.e., Vf=Vd+Vr. Since Pr, Vr, Pd, Pf and $\gamma$ are known, and Vf=Vr+Vd, this equation can be used to solve for Vd. (Although reference is made herein, including in the claims, to use of a "measured pressure" in determining volume values, etc., it should be understood that such a measured pressure value need not necessarily be any particular form, such as in psi units. Instead, a "measured pressure" or "determined pressure" may include any value that is representative of a pressure, such as a voltage level, a resistance value, a multibit digital number, etc. For example, a pressure transducer used to measure pressure in the pump control chamber may output an analog voltage level, resistance or other indication that is representative of the pressure in the pump control chamber. The raw output from the transducer may be used as a measured pressure, and/or some modified form of the output, such as a digital number generated using an analog output from the transducer, a psi or other value that is generated based on the transducer output, and so on. The same is true of other values, such as a determined volume, which need not necessarily be in a particular form such as cubic centimeters. Instead, a determined volume may include any value that is representative of the volume, e.g., could be used to generate an actual volume in, say, cubic centimeters.)

In an embodiment of a fluid management system ("FMS") technique to determine a volume delivered by the pump, it is assumed that pressure equalization upon opening of the valve X2 occurs in an adiabatic system. Thus, Equation 3 below gives the relationship of the volume of the reference chamber system before and after pressure equalization:

$$Vrf = Vri(Pf/Patm)^{-(1/\gamma)} \tag{3}$$

where Vrf is the final (post-equalization) volume of the reference chamber system including the volume of the reference chamber, the volume of the lines L2 and L3 and the volume adjustment resulting from movement of the "piston", which may move to the left or right of the valve X2 after opening, Vri is the initial (pre-equalization) volume of the reference chamber and the lines L2 and L3 with the "piston" located at the valve X2, Pf is the final equalized pressure after the valve X2 is opened, and Patm is the initial pressure of the reference chamber before valve X2 opening (in this example, atmospheric pressure). Similarly, Equation 4 gives the relationship of the volume of the control chamber system before and after pressure equalization:

$$Vdf = Vdi(Pf/Pdi)^{-(1/\gamma)} \tag{4}$$

where Vdf is the final volume of the control chamber system including the volume of the control chamber, the volume of the lines L0 and L1, and the volume adjustment resulting from movement of the "piston", which may move to the left or right of the valve X2 after opening, Vdi is the initial volume of the control chamber and the lines L0 and L1 with the "piston" located at the valve X2, Pf is the final pressure after the valve X2 is opened, and Pdi is the initial pressure of the control chamber before valve X2 opening.

The volumes of the reference chamber system and the control chamber system will change by the same absolute amount after the valve X2 is opened and the pressure equalizes, but will differ in sign (e.g., because the change in volume is caused by movement of the "piston" left or right when the valve X2 opens), as shown in Equation 5:

$$\Delta Vr = (-1)\Delta Vd \tag{5}$$

(Note that this change in volume for the reference chamber and the control chamber is due only to movement of the imaginary piston. The reference chamber and control chamber will not actually change in volume during the equalization process under normal conditions.) Also, using the relationship from Equation 3, the change in volume of the reference chamber system is given by:

$$\Delta Vr = Vrf - Vri = Vri(-1 + (Pf/Patm)^{-(1/\gamma)}) \tag{6}$$

Similarly, using Equation 4, the change in volume of the control chamber system is given by:

$$\Delta Vd = Vdf - Vdi = Vdi(-1 + (Pf/Pdi)^{-(1/\gamma)}) \tag{7}$$

Because Vri is known, and Pf and Patm are measured or known, $\Delta Vr$ can be calculated, which according to Equation 5 is assumed to be equal to $(-)\Delta Vd$. Therefore, Vdi (the volume of the control chamber system before pressure equalization with the reference chamber) can be calculated using Equation 7. In this embodiment, Vdi represents the volume of the control chamber plus lines L0 and L1, of which L0 and L1 are fixed and known quantities. Subtracting L0 and L1 from Vdi yields the volume of the control chamber alone. By using Equation 7 above, for example, both before (Vdi1) and after (Vdi2) a pump operation (e.g., at the end of a fill cycle and at the end of a discharge cycle), the change in volume of the control chamber can be determined, thus providing a measurement of the volume of fluid delivered by (or taken in by) the pump. For example, if Vdi1 is the volume of the control chamber at the end of a fill stroke, and Vdi2 is the volume of the control chamber at the end of the subsequent delivery stroke, the volume of fluid delivered by the pump may be estimated by subtracting Vdi1 from Vdi2. Since this measurement is made based on pressure, the volume determination can be made for nearly any position of the membrane 15/pump control region 1482 in the pump chamber 181, whether for a full or partial pump stroke. However, measurement made at the ends of fill and delivery strokes can be accomplished with little or no impact on pump operation and/or flow rate.

One aspect of the invention involves a technique for identifying pressure measurement values that are to be used in determining a volume for the control chamber and/or other purposes. For example, although pressure sensors may be used to detect a pressure in the control chamber and a pressure in the reference chamber, the sensed pressure values may vary with opening/closing of valves, introduction of pressure to the control chamber, venting of the reference chamber to atmospheric pressure or other reference pressure, etc. Also, since in one embodiment, an adiabatic system is assumed to exist from a time before pressure equalization between the control chamber and the reference chamber until after equalization, identifying appropriate pressure values that were measured as close together in time may help to reduce error (e.g., because a shorter time elapsed between pressure measurements may reduce the amount of heat that is exchanged in the system). Thus, the measured pressure values may need to be chosen carefully to help ensure appropriate pressures are used for determining a volume delivered by the pump, etc.

Figure 43:
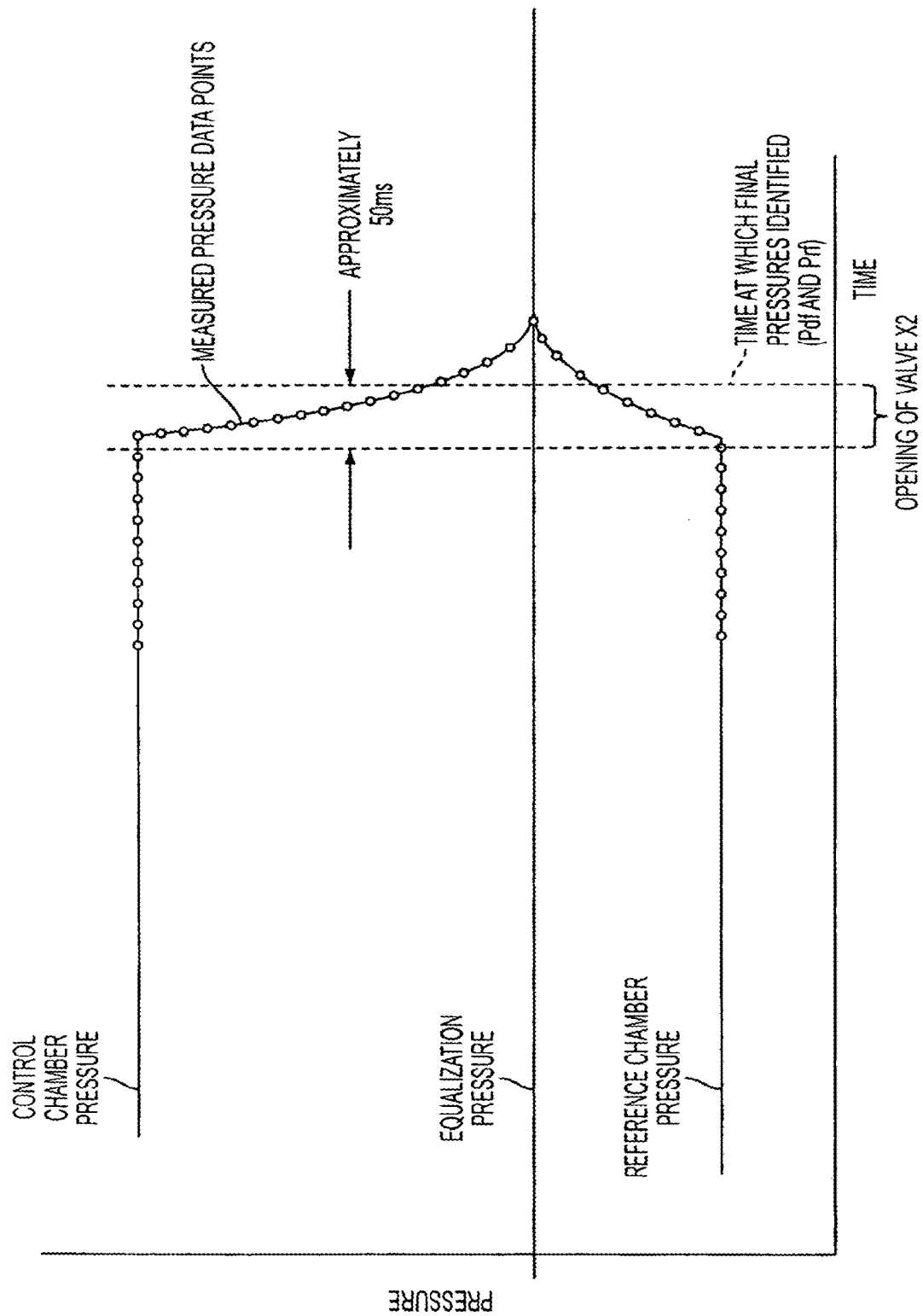
FIG. 43 is a plot of illustrative pressure values for the control chamber and the reference chamber from a point in time before opening of the valve X2 until some time after the valve X2 is opened for the embodiment of FIG. 42.

For purposes of explanation, FIG. 43 shows a plot of illustrative pressure values for the control chamber and the reference chamber from a point in time before opening of the valve X2 until some time after the valve X2 is opened to allow the pressure in the chambers to equalize. In this illustrative embodiment, the pressure in the control chamber is higher than the pressure in the reference chamber before equalization, but it should be understood that the control chamber pressure may be lower than the reference chamber pressure before equalization in some arrangements, such as during and/or at the end of a fill stroke. Also, the plot in FIG. 43 shows a horizontal line marking the equalization pressure, but it should be understood that this line is shown for clarity only. The equalization pressure in general will not be known prior to opening of the valve X2. In this embodiment, the pressure sensors sense pressure at a rate of about 2000 Hz for both the control chamber and the reference chamber, although other suitable sampling rates could be used. Before opening of the valve X2, the pressures in the control chamber and the reference chamber are approximately constant, there being no air or other fluid being introduced into the chambers. Thus, the valves X1 and X3 will generally be closed at a time before opening of the valve X2. Also, valves leading into the pump chamber, such as the valve ports 190 and 192, may be closed to prevent influence of pressure variations in the pump chamber, the liquid supply or liquid outlet.

At first, the measured pressure data is processed to identify the initial pressures for the control chamber and reference chambers, i.e., Pd and Pr. In one illustrative embodiment, the initial pressures are identified based on analysis of a 10-point sliding window used on the measured pressure data. This analysis involves generating a best fit line for the data in each window (or set), e.g., using a least squares technique, and determining a slope for the best fit line. For example, each time a new pressure is measured for the control chamber or the reference chamber, a least squares fit line may be determined for a data set including the latest measurement and the 9 prior pressure measurements. This process may be repeated for several sets of pressure data, and a determination may be made as to when the slope of the least squares fit lines first becomes negative (or otherwise non-zero) and continues to grow more negative for subsequent data sets (or otherwise deviates from a zero slope). The point at which the least squares fit lines begin to have a suitable, and increasing, non-zero slope may be used to identify the initial pressure of the chambers, i.e., at a time before the valve X2 is opened.

In one embodiment, the initial pressure value for the reference chamber and the control chamber may be determined to be in the last of 5 consecutive data sets, where the slope of the best fit line for the data sets increases from the first data set to the fifth data set, and the slope of the best fit line for the first data set first becomes non-zero (i.e., the slope of best fit lines for data sets preceding the first data set is zero or otherwise not sufficiently non-zero). For example, the pressure sensor may take samples every ½ millisecond (or other sampling rate) starting at a time before the valve X2 opens. Every time a pressure measurement is made, the cycler 14 may take the most recent measurement together with the prior 9 measurements, and generate a best fit line to the 10 data points in the set. Upon taking the next pressure measurement (e.g., ½ millisecond later), the cycler 14 may take the measurement together with the 9 prior measurements, and again generate a best fit line to the 10 points in the set. This process may be repeated, and the cycler 14 may determine when the slope of the best fit line for a set of 10 data points first turns non-zero (or otherwise suitably sloped) and, for example, that the slope of the best fit line for 5 subsequent sets of 10 data points increases with each later data set. To identify the specific pressure measurement to use, one technique is to select the third measurement in the $5^{th}$ data set (i.e., the $5^{th}$ data set with which it was found that the best fit line has been consistently increasing in slope and the $1^{st}$ measurement is the pressure measurement that was taken earliest in time) as the measurement to be used as the initial pressure for the control chamber or the reference chamber, i.e., Pd or Pr. This selection was chosen using empirical methods, e.g., plotting the pressure measurement values and then selecting which point best represents the time when the pressure began the equalization process. Of course, other techniques could be used to select the appropriate initial pressure.

In one illustrative embodiment, a check may be made that the times at which the selected Pd and Pr measurements occurred were within a desired time threshold, e.g., within 1-2 milliseconds of each other. For example, if the technique described above is used to analyze the control chamber pressure and the reference chamber pressure and identify a pressure measurement (and thus a point in time) just before pressure equalization began, the times at which the pressures were measured should be relatively close to each other. Otherwise, there may have been an error or other fault condition that invalidates one or both of the pressure measurements. By confirming that the time at which Pd and Pr occurred are suitably close together, the cycler 14 may confirm that the initial pressures were properly identified.

To identify when the pressures in the control chamber and the reference chamber have equalized such that measured pressures for the chamber can be used to reliably determine pump chamber volume, the cycler 14 may analyze data sets including a series of data points from pressure measurements for both the control chamber and the reference chamber, determine a best fit line for each of the data sets (e.g., using a least squares method), and identify when the slopes of the best fit lines for a data set for the control chamber and a data set for the reference chamber are first suitably similar to each other, e.g., the slopes are both close to zero or have values that are within a threshold of each other. When the slopes of the best fit lines are similar or close to zero, the pressure may be determined to be equalized. The first pressure measurement value for either data set may be used as the final equalized pressure, i.e., Pf. In one illustrative embodiment, it was found that pressure equalization occurred generally within about 200-400 milliseconds after valve X2 is opened, with the bulk of equalization occurring within about 50 milliseconds. Accordingly, the pressure in the control and reference chambers may be sampled approximately 400-800 times or more during the entire equalization process from a time before the valve X2 is opened until a time when equalization has been achieved.

In some cases, it may be desirable to increase the accuracy of the control chamber volume measurement using an alternate FMS technique. Substantial differences in temperature between the liquid being pumped, the control chamber gas, and the reference chamber gas may introduce significant errors in calculations based on the assumption that pressure equalization occurs adiabatically. Waiting to make pressure measurements until full equalization of pressure between the control chamber and the reference chamber may allow an excessive amount of heat transfer to occur. In one aspect of the invention, pressure values for the pump chamber and reference chamber that are substantially unequal to each other, i.e., that are measured before complete equalization has occurred, may be used to determine pump chamber volume.

In one embodiment, heat transfer may be minimized, and adiabatic calculation error reduced, by measuring the chamber pressures throughout the equalization period from the opening of valve X2 through full pressure equalization, and selecting a sampling point during the equalization period for the adiabatic calculations. In one embodiment of an APD system, measured chamber pressures that are taken prior to complete pressure equalization between the control chamber and the reference chamber can be used to determine pump chamber volume. In one embodiment, these pressure values may be measured about 50 ms after the chambers are first fluidly connected and equalization is initiated. As mentioned above, in one embodiment, complete equalization may occur about 200-400 ms after the valve X2 is opened. Thus, the measured pressures may be taken at a point in time after the valve X2 is opened (or equalization is initiated) that is about 10% to 50% or less of the total equalization time period. Said another way, the measured pressures may be taken at a point in time at which 50-70% of pressure equalization has occurred (i.e., the reference and pump chamber pressures have changed by about 50-70% of the difference between the initial chamber pressure and the final equalized pressure. Using a computer-enabled controller, a substantial number of pressure measurements in the control and reference chambers can be made, stored and analyzed during the equalization period (for example, 40-100 individual pressure measurements). Among the time points sampled during the first 50 ms of the equalization period, there is a theoretically optimized sampling point for conducting the adiabatic calculations (e.g., see FIG. 43 in which the optimized sampling point occurs at about 50 ms after opening of the valve X2). The optimized sampling point may occur at a time early enough after valve X2 opening to minimize thermal transfer between the gas volumes of the two chambers, but not so early as to introduce significant errors in pressure measurements due to the properties of the pressure sensors and delays in valve actuation. However, as can be seen in FIG. 43, the pressures for the pump chamber and reference chambers may be substantially unequal to each other at this point, and thus equalization may not be complete. (Note that in some cases, it may be technically difficult to take reliable pressure measurements immediately after the opening of valve X2, for example, because of the inherent inaccuracies of the pressure sensors, the time required for valve X2 to fully open, and the rapid initial change in the pressure of either the control chamber or the reference chamber immediately after the opening of valve X2.)

During pressure equalization, when the final pressure for the control chamber and reference chambers are not the same, Equation 2 becomes:

$$PriVri^{\gamma}+PdiVdi^{\gamma}=\text{Constant}=PrfVrf^{\gamma}+PdfVdf^{\gamma} \quad (8)$$

where: Pri=pressure in the reference chamber prior to opening valve X2, Pdi=pressure in the control chamber prior to opening valve X2, Prf=final reference chamber pressure, Pdf=final control chamber pressure.

An optimization algorithm can be used to select a point in time during the pressure equalization period at which the difference between the absolute values of $\Delta Vd$ and $\Delta Vr$ is minimized (or below a desired threshold) over the equalization period. (In an adiabatic process, this difference should ideally be zero, as indicated by Equation 5. In FIG. 43 the point in time at which the difference between the absolute values of $\Delta Vd$ and $\Delta Vr$ is minimized occurs at the 50 ms line, marked "time at which final pressures identified.") First, pressure data can be collected from the control and reference chambers at multiple points j=1 through n between the opening of valve X2 and final pressure equalization. Since Vri, the fixed volume of the reference chamber system before pressure equalization, is known, a subsequent value for Vrj (reference chamber system volume at sampling point j after valve X2 has opened) can be calculated using Equation 3 at each sampling point Prj along the equalization curve. For each such value of Vrj, a value for $\Delta Vd$ can be calculated using Equations 5 and 7, each value of Vrj thus yielding Vdij, a putative value for Vdi, the volume of the control chamber system prior to pressure equalization. Using each value of Vrj and its corresponding value of Vdij, and using Equations 3 and 4, the difference in the absolute values of $\Delta Vd$ and $\Delta Vr$ can be calculated at each pressure measurement point along the equalization curve. The sum of these differences squared provides a measure of the error in the calculated value of Vdi during pressure equalization for each value of Vrj and its corresponding Vdij. Denoting the reference chamber pressure that yields the least sum of the squared differences of $|\Delta Vd|$ and $|\Delta Vr|$ as Prf, and its associated reference chamber volume as Vrf, the data points Prf and Pdf corresponding to Vrf can then be used to calculate an optimized estimate of Vdi, the initial volume of the control chamber system.

One method for determining where on the equalization curve to capture an optimized value for Pdf and Prf is as follows:

1) Acquire a series of pressure data sets from the control and reference chambers starting just before the opening of valve X2 and ending with Pr and Pd becoming close to equal. If Pri is the first reference chamber pressure captured, then the subsequent sampling points in FIG. 32 will be referred to as Prj=Pr1, Pr2, ... Prn.

2) Using Equation 6, for each Prj after Pri, calculate the corresponding $\Delta Vrj$ where j represents the jth pressure data point after Pri.

$$\Delta Vrj = Vrj - Vri = Vri(-1 + (Prj/Pri)^{-(1/\gamma)})$$

3) For each such $\Delta Vrj$ calculate the corresponding Vdij using Equation 7. For example:

$$\Delta Vr1 = Vri*(-1 + (Pr1/Pri)^{-(1/\gamma)})$$

$$\Delta Vd1 = -\Delta Vr1$$

Therefore, $$Vdi1 = \Delta Vd1 / (-1 + (Pd1/Pdi)^{-(1/\gamma)})$$
$$\vdots$$
$$Vdin = \Delta Vdn / (-1 + (Pdn/Pdi)^{-(1/\gamma)})$$

Having calculated a set of n control chamber system initial volumes (Vdi1 to Vdin) based on the set of reference chamber pressure data points Pr1 to Prn during pressure equalization, it is now possible to select the point in time (f) that yields an optimized measure of the control chamber system initial volume (Vdi) over the entire pressure equalization period.

4) Using Equation 7, for each Vdi1 through Vdin, calculate all $\Delta Vdj,k$ using control chamber pressure measurements Pd for time points k=1 to n.

For the Vdi corresponding to Pr1:

$$\Delta Vd1, 1 = Vdi1 * (-1 + (Pd1/Pdi)^{-(1/\gamma)})$$
$$\Delta Vd1, 2 = Vdi1 * (-1 + (Pd2/Pdi)^{-(1/\gamma)})$$
$$\vdots$$
$$\Delta Vd1, n = Vdi1 * (-1 + (Pdn/Pdi)^{-(1/\gamma)})$$
$$\vdots$$

For the Vdi corresponding to Prn:

$$\Delta Vdn, 1 = Vdin * (-1 + (Pd1/Pdi)^{-(1/\gamma)})$$
$$\Delta Vdn, 2 = Vdin * (-1 + (Pd2/Pdi)^{-(1/\gamma)})$$
$$\vdots$$
$$\Delta Vdn, n = Vdin * (-1 + (Pdn/Pdi)^{-(1/\gamma)})$$

5) Take the sum-square error between the absolute values of the $\Delta Vr$'s and $\Delta Vdj,k$'s $$S_1 = \sum_{k=1}^{n} (|\Delta V_{d1,k}| - |\Delta V_{rk}|)^2$$

[S1 represents the sum-square error of $|\Delta Vd|$ minus $|\Delta Vr|$ over all data points during the equalization period when using the first data point Pr1 to determine Vdi, the control chamber system initial volume, from Vr1 and $\Delta Vr$.]

$$S_2 = \sum_{k=1}^{n} (|\Delta V_{d2,k}| - |\Delta V_{rk}|)^2$$

[S2 represents the sum-square error of $|\Delta Vr|$ minus $|\Delta Vd|$ over all data points during the equalization period when using the second data point Pr2 to determine Vdi, the control chamber system initial volume, from Vr2 and $\Delta Vr$.]

.
.
.

$$S_n = \sum_{k=1}^{n} (|\Delta V_{dn,k}| - |\Delta V_{rk}|)^2$$

6) The Pr data point between Pr1 and Prn that generates the minimum sum-square error S from step 5 (or a value that is below a desired threshold) then becomes the chosen Prf, from which Pdf and an optimized estimate of Vdi, the control chamber initial volume, can then be determined. In this example, Pdf occurs at, or about, the same time as Prf.

7) The above procedure can be applied any time that an estimate of the control chamber volume is desired, but can preferably be applied at the end of each fill stroke and each delivery stroke. The difference between the optimized Vdi at the end of a fill stroke and the optimized Vdi at the end of a corresponding delivery stroke can be used to estimate the volume of liquid delivered by the pump.

Air Detection

Another aspect of the invention involves the determination of a presence of air in the pump chamber 181, and if present, a volume of air present. Such a determination can be important, e.g., to help ensure that a priming sequence is adequately performed to remove air from the cassette 24 and/or to help ensure that air is not delivered to the patient. In certain embodiments, for example, when delivering fluid to the patient through the lower opening 187 at the bottom of the pump chamber 181, air or other gas that is trapped in the pump chamber may tend to remain in the pump chamber 181 and will be inhibited from being pumped to the patient unless the volume of the gas is larger than the volume of the effective dead space of pump chamber 181. As discussed below, the volume of the air or other gas contained in pump chambers 181 can be determined in accordance with aspects of the present invention and the gas can be purged from pump chamber 181 before the volume of the gas is larger than the volume of the effective dead space of pump chamber 181.

A determination of an amount of air in the pump chamber 181 may be made at the end of a fill stroke, and thus, may be performed without interrupting a pumping process. For example, at the end of a fill stroke during which the membrane 15 and the pump control region 1482 are drawn away from the cassette 24 such that the membrane 15/region 1482 are brought into contact with the wall of the control chamber 171, the valve X2 may be closed, and the reference chamber vented to atmospheric pressure, e.g., by opening the valve X3. Thereafter, the valves X1 and X3 may be closed, fixing the imaginary "piston" at the valve X2. The valve X2 may then be opened, allowing the pressure in the control chamber and the reference chamber to equalize, as was described above when performing pressure measurements to determine a volume for the control chamber.

If there is no air bubble in the pump chamber 181, the change in volume of the reference chamber, i.e., due to the movement of the imaginary "piston," determined using the known initial volume of the reference chamber system and the initial pressure in the reference chamber, will be equal to the change in volume of the control chamber determined using the known initial volume of the control chamber system and the initial pressure in the control chamber. (The initial volume of the control chamber may be known in conditions where the membrane 15/control region 1482 are in contact with the wall of the control chamber or in contact with the spacer elements 50 of the pump chamber 181.) However, if air is present in the pump chamber 181, the change in volume of the control chamber will actually be distributed between the control chamber volume and the air bubble(s) in the pump chamber 181. As a result, the calculated change in volume for the control chamber using the known initial volume of the control chamber system will not be equal to the calculated change in volume for the reference chamber, thus signaling the presence of air in the pump chamber.

If there is air in the pump chamber 181, the initial volume of the control chamber system Vdi is actually equal to the sum of the volume of the control chamber and lines L0 and L1 (referred to as Vdfix) plus the initial volume of the air bubble in the pump chamber 181, (referred to as Vbi), as shown in Equation 9:

$$Vdi = Vbi + Vdfix \quad (9)$$

With the membrane 15/control region 1482 pressed against the wall of the control chamber at the end of a fill stroke, the volume of any air space in the control chamber, e.g., due to the presence of grooves or other features in the control chamber wall, and the volume of the lines L0 and L1—together Vdfix—can be known quite accurately. (Similarly, with the membrane 15/control region 1482 pressed against the spacer elements 50 of the pump chamber 181, the volume of the control chamber and the lines L0 and L1 can be known accurately.) After a fill stroke, the volume of the control chamber system is tested using a positive control chamber pre-charge. Any discrepancy between this tested volume and the tested volume at the end of the fill stroke may indicate a volume of air present in the pump chamber. Substituting from Equation 9 into Equation 7, the change in volume of the control chamber ΔVd is given by:

$$\Delta Vd = (Vbi + Vdfix)(-1 + (Pdf/Pdi)^{-(1/\gamma)}) \quad (10)$$

Since ΔVr can be calculated from Equation 6, and we know from Equation 5 that ΔVr=(−1) ΔVd, Equation 10 can be re-written as:

$$(-1)\Delta Vr = (Vbi + Vdfix)(-1 + (Pdf/Pdi)^{-(1/\gamma)}) \quad (11)$$

and again as:

$$Vbi = (-1)\Delta Vr/(-1 + (Pdf/Pdi)^{-(1/\gamma)}) - Vdfix \quad (12)$$

Accordingly, the cycler 14 can determine whether there is air in the pump chamber 181, and the approximate volume of the bubble using Equation 12. This calculation of the air bubble volume may be performed if it is found, for example, that the absolute values of ΔVr (as determined from Equation 6) and ΔVd (as determined from Equation 7 using Vdi=Vdfix) are not equal to each other. That is, Vdi should be equal to Vdfix if there is no air present in the pump chamber 181, and thus the absolute value for ΔVd given by Equation 7 using Vdfix in place of Vdi will be equal to ΔVr.

After a fill stroke has been completed, and if air is detected according to the methods described above, it may be difficult to determine whether the air is located on the pump chamber side or the control side of the membrane 15. Air bubbles could be present in the liquid being pumped, or there could be residual air on the control (pneumatic) side of the pump membrane 15 because of a condition (such as, for example, an occlusion) during pumping that caused an incomplete pump stroke, and incomplete filling of the pump chamber. At this point, an adiabatic FMS measurement using a negative pump chamber pre-charge can be done. If this FMS volume matches the FMS volume with the positive precharge, then the membrane is free to move in both directions, which implies that the pump chamber is only partially filled (possibly, for example, due to an occlusion). If the value of the negative pump chamber pre-charge FMS volume equals the nominal control chamber air volume when the membrane 15/region 1482 is in contact with the inner wall of the control chamber, then it is possible to conclude that there is an air bubble in the liquid on the pump chamber side of the flexible membrane.

Head Height Detection

In some circumstances, it may be useful to determine the heightwise location of the patient relative to the cassette 24 or other portion of the system. For example, dialysis patients in some circumstances can sense a "tugging" or other motion due to fluid flowing into or out of the patient's peritoneal cavity during a fill or drain operation. To reduce this sensation, the cycler 14 may reduce the pressure applied to the patient line 34 during fill and/or drain operations. However, to suitably set the pressure for the patient line 34, the cycler 14 may determine the height of the patient relative to the cycler 14, the heater bag 22, drain or other portion of the system. For example, when performing a fill operation, if the patient's peritoneal cavity is located 5 feet above the heater bag 22 or the cassette 24, the cycler 14 may need to use a higher pressure in the patient line 34 to deliver dialysate than if the patient's peritoneal cavity is located 5 ft below the cycler 14. The pressure may be adjusted, for example, by alternately opening and closing a binary pneumatic source valve for variable time intervals to achieve the desired target pump chamber pressure. An average desired target pressure can be maintained, for example, by adjusting the time intervals to keep the valve open when the pump chamber pressure is below the target pressure by a specified amount, and to keep the valve closed when the pump chamber pressure is above the target pressure by a specified amount. Any adjustments to maintain the delivery of a complete stroke volume can be made by adjusting the fill and/or delivery times of the pump chamber. If a variable orifice source valve is used, the target pump chamber pressure can be reached by varying the orifice of the source valve in addition to timing the intervals during which the valve is opened and closed. To adjust for patient position, the cycler 14 may momentarily stop pumping of fluid, leaving the patient line 34 in open fluid communication with one or more pump chambers 181 in the cassette (e.g., by opening suitable valve ports in the cassette 24). However, other fluid lines may be closed, such as the upper valve ports 192 for the pump chambers 181. In this condition, the pressure in the control chamber for one of the pumps may be measured. As is well known in the art, this pressure correlates with the "head" height of the patient, and can be used by the cycler 14 to control the delivery pressure of fluid to the patient. A similar approach can be used to determine the "head" height of the heater bag 22 (which will generally be known), and/or the solution containers 20, as the head height of these components may have an effect on pressure needed for pumping fluid in a suitable way.

Noise Reduction Features of the Cycler

In accordance with aspects of the invention, the cycler 14 may include one or more features to reduce noise generated by the cycler 14 during operation and/or when idle. In one aspect of the invention, the cycler 14 may include a single pump that generates both pressure and vacuum that are used to control the various pneumatic systems of the cycler 14. In one embodiment, the pump can simultaneously generate both pressure and vacuum, thereby reducing overall run time, and allowing the pump to run more slowly (and thus more quietly). In another embodiment, the air pump start and/or stop may be ramped, e.g., slowly increases pump speed or power output at starting and/or slowly decreases pump speed or power output at shut down. This arrangement may help reduce "on/off" noise associated with start and stop of the air pump so pump noise is less noticeable. In another embodiment, the air pump may be operated at a lower duty cycle when nearing a target output pressure or volume flow rate so that the air pump can continue operating as opposed to shutting off, only to be turned on after a short time. As a result, disruption caused by repeated on and off cycles of the air pump may be avoided.

Figure 44:
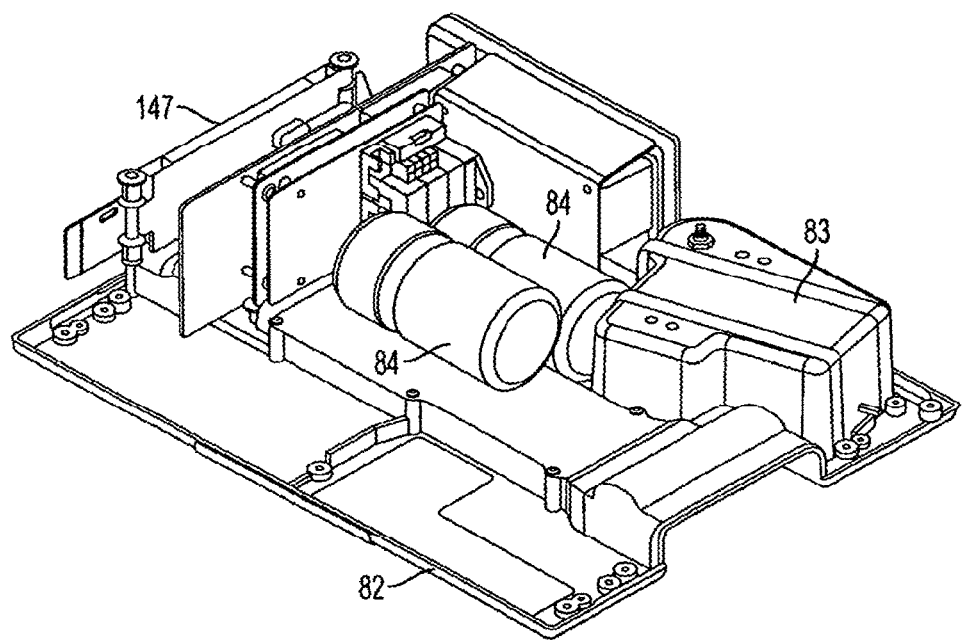
FIG. 44 is a perspective view of an interior section of the cycler of FIG. 10 with the upper portion of the housing removed.

FIG. 44 shows a perspective view of an interior section of the cycler 14 with the upper portion of the housing 82 removed. In this illustrative embodiment, the cycler 14 includes a single air pump 83, which includes the actual pump and motor drive contained within a sound barrier enclosure. The sound barrier enclosure includes an outer shield, such as a metal or plastic frame, and a sound insulation material within the outer shield and at least partially surrounding the motor and pump. This air pump 83 may simultaneously provide air pressure and vacuum, e.g., to a pair of accumulator tanks 84. One of the tanks 84 may store positive pressure air, while the other stores vacuum. A suitable manifold and valve arrangement may be coupled to the tanks 84 so as to provide and control air pressure/vacuum supplied to the components of the cycler 14.

In accordance with another aspect of the invention, components that require a relatively constant pressure or vacuum supply during cycler operation, such as an occluder, may be isolated from the source of air pressure/vacuum at least for relatively long periods of time. For example, the occluder 147 in the cycler 14 generally requires a constant air pressure in the occluder bladder 166 so that the patient and drain lines remain open for flow. If the cycler 14 continues to operate properly without power failure, etc., the bladder 166 may be inflated once at the beginning of system operation and remain inflated until shut down. The inventors have recognized that in some circumstances air powered devices that are relatively static, such as the bladder 166, may "creak" or otherwise make noise in response to slight variations in supplied air pressure. Such variations may cause the bladder 166 to change size slightly, which causes associated mechanical parts to move and potentially make noise. In accordance with an aspect of the bladder 166 and other components having similar pneumatic power requirements, may be isolated from the air pump 83 and/or the tanks 84, e.g., by the closing of a valve, so as to reduce variations of pressure in the bladder or other pneumatic component, thus reducing noise that may be generated as a result of pressure variations. Another component that may be isolated from the pneumatic supply is the bladder in the door 141 at the cassette mounting location 145 which inflates to press the cassette 24 against the control surface 148 when the door 141 is closed. Other suitable components may be isolated as desired.

In accordance with another aspect of the invention, the speed and/or force at which pneumatic components are actuated may be controlled to as to reduce noise generated by component operation. For example, movement of the valve control regions 1481 to move a corresponding portion of the cassette membrane 15 so as to open or close a valve port on the cassette 24 may cause a "popping" noise as the membrane 15 slaps against and/or pull away from the cassette 24. Such noise may be reduced by controlling the rate of operation of the valve control regions 1481, e.g., by restricting the flow rate of air used to move the control regions 1481. Air flow may be restricted by, for example, providing a suitably small sized orifice in the line leading to the associated control chamber, or in other ways.

A controller may also be programmed to apply pulse width modulation ("PWM") to the activation of one or more pneumatic source valves at a manifold of cycler 14. The pneumatic pressure delivered to various valves and pumps of cassette 24 can be controlled by causing the associated manifold source valves to open and close repeatedly during the period of actuation of a valve or pump in cassette 24. The rate of rise or fall of pressure against membrane 15/control surface 148 can then be controlled by modulating the duration of the "on" portion of the particular manifold valve during the actuation period. An additional advantage of applying PWM to the manifold source valves is that variable pneumatic pressure can be delivered to the cassette 24 components using only a binary (on-off) source valve, rather than a more expensive and potentially less reliable variable-orifice source valve.

In accordance with another aspect of the invention, the movement of one or more valve elements may be suitably damped so as to reduce noise generated by valve cycling. For example, a fluid (such as a ferro fluid) may be provided with the valve element of high frequency solenoid valves to damp the movement of the element and/or reduce noise generated by movement of the valve element between open and closed positions.

In accordance with another embodiment, pneumatic control line vents may be connected together and/or routed into a common, sound-insulated space so that noise associated with air pressure or vacuum release may be reduced. For example, when the occluder bladder 166 is vented to allow the spring plates 165 to move toward each other and occlude one or more lines, the air pressure released may be released into a sound insulated enclosure, as opposed to being released into a space where noise associated with the release may be heard more easily. In another embodiment, lines that are arranged to release air pressure may be connected together with lines that are arranged to release an air vacuum. With this connection (which may include a vent to atmosphere, an accumulator or other), noise generated by pressure/vacuum release may be further reduced.

Control System

The control system 16 described in connection with FIG. 1 has a number of functions, such as controlling dialysis therapy and communicating information related to the dialysis therapy. While these functions may be handled by a single computer or processor, it may be desirable to use different computers for different functions so that the implementations of those functions are kept physically and conceptually separate. For example, it may be desirable to use one computer to control the dialysis machinery and another computer to control the user interface.

Figure 45:
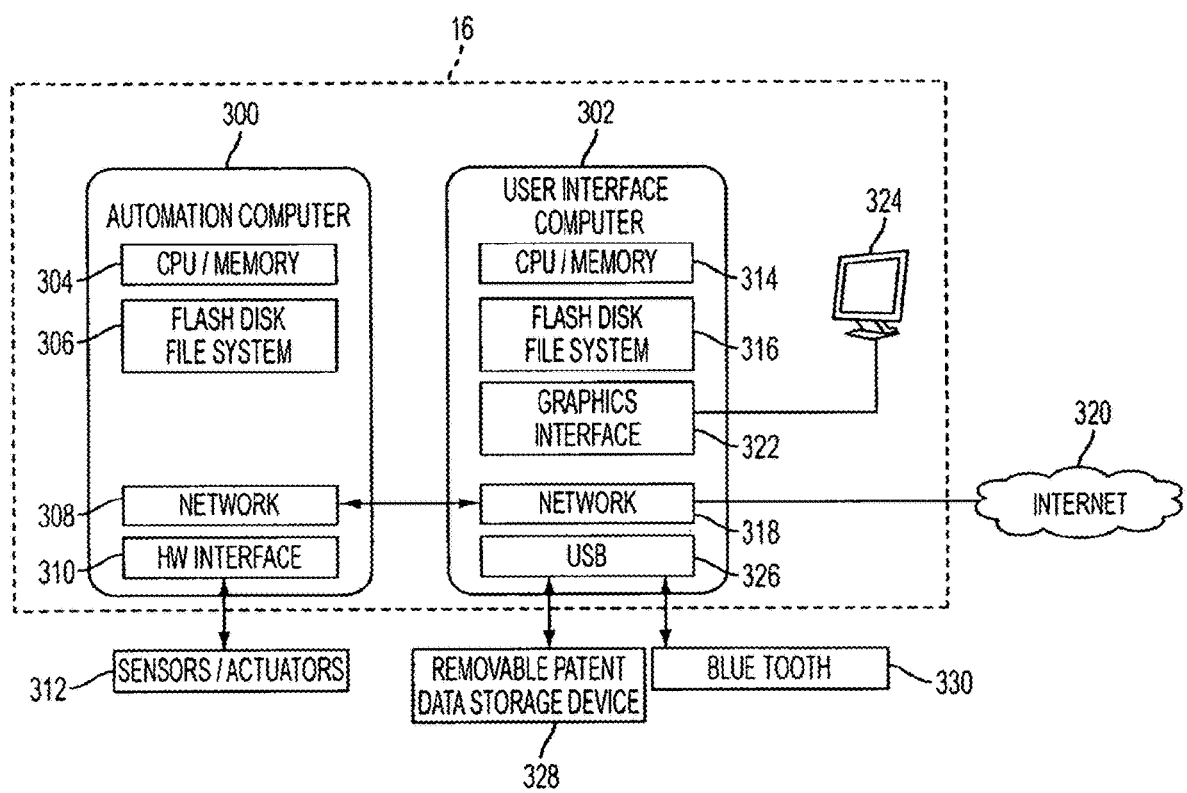
FIG. 45 is a schematic block diagram illustrating an exemplary implementation of control system for an APD system.

FIG. 45 shows a block diagram illustrating an exemplary implementation of control system 16, wherein the control system comprises a computer that controls the dialysis machinery (an "automation computer" 300) and a separate computer that controls the user interface (a "user interface computer" 302). As will be described, safety-critical system functions may be run solely on the automation computer 300, such that the user interface computer 302 is isolated from executing safety-critical functions.

The automation computer 300 controls the hardware, such as the valves, heaters and pumps, that implement the dialysis therapy. In addition, the automation computer 300 sequences the therapy and maintains a "model" of the user interface, as further described herein. As shown, the automation computer 300 comprises a computer processing unit (CPU)/memory 304, a flash disk file system 306, a network interface 308, and a hardware interface 310. The hardware interface 310 is coupled to sensors/actuators 312. This coupling allows the automation computer 300 to read the sensors and control the hardware actuators of the APD system to monitor and perform therapy operations. The network interface 308 provides an interface to couple the automation computer 300 to the user interface computer 302.

The user interface computer 302 controls the components that enable data exchange with the outside world, including the user and external devices and entities. The user interface computer 302 comprises a computer processing unit (CPU)/memory 314, a flash disk file system 316, and a network interface 318, each of which may be the same as or similar to their counterparts on the automation computer 300. The Linux operating system may run on each of the automation computer 300 and the user interface computer 302. An exemplary processor that may be suitable for use as the CPU of the automation computer 300 and/or for use as the CPU of the user interface computer 302 is Freescale's Power PC 5200B®.

Via the network interface 318, the user interface computer 302 may be connected to the automation computer 300. Both the automation computer 300 and the user interface computer 302 may be included within the same chassis of the APD system. Alternatively, one or both computers or a portion of said computers (e.g., display 324) may be located outside of the chassis. The automation computer 300 and the user interface computer 302 may be coupled by a wide area network, a local area network, a bus structure, a wireless connection, and/or some other data transfer medium.

The network interface 318 may also be used to couple the user interface computer 302 to the Internet 320 and/or other networks. Such a network connection may be used, for example, to initiate connections to a clinic or clinician, upload therapy data to a remote database server, obtain new prescriptions from a clinician, upgrade application software, obtain service support, request supplies, and/or export data for maintenance use. According to one example, call center technicians may access alarm logs and machine configuration information remotely over the Internet 320 through the network interface 318. If desired, the user interface computer 302 may be configured such that connections may only be initiated by the user or otherwise locally by the system, and not by remote initiators.

The user interface computer 302 also comprises a graphics interface 322 that is coupled to a user interface, such as the user interface 144 described in connection with FIG. 10. According to one exemplary implementation, the user interface comprises a display 324 that includes a liquid crystal display (LCD) and is associated with a touchscreen. For example, a touchscreen may be overlaid on the LCD so that the user can provide inputs to the user interface computer 302 by touching the display with a finger, stylus or the like. The display may also be associated with an audio system capable of playing, among other things, audio prompts and recorded speech. The user may adjust the brightness of the display 324 based on their environment and preference. Optionally, the APD system may include a light sensor, and the brightness of the display may be adjusted automatically in response to the amount of ambient light detected by the light sensor.

Figure 65:
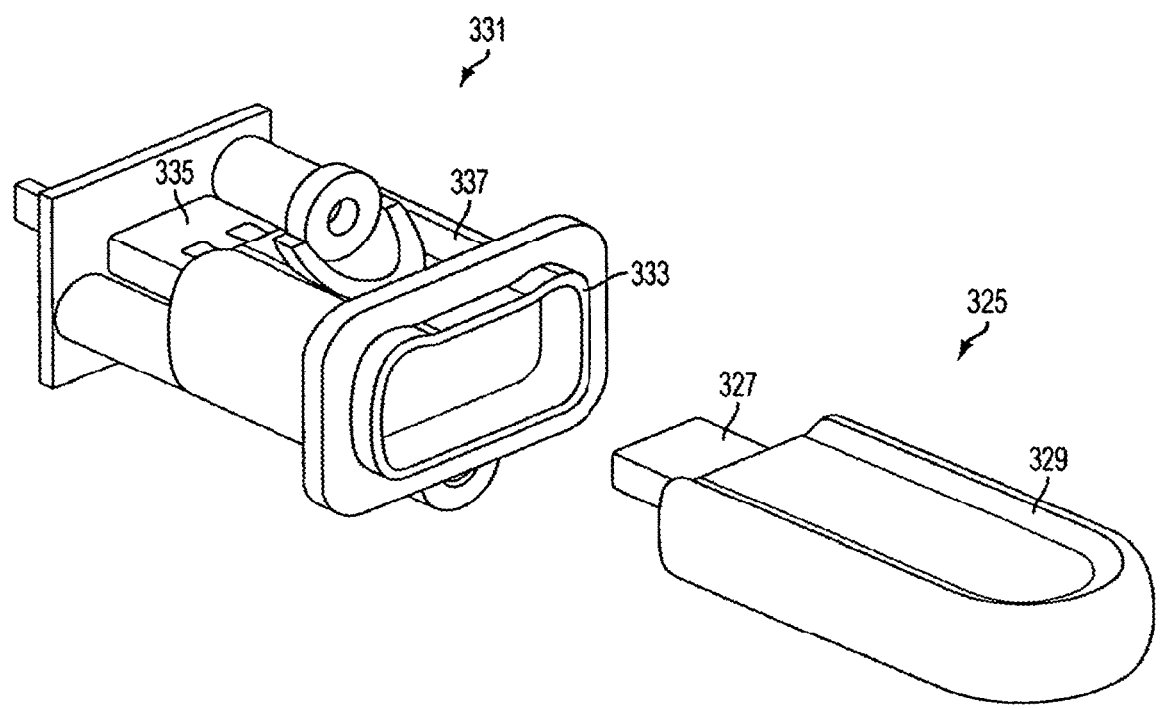
FIG. 65 shows an exemplary patient data key and associated port for transferring patient data to and from the APD system.

In addition, the user interface computer 302 comprises a USB interface 326. A data storage device 328, such as a USB flash drive, may be selectively coupled to the user interface computer 302 via the USB interface 326. The data storage device 328 may comprise a "patient data key" used to store patient-specific data. Data from dialysis therapies and/or survey questions (e.g., weight, blood pressure) may be logged to the patient data key. In this way, patient data may be accessible to the user interface computer 302 when coupled to the USB interface 326 and portable when removed from the interface. The patient data key may be used for transferring data from one system or cycler to another during a cycler swap, transferring new therapy and cycler configuration data from clinical software to the system, and transferring treatment history and device history information from the system to clinical software. An exemplary patient data key 325 is shown in FIG. 65.

As shown, the patient data key 325 comprises a connector 327 and a housing 329 coupled to the connector. The patient data key 325 may be optionally be associated with a dedicated USB port 331. The port 331 comprises a recess 333 (e.g., in the chassis of the APD system) and a connector 335 disposed within the recess. The recess may be defined, at least in part, by a housing 337 associated with the port 331. The patient data key connector 327 and the port connector 335 are adapted to be selectively electrically and mechanically coupled to each other. As may be appreciated from FIG. 65, when the patient data key connector 327 and the port connector 335 are coupled, the housing 329 of the patient data storage device 325 is received at least partially within the recess 333.

The housing 329 of the patient data key 325 may include visual cues indicative of the port with which it is associated and/or be shaped to prevent incorrect insertion. For example, the recess 333 and/or housing 337 of the port 331 may have a shape corresponding to the shape of the housing 329 of the patient data key 325. For example, each may have a non-rectangular or otherwise irregular shape, such as an oblong shape with an upper indentation as shown in FIG. 65. The recess 333 and/or housing 337 of the port 331 and the housing 329 of the patient data key 325 may include additional visual cues to indicate their association. For example, each may be formed of the same material and/or have the same or a similar color and/or pattern.

Alternatively or additionally, the patient data key 325 may comprise a verification code that is readable by the APD system to verify that the patient data key is of an expected type and/or origin. Such a verification code may be stored in a memory of the patient data key 325, and be read from the patient data key and processed by a processor of the APD system. Alternatively or additionally, such a verification code may be included on an exterior of the patient data key 325, e.g., as a barcode or numeric code. In this case, the code may be read by a camera and associated processor, a barcode scanner, or another code reading device.

If the patient data key is not inserted when the system is powered on, an alert may be generated requesting that the key be inserted. However, the system may be able to run without the patient data key as long as it has been previously configured. Thus, a patient who has lost their patient data key may receive therapy until a replacement key can be obtained. Data may be stored directly to the patient data key or transferred to the patient data key after storage on the user interface computer 302. Data may also be transferred from the patient data key to the user interface computer 302.

In addition, a USB Bluetooth® adapter 330 may be coupled to the user interface computer 302 via the USB interface 326 to allow, for example, data to be exchanged with nearby Bluetooth®-enabled devices. For example, a Bluetooth®-enabled scale in the vicinity of the APD system may wirelessly transfer information concerning a patient's weight to the system via the USB interface 326 using the USB Bluetooth® adapter 330. Similarly, a Bluetooth®-enabled blood pressure cuff may wirelessly transfer information concerning a patient's blood pressure to the system using the USB Bluetooth® adapter 330. The Bluetooth® adapter may be built-in to the user interface computer 302 or may be external (e.g., a Bluetooth® dongle).

The USB interface 326 may comprise several ports, and these ports may have different physical locations and be used for different USB device. For example, it may be desirable to make the USB port for the patient data key accessible from the front of the machine, while another USB port may be provided at and accessible from the back of the machine. A USB port for the Bluetooth® connection may be included on the outside of the chassis, or instead be located internal to the machine or inside the battery door, for example.

As noted above, functions that could have safety-critical implications may be isolated on the automation computer. Safety-critical information relates to operations of the APD system. For example, safety-critical information may comprise a state of a APD procedure and/or the algorithms for implementing or monitoring therapies. Non safety-critical information may comprise information that relates to the visual presentation of the screen display that is not material to the operations of the APD system.

By isolating functions that could have safety-critical implications on the automation computer 300, the user interface computer 302 may be relieved of handling safety-critical operations. Thus, problems with or changes to the software that executes on the user interface computer 302 will not affect the delivery of therapy to the patient. Consider the example of graphical libraries (e.g., Trolltech's Qt® toolkit), which may be used by the user interface computer 302 to reduce the amount of time needed to develop the user interface view. Because these libraries are handled by a process and processor separate from those of the automation computer 300, the automation computer is protected from any potential flaws in the libraries that might affect the rest of the system (including safety-critical functions) were they handled by the same processor or process.

Of course, while the user interface computer 302 is responsible for the presentation of the interface to the user, data may also be input by the user using the user interface computer 302, e.g., via the display 324. To maintain the isolation between the functions of the automation computer 300 and the user interface computer 302, data received via the display 324 may be sent to the automation computer for interpretation and returned to the user interface computer for display.

Although FIG. 45 shows two separate computers, separation of the storage and/or execution of safety-critical functions from the storage and/or execution of non safety-critical functions may be provided by having a single computer including separate processors, such as CPU/memory components 304 and 314. Thus, it should be appreciated that providing separate processors or "computers" is not necessary. Further, a single processor may alternatively be used to perform the functions described above. In this case, it may be desirable to functionally isolate the execution and/or storage of the software components that control the dialysis machinery from those that control the user interface, although the invention is not limited in this respect.

Other aspects of the system architecture may also be designed to address safety concerns. For example, the automation computer 300 and user interface computer 302 may include a "safe line" that can be enabled or disabled by the CPU on each computer. The safe line may be coupled to a voltage supply that generates a voltage (e.g., 12 V) sufficient to enable at least some of the sensors/actuators 312 of the APD system. When both the CPU of the automation computer 300 and the CPU of the user interface computer 302 send an enable signal to the safe line, the voltage generated by the voltage supply may be transmitted to the sensors/actuators to activate and disable certain components. The voltage may, for example, activate the pneumatic valves and pump, disable the occluder, and activate the heater. When either CPU stops sending the enable signal to the safe line, the voltage pathway may be interrupted (e.g., by a mechanical relay) to deactivate the pneumatic valves and pump, enable the occluder, and deactivate the heater. In this way, when either the automation computer 300 or the user interface computer 302 deems it necessary, the patient may be rapidly isolated from the fluid path, and other activities such as heating and pumping may be stopped. Each CPU can disable the safe line at any time, such as when a safety-critical error is detected or a software watchdog detects an error. The system may be configured such that, once disabled, the safe line may not be re-enabled until both the automation computer 300 and user interface computer 302 have completed self-tests.

Figure 46:
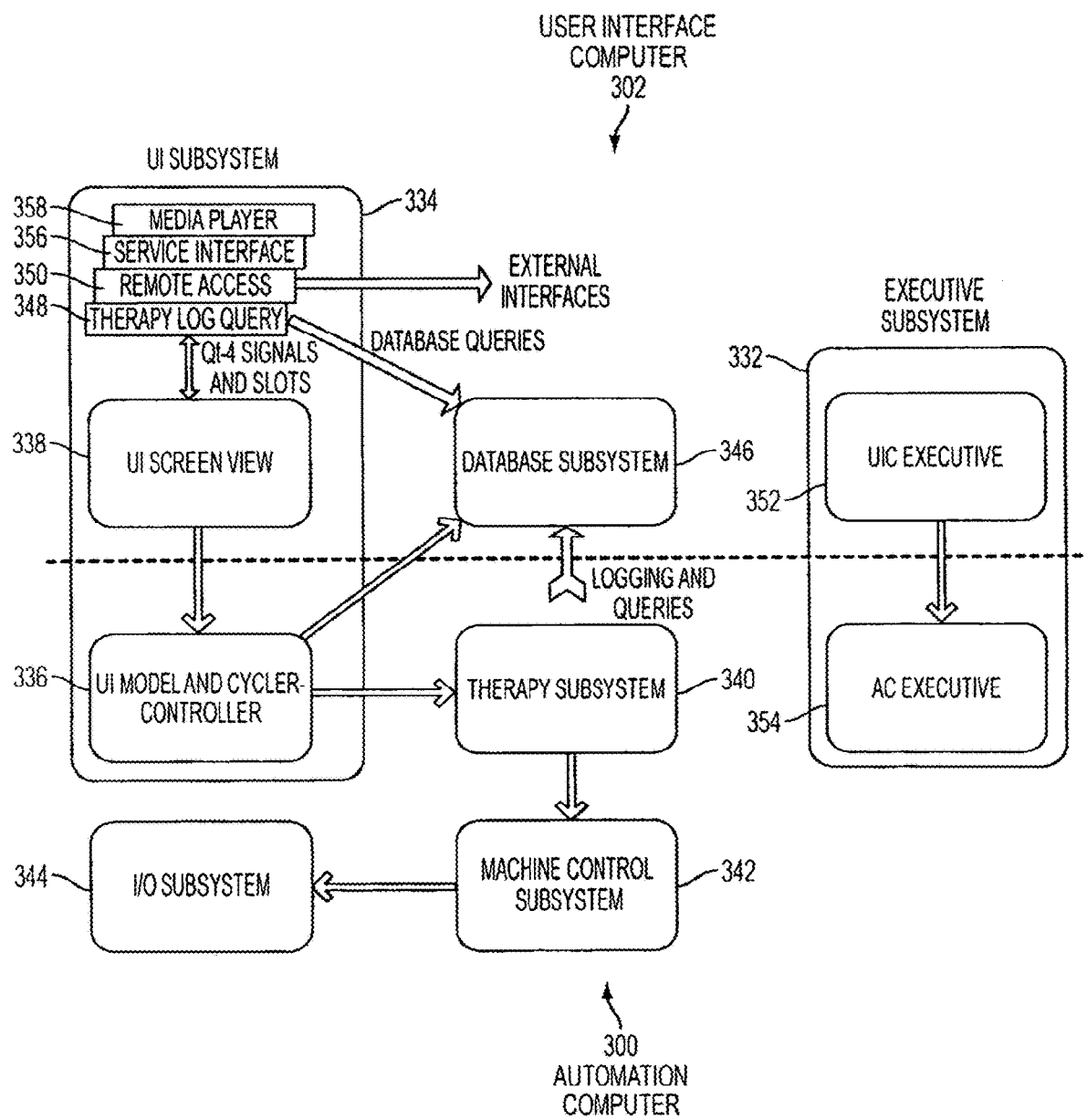
FIG. 46 is a schematic block diagram of illustrative software subsystems of a user interface computer and the automation computer for the control system of FIG. 45.

FIG. 46 shows a block diagram of the software subsystems of the user interface computer 302 and the automation computer 300. In this example, a "subsystem" is a collection of software, and perhaps hardware, assigned to a specific set of related system functionality. A "process" may be an independent executable which runs in its own virtual address space, and which passes data to other processes using inter-process communication facilities.

The executive subsystem 332 includes the software and scripts used to inventory, verify, start and monitor the execution of the software running on the CPU of the automation computer 300 and the CPU of the user interface computer 302. A custom executive process is run on each of the foregoing CPUs. Each executive process loads and monitors the software on its own processor and monitors the executive on the other processor.

The user interface (UI) subsystem 334, handles system interactions with the user and the clinic. The UI subsystem 334 is implemented according to a "model-view-controller" design pattern, separating the display of the data ("view") from the data itself ("model"). In particular, system state and data modification functions ("model") and cycler control functions ("controller") are handled by the UI model and cycler controller 336 on the automation computer 300, while the "view" portion of the subsystem is handled by the UI screen view 338 on the UI computer 302. Data display and export functionality, such as log viewing or remote access, may be handled entirely by the UI screen view 338. The UI screen view 338 monitors and controls additional applications, such as those that provide log viewing and a clinician interface. These applications are spawned in a window controlled by the UI screen view 338 so that control can be returned to the UI screen view 338 in the case of an alert, an alarm or an error.

The therapy subsystem 340 directs and times the delivery of the dialysis treatment. It may also be responsible verifying a prescription, calculating the number and duration of therapy cycles based upon the prescription, time and available fluids, controlling the therapy cycles, tracking fluid in the supply bags, tracking fluid in the heater bag, tracking the amount of fluid in the patient, tracking the amount of ultra-filtrate removed from patient, and detecting alert or alarm conditions.

The machine control subsystem 342 controls the machinery used to implement the dialysis therapy, orchestrating the high level pumping and control functionality when called upon by the therapy subsystem 340. In particular, the following control functions may be performed by the machine control subsystem 342: air compressor control; heater control; fluid delivery control (pumping); and fluid volume measurement. The machine control subsystem 342 also signals the reading of sensors by the I/O subsystem 344, described below.

The I/O subsystem 344 on the automation computer 300 controls access to the sensors and actuators used to control the therapy. In this implementation, the I/O subsystem 344 is the only application process with direct access to the hardware. Thus, the I/O subsystem 344 publishes an interface to allow other processes to obtain the state of the hardware inputs and set the state of the hardware outputs.

The database subsystem 346, also on the user interface computer 302, stores all data to and retrieves all data from the databases used for the onboard storage of machine, patient, prescription, user-entry and treatment history information. This provides a common access point when such information is needed by the system. The interface provided by the database subsystem 346 is used by several processes for their data storage needs. The database subsystem 346 also manages database file maintenance and back-up.

The UI screen view 338 may invoke a therapy log query application to browse the therapy history database. Using this application, which may alternatively be implemented as multiple applications, the user can graphically review their treatment history, their prescription and/or historical machine status information. The application transmits database queries to the database subsystem 346. The application can be run while the patient is dialyzing without impeding the safe operation of the machine.

The remote access application, which may be implemented as a single application or multiple applications, provides the functionality to export therapy and machine diagnostic data for analysis and/or display on remote systems. The therapy log query application may be used to retrieve information requested, and the data may be reformatted into a machine neutral format, such as XML, for transport. The formatted data may be transported off-board by a memory storage device, direct network connection or other external interface 348. Network connections may be initiated by the APD system, as requested by the user.

The service interface 356 may be selected by the user when a therapy is not in progress. The service interface 356 may comprise one or more specialized applications that log test results and optionally generate a test report which can be uploaded, for example, to a diagnostic center. The media player 358 may, for example, play audio and/or video to be presented to a user.

According to one exemplary implementation, the databases described above are implemented using SQLite, a software library that implements a self-contained, serverless, zero-configuration, transactional SQL database engine.

The executive subsystem 332 implements two executive modules, the user interface computer (UIC) executive 352 on the user interface computer 302 and the automation computer (AC) executive 354 on the automation computer 300. Each executive is started by the startup scripts that run after the operating system is booted and includes a list of processes it starts. As the executives go through their respective process lists, each process image is checked to ensure its integrity in the file system before the process is launched. The executives monitor each child process to ensure that each starts as expected and continue monitoring the child processes while they run, e.g., using Linux parent-child process notifications. When a child process terminates or fails, the executive either restarts it (as in the case of the UI view) or places the system in fail safe mode to ensure that the machine behaves in a safe manner. The executive processes are also responsible for cleanly shutting down the operating system when the machine is powering off.

The executive processes communicate with each other allowing them to coordinate the startup and shutdown of the various application components. Status information is shared periodically between the two executives to support a watchdog function between the processors. The executive subsystem 332 is responsible for enabling or disabling the safe line. When both the UIC executive 352 and the AC executive 354 have enabled the safe line, the pump, the heater, and the valves can operate. Before enabling the lines, the executives test each line independently to ensure proper operation. In addition, each executive monitors the state of the other's safe line.

The UIC executive 352 and the AC executive 354 work together to synchronize the time between the user interface computer 302 and the automation computer 300. The time basis is configured via a battery backed real-time clock on the user interface computer 302 that is accessed upon startup. The user interface computer 302 initializes the CPU of the automation computer 300 to the real-time clock. After that, the operating system on each computer maintains its own internal time. The executives work together to ensure sufficiently timekeeping by periodically performing power on self tests. An alert may be generated if a discrepancy between the automation computer time and the user interface computer time exceeds a given threshold.

Figure 47:
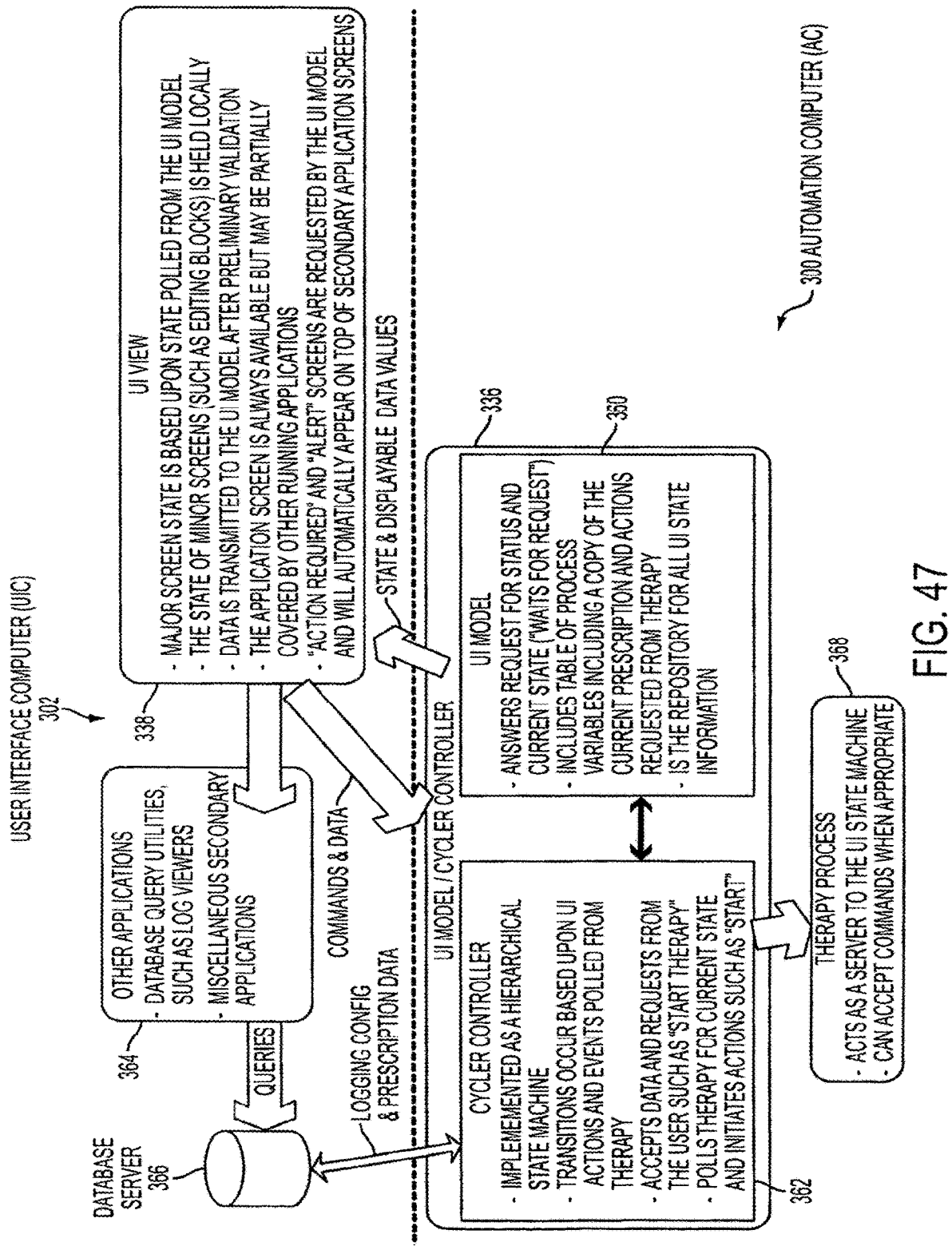
FIG. 47 shows a flow of information between various subsystems and processes of the APD system in an illustrative embodiment.

FIG. 47 shows the flow of information between various subsystems and processes of the APD system. As discussed previously, the UI model 360 and cycler controller 362 run on the automation computer. The user interface design separates the screen display, which is controlled by the UI view 338, from the screen-to-screen flow, which is controlled by the cycler controller 362, and the displayable data items, which are controlled by the UI model 360. This allows the visual representation of the screen display to be changed without affecting the underlying therapy software. All therapy values and context are stored in the UI model 360, isolating the UI view 338 from the safety-critical therapy functionality.

The UI model 360 aggregates the information describing the current state of the system and patient, and maintains the information that can be displayed via the user interface. The UI model 360 may update a state that is not currently visible or otherwise discernable to the operator. When the user navigates to a new screen, the UI model 360 provides the information relating to the new screen and its contents to the UI view 338. The UI model 360 exposes an interface allowing the UI view 338 or some other process to query for current user interface screen and contents to display. The UI model 360 thus provides a common point where interfaces such as the remote user interface and online assistance can obtain the current operational state of the system.

The cycler controller 362 handles changes to the state of the system based on operator input, time and therapy layer state. Acceptable changes are reflected in the UI model 360. The cycler controller 362 is implemented as a hierarchical state machine that coordinates therapy layer commands, therapy status, user requests and timed events, and provides view screen control via UI model 360 updates. The cycler controller 362 also validates user inputs. If the user inputs are allowed, new values relating to the user inputs are reflected back to the UI view 338 via the UI model 360. The therapy process 368 acts as a server to the cycler controller 362. Therapy commands from the cycler controller 362 are received by the therapy process 368.

The UI view 338, which runs on the UI computer 302, controls the user interface screen display and responds to user input from the touch screen. The UI view 338 keeps track of local screen state, but does not maintain machine state information. Machine state and displayed data values, unless they are in the midst of being changed by the user, are sourced from the UI model 360. If the UI view 338 terminates and is restarted, it displays the base screen for the current state with current data. The UI view 338 determines which class of screens to display from the UI model 360, which leaves the presentation of the screen to the UI view. All safety-critical aspects of the user interface are handled by the UI model 360 and cycler controller 362.

The UI view 338 may load and execute other applications 364 on the user interface computer 302. These applications may perform non-therapy controlling tasks. Exemplary applications include the log viewer, the service interface, and the remote access applications. The UI view 338 places these applications within a window controlled by the UI view, which allows the UI view to display status, error, and alert screens as appropriate. Certain applications may be run during active therapy. For example, the log viewer may be run during active therapy, while the service interface and the remote access application generally may not. When an application subservient to the UI view 338 is running and the user's attention is required by the ongoing therapy, the UI view 338 may suspend the application and regain control of the screen and input functions. The suspended application can be resumed or aborted by the UI view 338.

Figure 48:
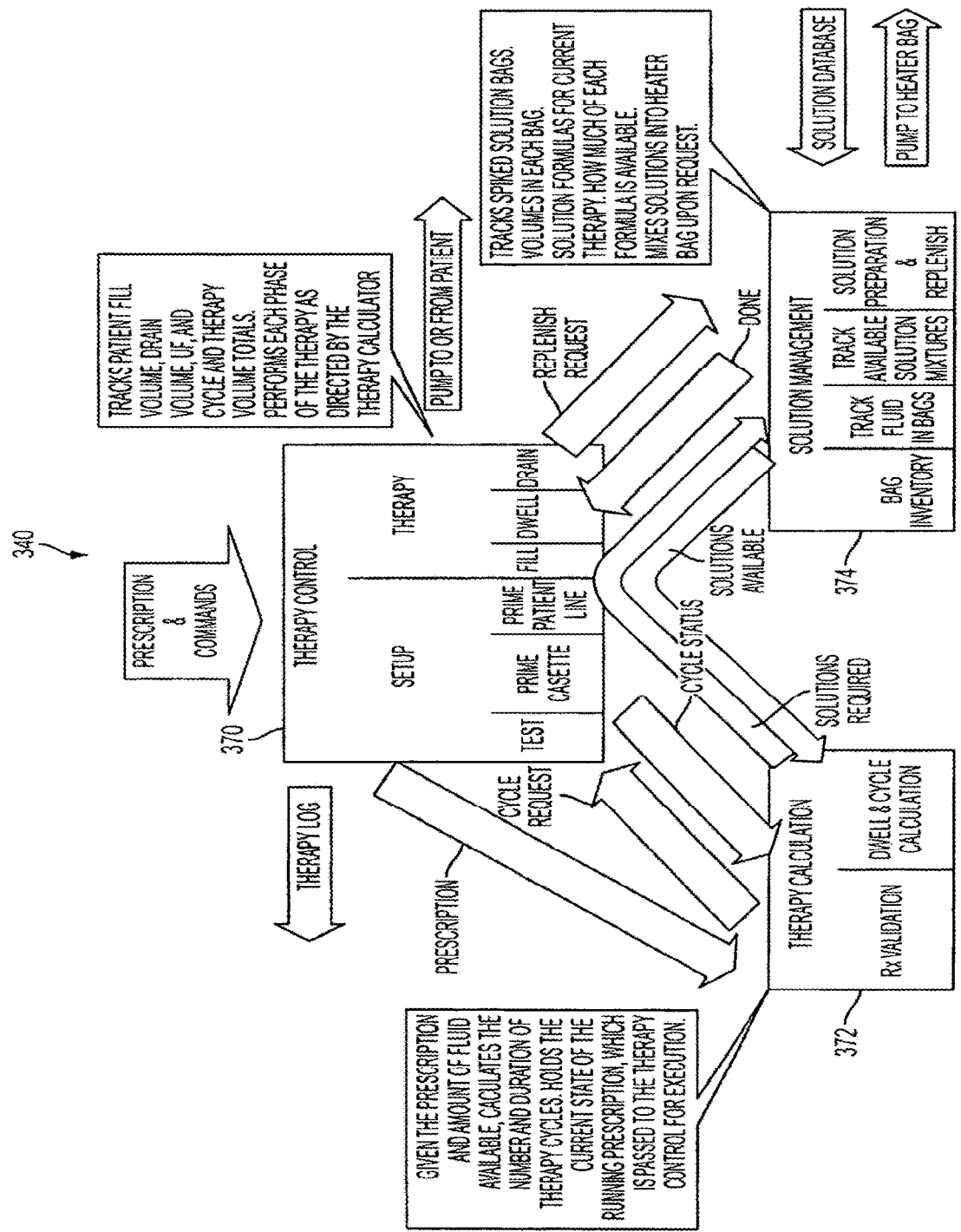
FIG. 48 illustrates an operation of the therapy subsystem of FIG. 46.

FIG. 48 illustrates the operation of the therapy subsystem 340 described in connection with FIG. 46. The therapy subsystem 340 functionality is divided across three processes: therapy control; therapy calculation; and solution management. This allows for functional decomposition, ease of testing, and ease of updates.

The therapy control module 370 uses the services of the therapy calculation module 372, solution management module 374 and machine control subsystem 342 (FIG. 46) to accomplish its tasks. Responsibilities of the therapy control module 370 include tracking fluid volume in the heater bag, tracking fluid volume in the patient, tracking patient drain volumes and ultra filtrate, tracking and logging cycle volumes, tracking and logging therapy volumes, orchestrating the execution of the dialysis therapy (drain-fill-dwell), and controlling therapy setup operations. The therapy control module 370 performs each phase of the therapy as directed by the therapy calculation module 370.

The therapy calculation module 370 tracks and recalculates the drain-fill-dwell cycles that comprise a peritoneal dialysis therapy. Using the patient's prescription, the therapy calculation module 372 calculates the number of cycles, the dwell time, and the amount of solution needed (total therapy volume). As the therapy proceeds, a subset of these values is recalculated, accounting for the actual elapsed time. The therapy calculation module 372 tracks the therapy sequence, passing the therapy phases and parameters to the therapy control module 370 when requested.

The solution management module 374 maps the placement of solution supply bags, tracks the volume in each supply bag, commands the mixing of solutions based upon recipes in the solution database, commands the transfer of the requested volume of mixed or unmixed solution into the heater bag, and tracks the volume of mixed solutions available using the solution recipe and available bag volume.

Figure 49:
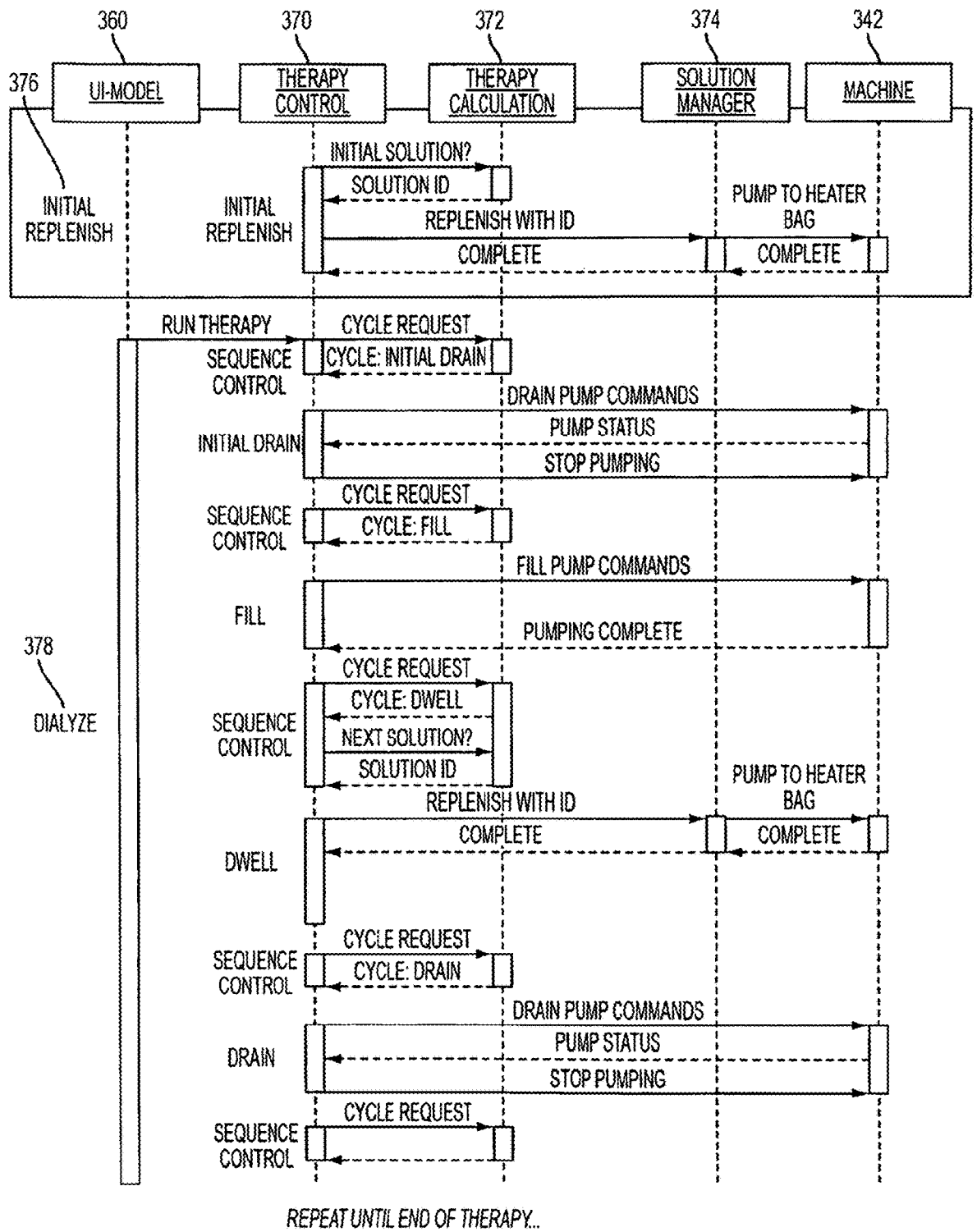
FIG. 49 shows a sequence diagram depicting exemplary interactions of therapy module processes during initial replenish and dialyze portions of the therapy.

FIG. 49 shows a sequence diagram depicting exemplary interactions of the therapy module processes described above during the initial replenish and dialyze portions of the therapy. During the exemplary initial replenish process 376, the therapy control module 370 fetches the solution ID and volume for the first fill from the therapy calculation module 372. The solution ID is passed to the solution management module 374 with a request to fill the heater bag with solution, in preparation for priming the patient line and the first patient fill. The solution management module 374 passes the request to the machine control subsystem 342 to begin pumping the solution to the heater bag.

During the exemplary dialyze process 378, the therapy control module 370 executes one cycle (initial drain, fill, dwell-replenish, and drain) at a time, sequencing these cycles under the control of the therapy calculation module 372. During the therapy, the therapy calculation module 372 is updated with the actual cycle timing, so that it can recalculate the remainder of the therapy if needed.

In this example, the therapy calculation module 372 specifies the phase as "initial drain," and the therapy control module makes the request to the machine control subsystem 342. The next phase specified by the therapy calculation module 372 is "fill." The instruction is sent to the machine control subsystem 342. The therapy calculation module 372 is called again by the therapy control module 370, which requests that fluid be replenished to the heater bag during the "dwell" phase. The solution management module 374 is called by the therapy control module 370 to replenish fluid in the heater bag by calling the machine control subsystem 342. Processing continues with therapy control module 370 calling the therapy calculation module 372 to get the next phase. This is repeated until there are no more phases, and the therapy is complete.

Alert/Alarm Functions

Conditions or events in the APD system may trigger alerts and/or alarms that are logged, displayed to a user, or both. These alerts and alarms are a user interface construct that reside in the user interface subsystem, and may be triggered by conditions that occur in any part of the system. These conditions may be grouped into three categories: (1) system error conditions, (2) therapy conditions, and (3) system operation conditions.

"System error conditions" relate to errors detected in software, memory, or other aspects of the processors of the APD system. These errors call the reliability of the system into question, and may be considered "unrecoverable." System error conditions cause an alarm that is displayed or otherwise made known to the user. The alarm may also be logged. Since system integrity cannot be guaranteed in the instance of a system error condition, the system may enter a fail safe mode in which the safe line described herein is disabled.

Each subsystem described in connection with FIG. 46 is responsible for detecting its own set of system errors. System errors between subsystems are monitored by the user interface computer executive 352 and automation computer executives 354. When a system error originates from a process running on the user interface computer 302, the process reporting the system error terminates. If the UI screen view subsystem 338 is terminated, the user interface computer executive 352 attempts to restart it, e.g., up to a maximum of three times. If it fails to restart the UI screen view 338 and a therapy is in progress, the user interface computer executive 352 transitions the machine to a fail safe mode.

When a system error originates from a process running on the automation computer 300, the process terminates. The automation computer executive 354 detects that the process has terminated and transitions to a safe state if a therapy is in progress.

When a system error is reported, an attempt is made to inform the user, e.g., with visual and/or audio feedback, as well as to log the error to a database. System error handling is encapsulated in the executive subsystem 332 to assure uniform handling of unrecoverable events. The executive processes of the UIC executive 352 and AC executive 354 monitor each other such that if one executive process fails during therapy, the other executive transitions the machine to a safe state.

"Therapy conditions" are caused by a status or variable associated with the therapy going outside of allowable bounds. For example, a therapy condition may be caused by an out-of-bounds sensor reading. These conditions may be associated with an alert or an alarm, and then logged. Alarms are critical events, generally requiring immediate action. Alarms may be prioritized, for example as low, medium or high, based on the severity of the condition. Alerts are less critical than alarms, and generally do not have any associated risk other than loss of therapy or discomfort. Alerts may fall into one of three categories: message alerts, escalating alerts, and user alerts.

The responsibility for detecting therapy conditions that may cause an alarm or alert condition is shared between the UI model and therapy subsystems. The UI model subsystem 360 (FIG. 47) is responsible for detecting alarm and alert conditions pre-therapy and post-therapy. The therapy subsystem 340 (FIG. 46) is responsible for detecting alarm and alert conditions during therapy.

The responsibility for handling alerts or alarms associated with therapy conditions is also shared between the UI model and therapy subsystems. Pre-therapy and post-therapy, the UI model subsystem 360 is responsible for handling the alarm or alert condition. During a therapy session, the therapy subsystem 340 is responsible for handling the alarm or alert condition and notifying the UI Model Subsystem an alarm or alert condition exists. The UI model subsystem 360 is responsible for escalating alerts, and for coordinating with the UI view subsystem 338 to provide the user with visual and/or audio feedback when an alarm or alert condition is detected.

"System operation conditions" do not have an alert or alarm associated with them. These conditions are simply logged to provide a record of system operations. Auditory or visual feedback need not be provided.

Actions that may be taken in response to the system error conditions, therapy conditions, or system operation conditions described above are implemented by the subsystem (or layer) that detected the condition, which sends the status up to the higher subsystems. The subsystem that detected the condition may log the condition and take care of any safety considerations associated with the condition. These safety considerations may comprise any one or combination of the following: pausing the therapy and engaging the occluder; clearing states and timers as needed; disabling the heater; ending the therapy entirely; deactivating the safe line to close the occluder, shut off the heater, and removing power from the valves; and preventing the cycler from running therapies even after a power cycle to require the system to be sent back to service. The UI subsystem 334 may be responsible for conditions that can be cleared automatically (i.e., non-latching conditions) and for user recoverable conditions that are latched and can only be cleared by user interaction.

Each condition may be defined such that it contains certain information to allow the software to act according to the severity of the condition. This information may comprise a numeric identifier, which may be used in combination with a lookup table to define priority; a descriptive name of the error (i.e., a condition name); the subsystem that detected the condition; a description of what status or error triggers the condition; and flags for whether the condition implements one or more actions defined above.

Conditions may be ranked in priority such that when multiple conditions occur, the higher priority condition may be handled first. This priority ranking may be based on whether the condition stops the administration of therapy. When a condition occurs that stops therapy, this condition takes precedence when relaying status to the next higher subsystem. As discussed above, the subsystem that detects a condition handles the condition and sends status information up to the subsystem above. Based on the received status information, the upper subsystem may trigger a different condition that may have different actions and a different alert/alarm associated with it. Each subsystem implements any additional actions associated with the new condition and passes status information up to the subsystem above. According to one exemplary implementation, the UI subsystem only displays one alert/alarm at a given time. In this case, the UI model sorts all active events by their priority and displays the alert/alarm that is associated with the highest priority event.

A priority may be assigned to an alarm based on the severity the potential harm and the onset of that harm. Table 1, below, shows an example of how priorities may be assigned in this manner.

TABLE 1

| POTENTIAL RESULT OF FAILURE TO RESPOND TO THE CAUSE OF ALARM CONDITION | ONSET OF POTENTIAL HARM | | |
| --- | --- | --- | --- |
| | IMMEDIATE | PROMPT | DELAYED |
| death or irreversible injury | high priority | high priority | medium priority |
| reversible injury | high priority | medium priority | low priority |
| minor discomfort or injury | medium priority | low priority | low priority or no alarm signal |

In the context of Table 1, the onset of potential harm refers to when an injury occurs and not to when it is manifested. A potential harm having an onset designated as "immediate" denotes a harm having the potential to develop within a period of time not usually sufficient for manual corrective action. A potential harm having an onset designated as "prompt" denotes a harm having the potential to develop within a period of time usually sufficient for manual corrective action. A potential harm having an onset designated as "delayed" denotes a harm having the potential to develop within an unspecified time greater than that given under "prompt."

Figure 50:
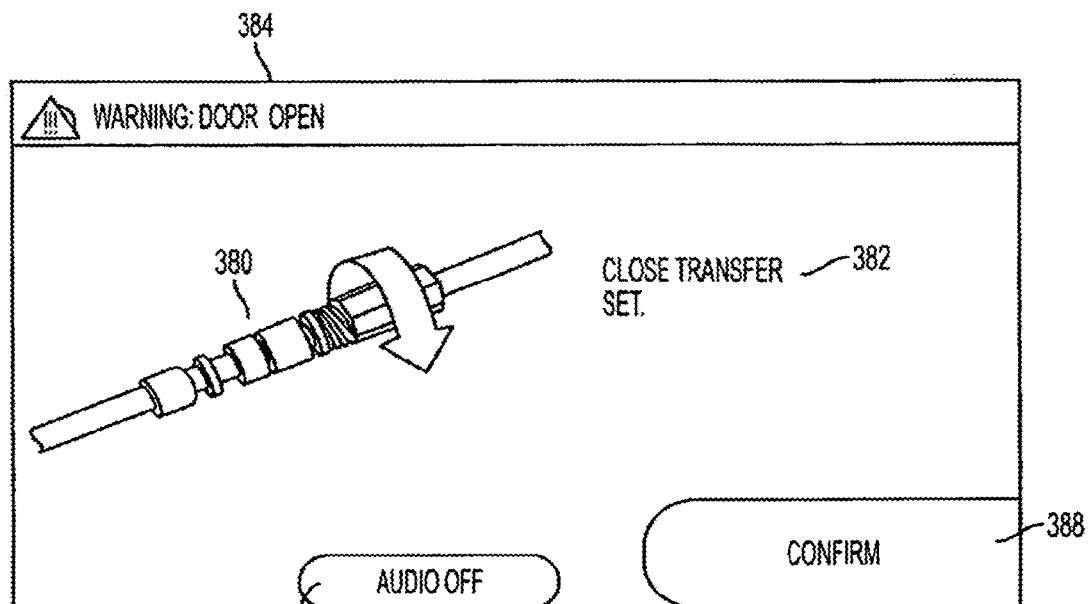
FIGS. 50-55 show exemplary screen views relating to alerts and alarms that may be displayed on a touch screen user interface for the APD system.
Figure 51:
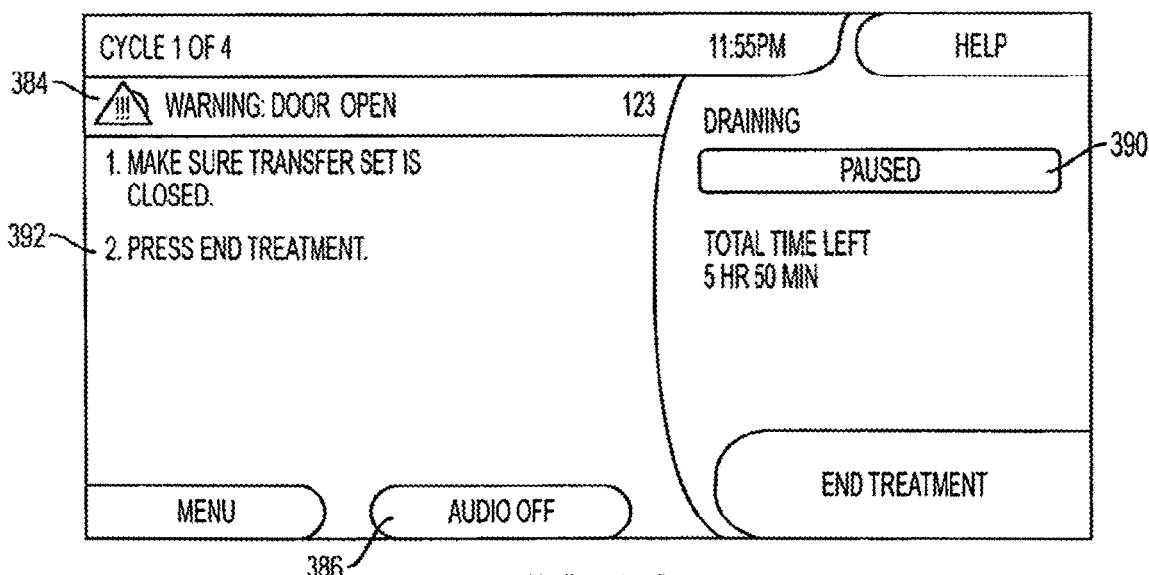

FIGS. 50-55 show exemplary screen views relating to alerts and alarms that may be displayed on a touch screen user interface. FIG. 50 shows the first screen of an alarm, which includes a diagram 380 and text 382 instructing a user to close their transfer set. The screen includes a visual warning 384, and is also associated with an audio warning. The audio warning may be turned off my selecting the "audio off" option 386 on the touch screen. When the user has closed the transfer set, the user selects the "confirm" option 388 on the touch screen. FIG. 51 shows a similar alarm screen instructing a user to close their transfer set. In this case, an indication that draining is paused 390 and an instruction to select "end treatment" are provided 392.

As previously discussed, alerts generally do not have associated risk other than loss of therapy or discomfort. Thus, an alert may or may not cause the therapy to pause. Alerts can be either "auto recoverable," such that if the event clears the alert automatically clears, or "user recoverable," such that user interaction with the user interface is needed to clear the alert. An audible alert prompt, which may have a volume that may be varied within certain limits, may be used to bring an alert to the attention of a user. In addition, information or an instruction may be displayed to the user. So that such information or instruction may be viewed by the user, an auto-dim feature of the user interface may be disabled during alerts.

In order to reduce the amount of disturbance the user, alerts can may be categorized into different types based on how important an alert is and how quick a user response is required. Three exemplary types of alerts are a "message alert," an "escalating alert," and a "user alert." These alerts have different characteristics based on how information is visually presented to the user and how the audible prompt is used.

Figure 52:
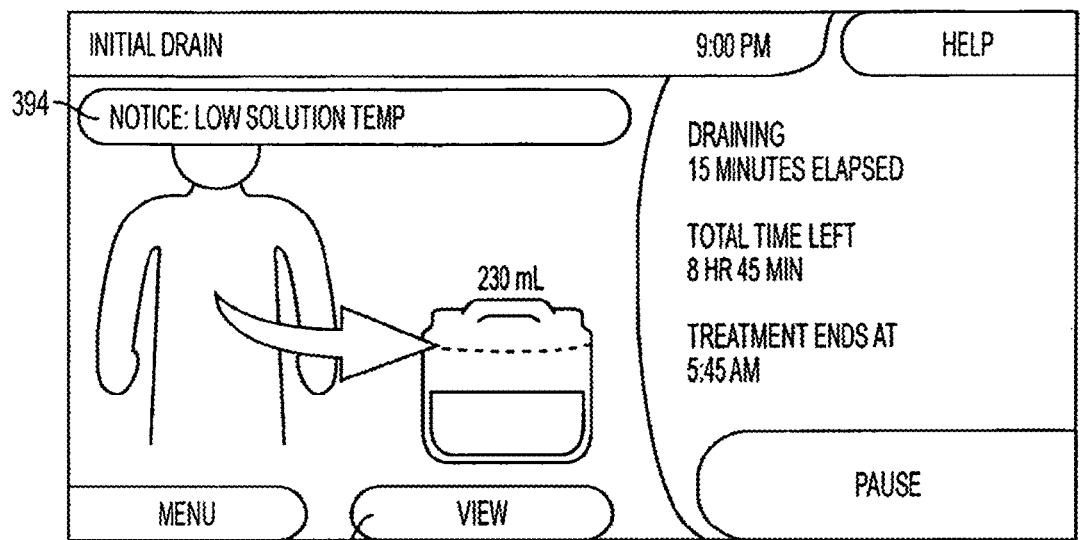
Figure 53:
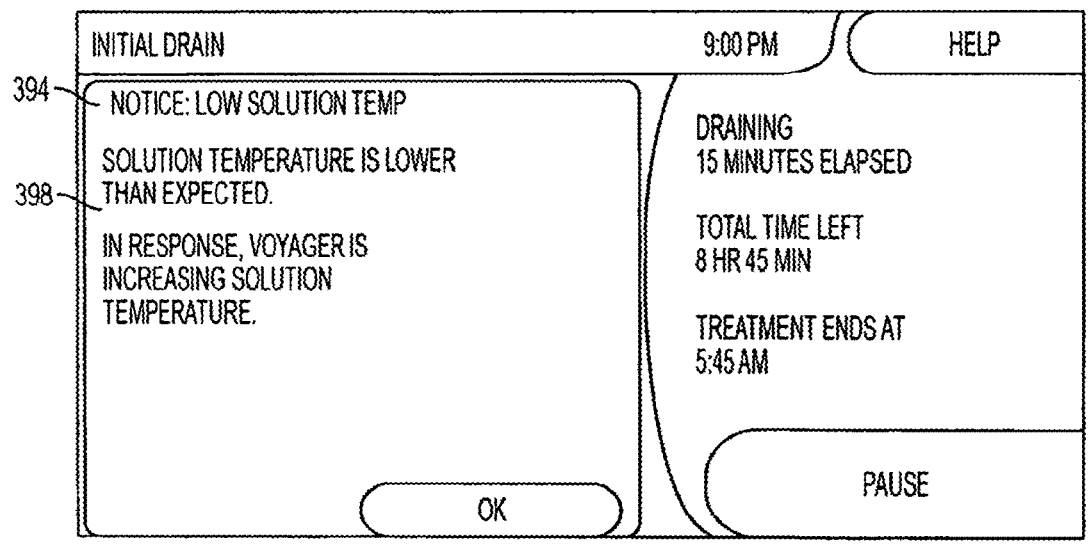

A "message alert" may appear at the top of a status screen and is used for informational purposes when a user interaction is not required. Because no action needs to be taken to clear the alert, an audible prompt is generally not used to avoid disturbing, and possibly waking, the patient. However, an audible alert may be optionally presented. FIG. 52 shows an exemplary message alert. In particular, FIG. 52 shows an under-temperature message alert 394 that may be used to inform a user when the dialysate is below a desired temperature or range. In this case, a user does not need to take any action, but is informed that therapy will be delayed while the dialysate is heated. If the patient desires more information, the "view" option 396 may be selected on the touch screen. This causes additional information 398 concerning the alert to appear on the screen, as shown in FIG. 53. A message alert may also be used when there is a low flow event that the user is trying to correct. In this case, a message alert may be displayed until the low flow event is cleared to provide feedback to the user on whether the user fixed the problem.

An "escalating alert" is intended to prompt the user to take action in a non-jarring manner. During an escalating alert, a visual prompt may displayed on the touch screen and an audible prompt may be presented (e.g., once). After a given period of time, if the event that caused the alert is not cleared, a more emphatic audible prompt may be presented. If the event causing the alert is not cleared after an additional period of time, the alert is escalated to a "user alert." According to one exemplary implementation of a user alert, a visual prompt is displayed until the alert is cleared and an audible prompt, which can be silenced, is presented. The UI subsystem does not handle the transition to from escalating alert to user alert. Rather, the subsystem that triggered the original event will trigger a new event associated with the user alert.

Figure 54:
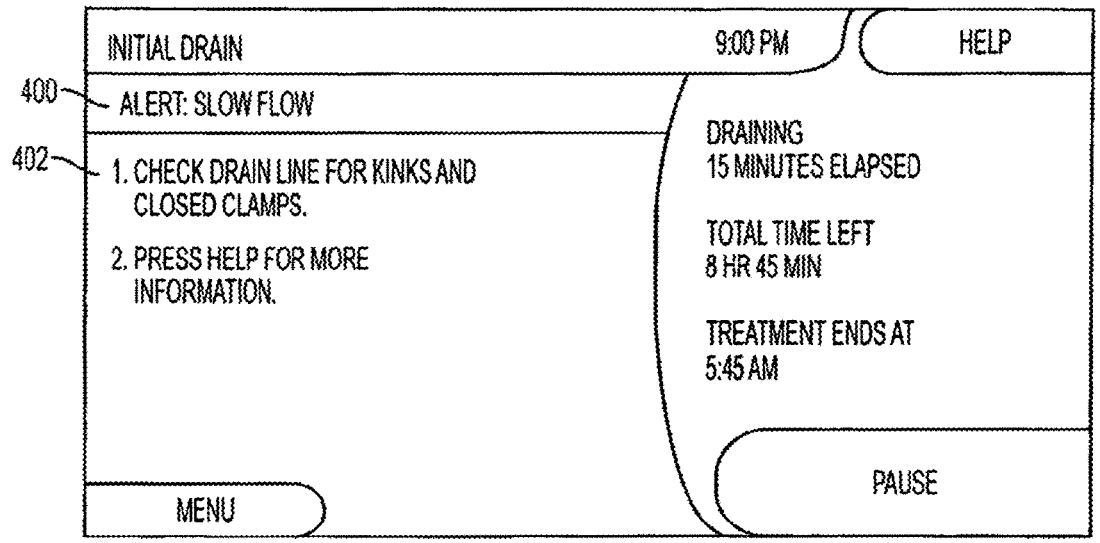
Figure 55:
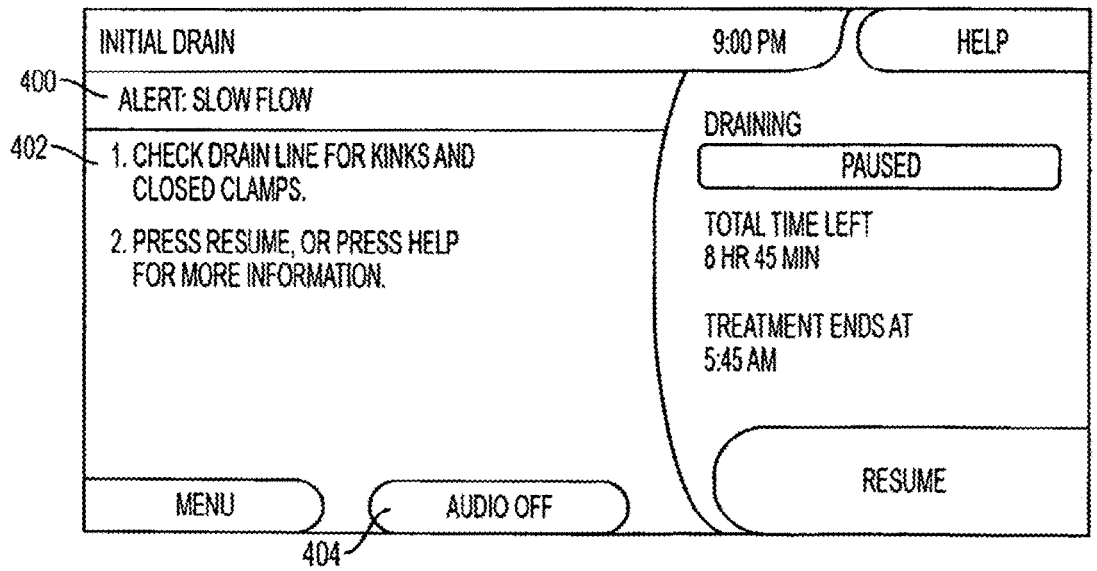

FIG. 54 shows a screen view displaying information concerning an escalating alert. This exemplary alert includes an on-screen alert message 400 and a prompt 402 instructing the user to check the drain line for kinks and closed clamps, as well as and an audible prompt. The audible prompt may be continuous until it is silenced by the user. FIG. 55 shows a screen view including an "audio off" option 404 that may be selected to silence the audible prompt. This alert can be used directly, or as part of the escalating alert scheme.

Each alert/alarm is specified by: an alert/alarm code, which is a unique identifier for the alert/alarm; an alert/alarm name, which is a descriptive name of the alert/alarm; an alert/alarm type, which comprises the type of alert or level of alarm; an indication of whether an audible prompt is associated with the alert/alarm; an indication of whether the alert and associated event can be bypassed (or ignored) by the user; and the event code of the event or events that trigger the alert/alarm.

During alarms, escalating alerts and user alerts, the event code (which may be different from the alert or alarm code, as described above) may be displayed on the screen so that the user can read the code to service personnel if needed. Alternatively or additionally, a voice guidance system may be used so that, one connected to a remote call center, the system can vocalize pertinent information about the system configuration, state, and error code. The system may be connected to the remote call center via a network, telephonic connection, or some other means.

Figure 56:
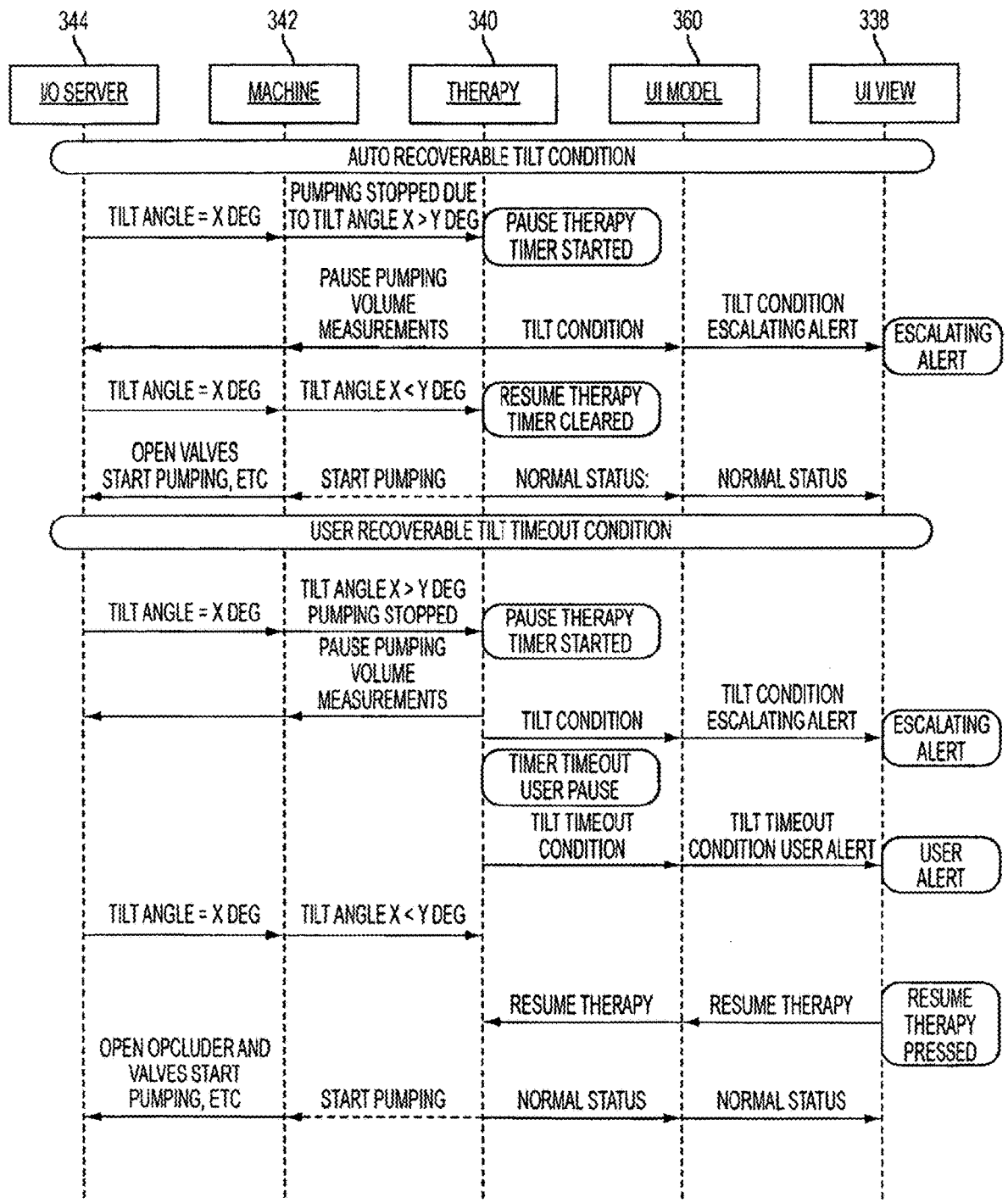
FIG. 56 illustrates component states and operations for error condition detection and recovery in an illustrative embodiment.

An example of a condition detected by the therapy subsystem is described below in connection with FIG. 56. The condition results when the APD system is not positioned on a level surface, which is important for air management. More particularly, the condition results when a tilt sensor detects that APD system is tilted beyond a predetermined threshold, such as 35°, with respect to a horizontal plane. As described below, a recoverable user alert may be generated by the therapy subsystem if the tilt sensor senses an angle with an absolute value greater than the predetermined threshold. To avoid nuisance alarms, the user may be directed to level the APD system before therapy begins. The tilt threshold may be lower during this pre-therapy period (e.g., 35°). The user may also be given feedback concerning whether the problem is corrected.

When the tilt sensor detects an angle of tilt exceeding a threshold during therapy, the machine subsystem 342 responds by stopping the pump in a similar manner as if it had detected air in the pump chamber. The therapy subsystem 340 asks for status and determines that the machine layer 342 has paused pumping due to tilt. It also receives status information concerning the angle of the machine. At this point, the therapy subsystem 340 generates a tilt condition, pauses therapy, and sends a command to the machine subsystem 342 to pause pumping. This command triggers clean-up, such as taking fluid measurement system (FMS) measurements and closing the patient valve. The therapy subsystem 340 also starts a timer and sends an auto recoverable tilt condition up to the UI model 360, which sends the condition to the UI view 338. The UI view 338 maps the condition to an escalating alert. The therapy subsystem 340 continues to monitor the tilt sensor reading and, if it drops below the threshold, clears the condition and restarts therapy. If the condition does not clear before the timer expires, the therapy subsystem 340 triggers a user recoverable "tilt timeout" condition that supersedes the auto-recoverable tilt condition. It sends this condition to the UI model 360, which sends the condition to the UI view 338. The UI view 338 maps the condition to a user alert. This condition can not be cleared until a restart therapy command is received from the UI subsystem (e.g., the user pressing the resume button). If the tilt sensor reading is below the threshold, the therapy resumes. If it is not below the threshold, the therapy layer triggers an auto recoverable tilt condition and starts the timer.

Screen Display

As discussed previously, the UI view subsystem 338 (FIG. 47) is responsible for the presentation of the interface to the user. The UI view subsystem is a client of and interfaces with the UI model subsystem 360 (FIG. 47) running on the automation computer. For example, the UI view subsystem communicates with the UI model subsystem to determine which screen should be displayed to the user at a given time. The UI view may include templates for the screen views, and may handle locale-specific settings such as display language, skin, audio language, and culturally sensitive animations.

Figure 57:
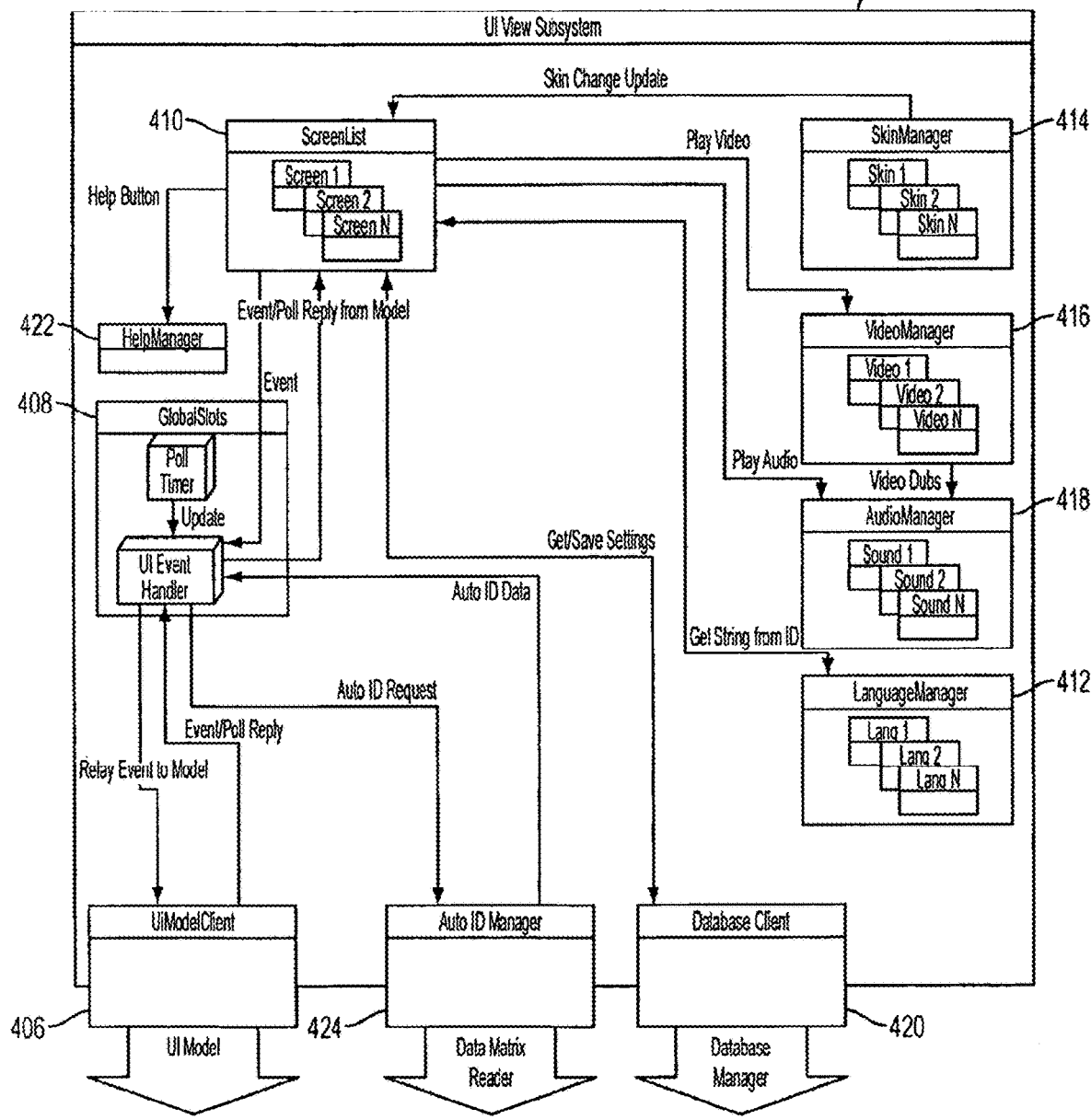
FIG. 57 shows exemplary modules of a UI view subsystem for the APD system.

There are three basic types of events that occur in the UI view subsystem. These are local screen events that are handled by the individual screens, model events in which a screen event must propagate down to the UI model subsystem, and polling events that occur on a timer and query the UI model subsystem for status. A local screen event only affects the UI view level. These events can be local screen transitions (e.g., in the case of multiple screens for a single model state), updates to view settings (e.g., locality and language options), and requests to play media clips from a given screen (e.g., instructional animations or voice prompts). Model events occur when the UI view subsystem must consult with the UI model subsystem to determine how to handle the event. Examples that fall into this category are the confirmation of therapy parameters or the pressing of the "start therapy" button. These events are initiated by the UI view subsystem, but are handled in the UI model subsystem. The UI model subsystem processes the event and returns a result to the UI view subsystem. This result drives the internal state of the UI view subsystem. Polling events occur when a timer generates a timing signal and the UI model subsystem is polled. In the case of a polling event, the current state of the UI view subsystem is sent to the UI model subsystem for evaluation. The UI model subsystem evaluates the state information and replies with the desired state of the UI view subsystem. This may constitute: (1) a state change, e.g., if the major states of the UI model subsystem and the UI view subsystem are different, (2) a screen update, e.g., if values from the UI model subsystem change values displayed on-screen, or (3) no change in state, e.g., if the state of the UI model subsystem and the UI view subsystem are identical. FIG. 57 shows the exemplary modules of the UI view subsystem 338 that perform the functions described above.

As shown in FIG. 57, the UI model client module 406 is used to communicate events to the UI model. This module 406 is also used to poll the UI model for the current status. Within a responsive status message, the UI model subsystem may embed a time to be used to synchronize the clocks of the automation computer and the user interface computer.

The global slots module 408 provides a mechanism by which multiple callback routines (slots) can subscribe to be notified when given events (signals) occur. This is a "many-to-many" relationship, as a slot can be bound to many signals, and likewise a signal can be bound to many slots to be called upon its activation. The global slots module 408 handles non-screen specific slots, such as application level timers for UI model polling or button presses that occur outside of the screen (e.g., the voice prompt button).

The screen list class 410 contains a listing of all screens in the form of templates and data tables. A screen is made up of a template and an associated data table that will be used to populate that screen. The template is a window with widgets laid out on it in a generic manner and with no content assigned to the widgets. The data table includes records that describe the content used to populate the widgets and the state of the widgets. A widget state can be checked or unchecked (in the case of a checkbox style widget), visible or hidden, or enabled or disabled. The data table can also describe the action that occurs as a result of a button press. For example, a button on window 'A' derived from template '1' could send an event down to the UI model, whereas that same button on window 'B' also derived from template '1' could simply cause a local screen transition without propagating the event down to the UI model. The data tables may also contain an index into the context-sensitive help system.

The screen list class 410 forwards data from the UI model to the intended screen, selects the proper screen-based data from the UI model, and displays the screen. The screen list class 410 selects which screen to display based on two factors: the state reported by the UI model and the internal state of the UI view. In some cases, the UI model may only inform the UI view that it is allowed to display any screen within a category. For example, the model may report that the machine is idle (e.g., no therapy has been started or the setup phase has not yet occurred). In this case, it is not necessary to confer with the UI model when the user progresses from a menu into its sub-menu. To track the change, the UI view will store the current screen locally. This local sequencing of screens is handled by the table entries described above. The table entry lists the actions that respective buttons will initiate when pressed.

The language manager class 412 is responsible for performing inventory on and managing translations. A checksum may be performed on the list of installed languages to alert the UI view if any of the translations are corrupted and or missing. Any class that wants a string translated asks the language manager class 412 to perform it. Translations may be handled by a library (e.g., Qt®). Preferably, translations are requested as close as possible to the time of rendering. To this end, most screen template member access methods request a translation right before handing it to the widget for rendering.

A skin comprises a style-sheet and images that determine the "look and feel" of the user interface. The style-sheet controls things such as fonts, colors, and which images a widget will use to display its various states (normal, pressed, disabled, etc.). Any displayed widget can have its appearance altered by a skin change. The skin manager module 414 is responsible for informing the screen list and, by extension, the screen widgets, which style-sheet and skin graphics should be displayed. The skin manager module 414 also includes any animated files the application may want to display. On a skin change event, the skin manager will update the images and style-sheet in the working set directory with the proper set, which is retrieved from an archive.

The video manager module 416 is responsible for playing locale-appropriate video given a request to display a particular video. On a locale change event, the video manager will update the videos and animations in the working set directory with the proper set from an archive. The video manager will also play videos that have accompanying audio in the audio manager module 418. Upon playback of these videos, the video manager module 416 will make the appropriate request to the audio manager module 418 to play the recording that belongs to the originally requested video clip.

Similarly, the audio manager module 418 is responsible for playing locale-appropriate audio given a request to play a particular audio clip. On a locale change event, the audio manager will update the audio clips in the working set directory with the proper set from an archive. The audio manager module 418 handles all audio initiated by the UI view. This includes dubbing for animations and sound clips for voice prompts.

The database client module 420 is used to communicate with the database manager process, which handles the interface between the UI view subsystem and the database server 366 (FIG. 47). The UI view uses this interface to store and retrieve settings, and to supplement therapy logs with user-provided answers to questions about variables (e.g., weight and blood pressure).

The help manager module 422 is used to manage the context-sensitive help system. Each page in a screen list that presents a help button may include an index into the context-sensitive help system. This index is used so that the help manager can display the help screen associated with a page. The help screen may include text, pictures, audio, and video.

The auto ID manager 424 is called upon during pre-therapy setup. This module is responsible for capturing an image (e.g., a photographic image) of a solution bag code (e.g., a datamatrix code). The data extracted from the image is then sent to the machine control subsystem to be used by the therapy subsystem to identify the contents of a solution bag, along with any other information (e.g., origin) included in the code.

Using the modules described above, the UI view subsystem 338 renders the screen views that are displayed to the user via the user interface (e.g., display 324 of FIG. 45). FIGS. 58-64 show exemplary screen views that may be rendered by the UI view subsystem. These screen views illustrate, for example, exemplary input mechanisms, display formats, screen transitions, icons and layouts. Although the screens shown are generally displayed during or before therapy, aspects of the screen views may be used for different input and output functions than those shown.

Figure 58:
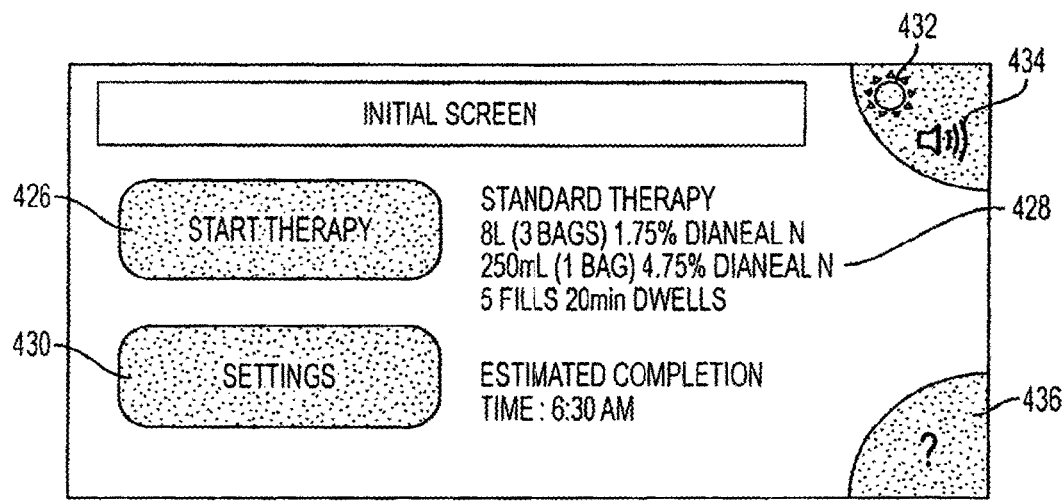
FIGS. 58-64 shows illustrative user interface screens for providing user information and receiving user input in illustrative embodiments regarding system setup, therapy status, display settings, remote assistance, and parameter settings.

The screen shown in FIG. 58 is an initial screen that provides the user the option of selecting between "start therapy" 426 to initiate the specified therapy 428 or "settings" 430 to change settings. Icons 432 and 434 are respectively provided to adjust brightness and audio levels, and an information icon 436 is provided to allow the user to solicit more information. These icons may appear on other screens in a similar manner.

Figure 59:
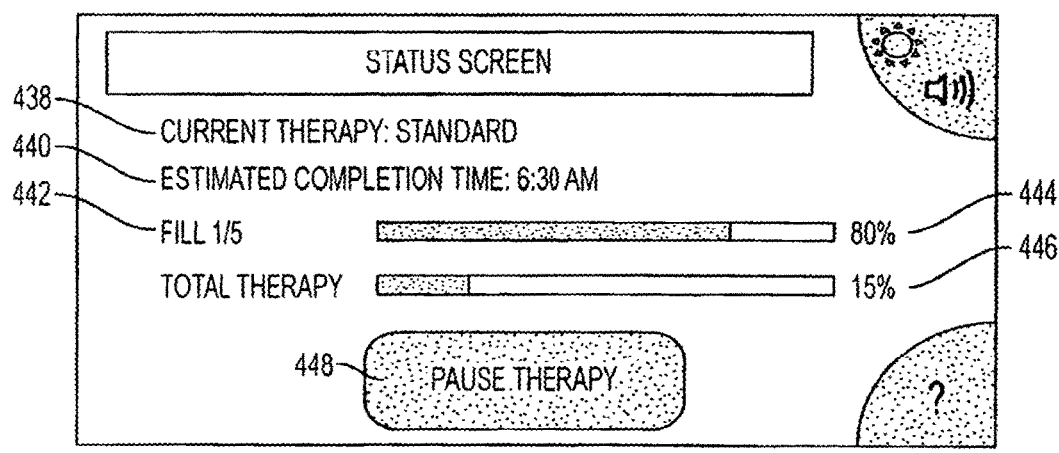

FIG. 59 shows a status screen that provides information the status of the therapy. In particular, the screen indicates the type of therapy being performed 438, the estimated completion time 440, and the current fill cycle number and total number of fill cycles 442. The completion percentage of the current fill cycle 444 and the completion percentage of the total therapy 446 are both numerically and graphically displayed. The user may select a "pause" option 448 to pause therapy.

Figure 60:
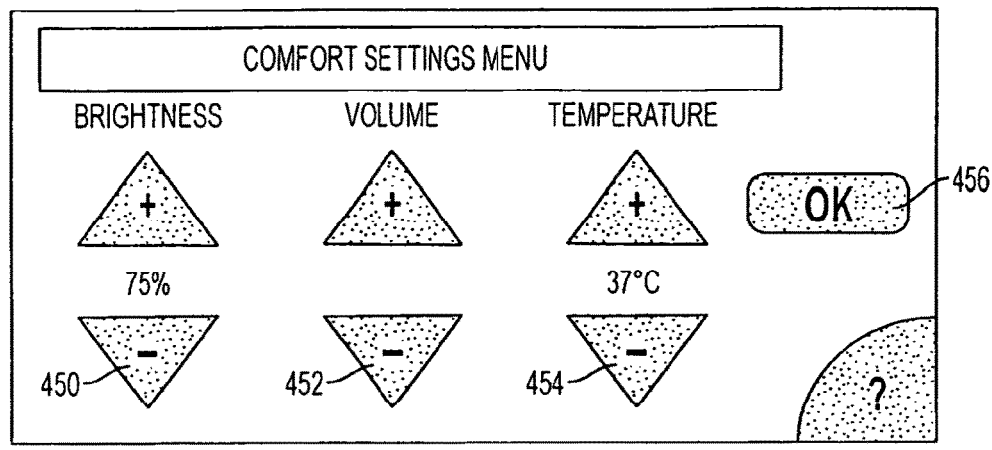

FIG. 60 shows a menu screen with various comfort settings. The menu includes brightness arrows 450, volume arrows 452 and temperature arrows 454. By selecting either the up or down arrow in each respective pair, a user can increase or decrease screen brightness, audio volume, and fluid temperature. The current brightness percentage, volume percentage and temperature are also displayed. When the settings are as desired, a user may select the "OK" button 456.

Figure 61:
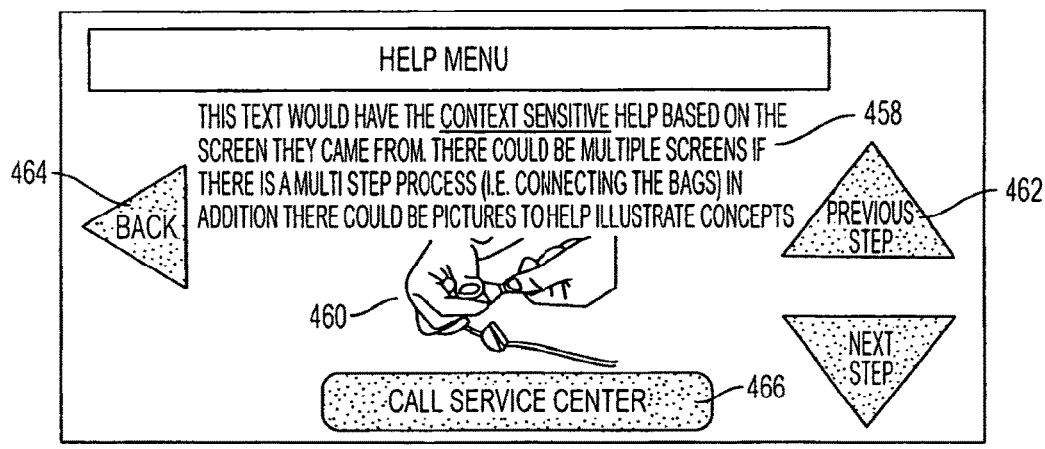

FIG. 61 shows a help menu, which may be reached, for example, by pressing a help or information button on a prior screen. The help menu may include text 458 and/or an illustration 460 to assist the user. The text and/or illustration may be "context sensitive," or based on the context of the prior screen. If the information provided to the user cannot conveniently be provided in one screen, for example in the case of a multi-step process, arrows 462 may be provided to allow the user to navigate backward and forward between a series of screens. When the user has obtained the desired information, he or she may select the "back" button 464. If additional assistance is required, a user may select the "call service center" option 466 to have the system contact the call service center.

Figure 62:
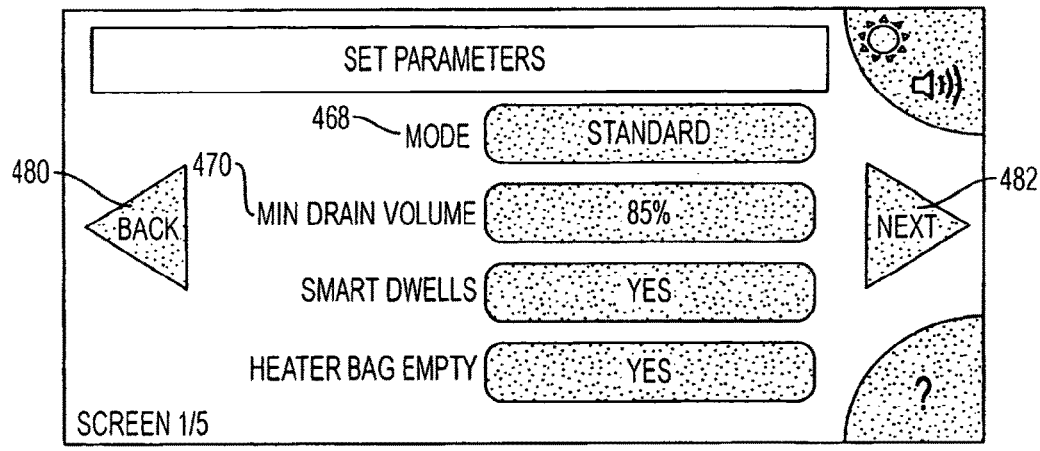
Figure 63:
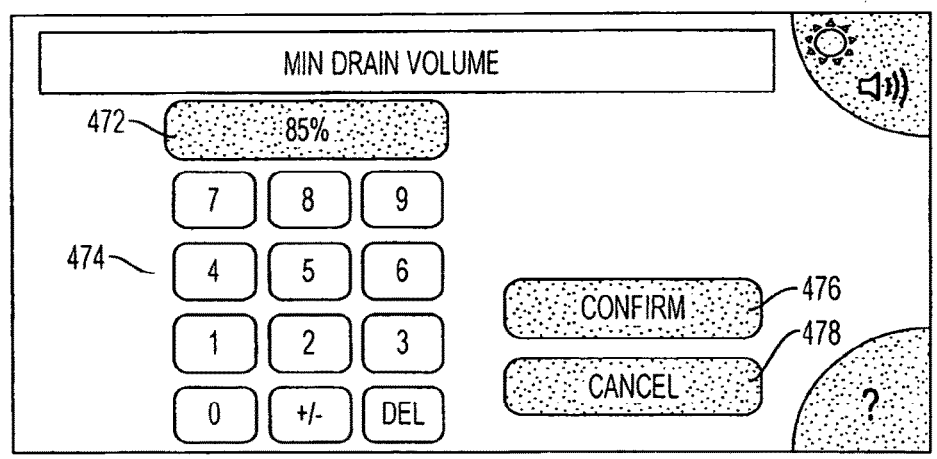

FIG. 62 illustrates a screen that allows a user to set a set of parameters. For example, the screen displays the current therapy mode 468 and minimum drain volume 470, and allows a user to select these parameters to be changed. Parameters may be changed in a number of ways, such as by selecting a desired option from a round robin style menu on the current screen. Alternatively, when the user selects a parameter to be changed, a new screen may appear, such as that shown in FIG. 63. The screen of FIG. 63 allows a user to adjust the minimum drain volume by inputting a numeric value 472 using a keypad 474. Once entered, the user may confirm or cancel the value using buttons 476 and 478. Referring again to FIG. 62, a user may then use the "back" and "next" arrows 480, 482 to navigate through a series of parameters screens, each including a different set of parameters.

Figure 64:
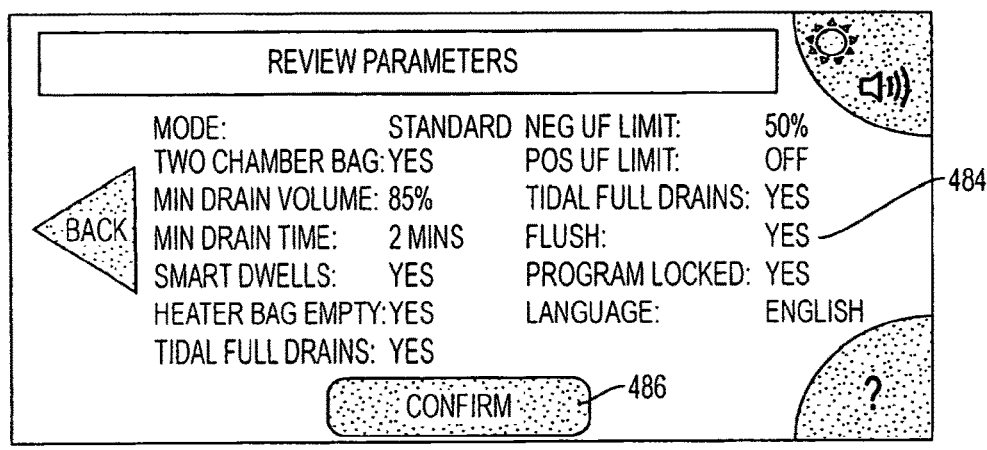

Once all desired parameters have been set or changed (e.g., when the user has navigated through the series of parameters screens), a screen such as that shown in FIG. 64 may be presented to allow a user to review and confirm the settings. Parameters that have changed may optionally be highlighted in some fashion to draw the attention of the user. When the settings are as desired, a user may select the "confirm" button 486.

While aspects of the invention have been described in conjunction with specific embodiments thereof, it is evident that many alternatives, modifications, and variations will be apparent to those skilled in the art. Accordingly, embodiments of the invention as set forth herein are intended to be illustrative, not limiting. Various changes may be made without departing from the spirit and scope of the invention.

The invention claimed is:

1. A fluid handling cassette for use in a medical infusion system, the fluid handling cassette comprising:
 a generally planar body having a first pump chamber and a second pump chamber each formed as a depression in a first side of the body, each pump chamber of the first pump chamber and the second pump chamber having a first port and a second port connecting a respective pump chamber of the first pump chamber and the second pump chamber to a second side of the body;
 a plurality of valve wells on the first side of the body including a first group of valve wells and a second group of valve wells, valve wells in the first group of valve wells each comprising a valve port and an opening, both of the valve port and the opening connecting a respective valve well of the first group of valve wells to the second side of the body;
 valve wells in the second group of valve wells each comprising a valve port connecting a respective valve well of the second group of valve wells to the second side of the body, each of the valve wells of the second group of valve wells being connected to the second side of the body only by a respective valve port of the valve ports of the valve wells of the second group of valve wells;
 a plurality of cassette ports including at least three cassette ports located on a first end of the body and at least three cassette ports on a second end of the body, each of the plurality of cassette ports being directly connected to a respective valve well of the second group of valve wells; and
 a first fluid flowpath and a second fluid flowpath on the second side of the body, each fluid flowpath of the first fluid flowpath and the second fluid flowpath connected to the first port or the second port of a respective pump chamber of the first pump chamber and the second pump chamber via a valve well of the first group of valve wells;
 wherein each cassette port of the plurality of cassette ports is connected to one fluid flowpath of the first fluid flowpath and the second fluid flowpath via the respective valve well of the second group of valve wells.

2. The fluid handling cassette of claim 1, wherein the second fluid flowpath is connected to a patient line cassette port of the plurality of cassette ports, the patient line cassette port configured for connection to a patient line.

3. The fluid handling cassette of claim 1, wherein the first fluid flowpath is connected to a drain line cassette port and a heater line cassette port of the plurality of cassette ports, the drain line cassette port configured for connection to a drain line, and the heater line cassette port configured for connection to a heater bag line.

4. The fluid handling cassette of claim 1, wherein the plurality of cassette ports includes at least one solution line spike located at the second end of the body.

5. The fluid handling cassette of claim 4, wherein each of the at least one solution line spike located at the second end of the body includes a lumen connected to the respective valve well of the second group of valve wells.

6. The fluid handling cassette of claim 4, wherein the second fluid flowpath is connected to the at least one solution line spike via the respective valve well of the second group of valve wells.

7. The fluid handling cassette of claim 1, wherein the cassette comprises a first flexible membrane attached to the first side of the body over the first pump chamber and the second pump chamber and the plurality of valve wells, wherein the first flexible membrane over the first pump chamber and the second pump chamber is configured for moving fluid in the first pump chamber and the second pump chamber, and the first flexible membrane over the plurality of valve wells is configured for selectively occluding the valve ports of respective valve wells of the plurality of valve wells.

8. The fluid handling cassette of claim 1, wherein the first fluid flowpath and the second fluid flowpath comprise walls on the second side of the body, and wherein the fluid handling cassette comprises a rigid or flexible sheet attached to the second side of the body, wherein the rigid or flexible sheet is configured to make sealing contact with the walls to form the first fluid flowpath and the second fluid flowpath.

9. A fluid handling cassette for use in a medical infusion system, the fluid handling cassette comprising:
 a generally planar body having a first pump chamber and a second pump chamber each formed as a depression in a first side of the body, each pump chamber of the first pump chamber and the second pump chamber having a first port and a second port connecting a respective pump chamber of the first pump chamber and the second pump chamber to a second side of the body;
 a plurality of valve wells on the first side of the body including a first group of valve wells and a second group of valve wells, valve wells in the first group of valve wells each comprising a valve port and an opening connecting a respective valve well of the first group of valve wells to the second side of the body;
 valve wells in the second group of valve wells each comprising a valve port connecting a respective valve well of the second group of valve wells to the second side of the body, each of the valve wells of the second group of valve wells being connected to the second side of the body only by a respective valve port of the valve ports of the valve wells of the second group of valve wells;
 a plurality of cassette ports including at least four cassette ports located on a first end of the body; and
 a first fluid flowpath and a second fluid flowpath on the second side of the body, each fluid flowpath of the first fluid flowpath and the second fluid flowpath connected to the first port or the second port of a respective pump chamber of the first pump chamber and the second pump chamber via only a respective one valve well of the first group of valve wells;
 wherein each cassette port of the plurality of cassette ports is connected to one fluid flowpath of the first fluid flowpath and the second fluid flowpath via a respective valve well of the second group of valve wells.

* * * * *